(12) United States Patent
Lin et al.

(10) Patent No.: US 10,822,602 B2
(45) Date of Patent: Nov. 3, 2020

(54) AGARASE, COMPOSITION CONTAINING THE SAME, AND APPLICATION THEREOF

(71) Applicant: AGRICULTURAL TECHNOLOGY RESEARCH INSTITUTE, Hsinchu (TW)

(72) Inventors: Jiunn-Horng Lin, Hsinchu (TW); Jyh-Perng Wang, Hsinchu (TW); Zeng-Weng Chen, Hsinchu (TW); Hui-Jie Lin, Hsinchu (TW); Shu-Wei Chang, Hsinchu (TW); Weng-Zeng Huang, Hsinchu (TW); Jian-Fong Lai, Hsinchu (TW); Shih-Ling Hsuan, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 189 days.

(21) Appl. No.: 15/463,311

(22) Filed: Mar. 20, 2017

(65) Prior Publication Data
US 2018/0044654 A1    Feb. 15, 2018

(30) Foreign Application Priority Data
Aug. 12, 2016  (TW) .............................. 105125723 A

(51) Int. Cl.
*C12N 9/24* (2006.01)
*C12N 9/38* (2006.01)

(52) U.S. Cl.
CPC .... *C12N 9/2468* (2013.01); *C12Y 302/01081* (2013.01)

(58) Field of Classification Search
None
See application file for complete search history.

(56) References Cited

U.S. PATENT DOCUMENTS

2009/0053776 A1* 2/2009 Hutcheson ............. C12N 11/02
435/100

OTHER PUBLICATIONS

Uniprot, Accession No. A0A0U4ZSX2, 2016, www.uniprot.org.*
Uetanabaro et al., *Paenibacillus agarexedens* sp. nov., nom. rev., and *Paenibacillus agaridevorans* sp. nov., Int. J. Syst. Evol. Microbiol., 2003, 53, 1051-57.*
Taiwan Biodiversity Information Facility, Occurrence Record #367273, accessed Jul. 19, 2018, taibif.tw/en/occurrence/id/367272.*
Lee et al., Cloning, Expression, and Characterization of a Glycoside Hydrolase Family 118 beta-Agarase from *Agarivorans* sp. JA-1 , J. Microbiol. Biotechnol., 2012, 22, 1692-97.*
Genbank, Accession No. AYA22371.1, 2018, www.ncbi.nlm.nih.gov.*
Armetnteros et al. ("SignalP 5.0 improves signal peptide predictions using deep neural networks," Nature Biotechnol., doi:10.1038/s41587-019-0036-z (2019).*
Petersen et al., SignalP 4.0: discriminating signal peptides from transmembrane regions, Nature Methods, 2011, 8, 785-86.*
Yoon et al., Purification and comparison of properties of the C-terminus truncated agarase of *Pseudomonas* sp. W7, J. Microbiol. Biotechnol., 2003, 13, 767-72.*
Han et al., Deletion of a Non-Catalytic Region Increases the Enzymatic Activity of a β-Agarase from *Flammeovirga* sp. MY04, J. Ocean Univ. China, 2015, 14, 841-84.*

* cited by examiner

*Primary Examiner* — Robert B Mondesi
*Assistant Examiner* — Todd M Epstein
(74) *Attorney, Agent, or Firm* — Birch Stewart Kolasch & Birch, LLP

(57) ABSTRACT

The present invention provides a β-agarase, a composition containing the same and applications thereof. The present β-agarase provides the field a novel alternative and is favorable for the industrial utilities of the hydrolysis products of agarose. Furthermore, the present agarase is particularly modified for heterologous production by prokaryotic expression systems, and thereby is favorable for commercial use.

12 Claims, 6 Drawing Sheets

Specification includes a Sequence Listing.

SEQUENCE LISTING

```
<160> NUMBER OF SEQ ID NOS: 30

<210> SEQ ID NO 1
<211> LENGTH: 1811
<212> TYPE: PRT
<213> ORGANISM: Paenibacillus agarexedens

<400> SEQUENCE: 1

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45

Ile Gln Arg Ile Asn Phe Leu Gln Phe Pro Asp Gly Gln Tyr Leu Gln
    50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Gly Ser Val Ala Gln Thr
                85                  90                  95

Met Glu Leu Tyr Val Ile Asp Pro Asn Gly Val Glu Thr His Trp Thr
            100                 105                 110
```

```
Val Phe Gln Asn Gly Gly Trp Lys Asp Gly Ile Thr Gly Leu Tyr Thr
            115                 120                 125

Asn Tyr Thr Lys Met Gly Phe Gln Glu Asp Asn Pro Thr Glu Gly Ile
        130                 135                 140

Thr His Pro Trp Leu Ile Lys Gly Thr Asn Gly Asp Ile Ile Tyr Glu
145                 150                 155                 160

Gly Tyr Lys Met Lys Ile Val Gly Asn Gly Thr Leu Arg Ser Val Tyr
                165                 170                 175

His Trp Glu Glu Gly Val Pro Leu Glu Phe Asp Thr Ser Ala Trp
                180                 185                 190

Thr Val Leu Gly Gly Asp Lys Asp Ile Leu Asn Val Ser Val Asn Val
        195                 200                 205

Asp Ala Leu Thr Asn Leu Ser Met Asp Gly Val Asp Lys Leu Pro Glu
210                 215                 220

Glu Val Phe Lys Arg Tyr His Val Asn Ser Gly Pro Ile Gly Leu Glu
225                 230                 235                 240

Gln Ala Gly Gly Glu Phe Thr Val Leu Asp Glu Ala Tyr His Arg Thr
                245                 250                 255

Thr His Asp Tyr Gly Phe Thr Pro Gly Arg Gly Ala Phe His Tyr Asn
                260                 265                 270

Leu Leu Thr Ser Trp Ala Gly Leu Lys Glu Asp Pro Ala Arg Pro Gly
            275                 280                 285

Tyr Ala Asp Phe Thr Ala Thr Asn Glu Val Tyr Ala Lys Ser Gln Pro
        290                 295                 300

Ala Ile Asp Lys Phe Glu Ser Leu Tyr Pro Ser Ile Gly Lys Asp Tyr
305                 310                 315                 320

Val Leu Thr Leu Asp Gly Trp Pro Arg Trp Met Trp Glu Ser Pro Asn
                325                 330                 335

Ser Gly Gln Ser Glu His Phe Gly Thr Pro Ser Arg Ala Asn Phe Asp
                340                 345                 350

Ala Ala Ala Asp Ala Ser Ala Lys Leu Ile Lys Ser Ile Asp Thr Arg
            355                 360                 365

Phe Asp Gly Leu Gly Pro Lys Tyr Val Glu Val Lys Asn Glu Ser Thr
370                 375                 380

Ile Pro Gln Glu Trp Trp Phe Phe Gln Ser Glu Pro Glu Gln Ala Trp
385                 390                 395                 400

Ser Tyr Leu Ser Glu Phe His Asn Lys Val Ala Ala Glu Val Lys Ala
                405                 410                 415

Glu Asn Pro Asp Val Leu Val Gly Gly Pro Ser Ser Ala Phe Met Tyr
                420                 425                 430

Leu Glu Lys Asn Asp Phe Asp Glu Ala Arg Ala Gln Leu Lys Phe Met
            435                 440                 445

Asp Asp Thr Lys Asp Ser Leu Asp Trp Tyr Ser His Phe Tyr Glu
450                 455                 460

Asn Ala Asn Leu Phe Ile His Asp Arg Glu Asn Asn Ser Asp Gly Phe
465                 470                 475                 480

Leu Ser Gly Arg Met Glu Ala Val Leu Asp Leu Leu Asn Ala His Met
                485                 490                 495

Ala Asn Thr Asp Asn Val Lys Pro Ile Tyr Ile Thr Glu Glu Gly Thr
                500                 505                 510

Tyr Asn Thr Ala Gly Ser Asp Ala Asp Tyr Phe Gln Lys Leu Val Ala
            515                 520                 525

Phe Asn Gly Tyr Met Leu Arg Phe Ile Asn Tyr Ser Asp Thr Ile Gly
```

```
                530             535             540
Met Leu Val Pro Tyr Leu Tyr Pro Ile Ile Asn Trp Arg Pro Asn Ser
545                 550                 555                 560

Thr Gly Thr Phe Tyr Lys Tyr Asn Glu Thr Gln Asn Gly Leu Leu Glu
                565                 570                 575

Glu Met Thr Pro Met Glu Ala Tyr Leu Asp Met Trp Lys Asp Tyr Arg
                580                 585                 590

Gly Ala Phe Leu Pro Ser Glu Ala Asp Gln Glu Arg Val Phe Thr Asn
                595                 600                 605

Ala Val Arg Tyr Asn Asp Lys Val Tyr Val Ala Val His Asn Leu Asn
                610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
                645                 650                 655

Thr Tyr Glu Gln Lys Asn Val Ala Asp Leu Asn Asn Val Tyr Met Arg
                660                 665                 670

Val Gln Glu Met Ser Val Phe Glu Ile Thr Leu Asp Ser Asn Pro Pro
                675                 680                 685

Phe Thr Lys Thr Trp Glu Arg Glu Phe Ala Tyr Ala Pro Gln Glu Leu
                690                 695                 700

Val Pro Thr Ser Val Asn Ala Pro Ala Ser Phe Thr Val Gln Ala Arg
705                 710                 715                 720

Pro Ala Asp Leu Ala Lys Ala Thr Leu Arg Ile Gly Phe Gly Lys Thr
                725                 730                 735

Gly Ser Gly Phe Ala Glu Asp Met Gln Val Val Asn Ser Gly Asp
                740                 745                 750

Thr Ala Asn Met Gln Ser Phe Ser Lys Asp Leu Ala Tyr Thr Asp Lys
                755                 760                 765

Pro Gly Asn Leu Leu Thr Phe Ala Glu Phe Glu Leu Asp Thr Ser Lys
                770                 775                 780

Leu Leu Thr Ser Asn Thr Ile Glu Ile Thr Leu Pro Asp Asp Asp Gly
785                 790                 795                 800

Tyr Ile Thr Ser Val Gln Ile Ile Glu Tyr His Glu Gln Pro Ala Pro
                805                 810                 815

Thr Gly Ile Ala Thr Ser Ala Leu Ala Ala Pro Val Ala Asp Ala Lys
                820                 825                 830

Ser Lys Leu Ala Ser Thr Ile Ile Ser Ser Thr Gly Asn Glu Val Glu
                835                 840                 845

Pro Gly Gln Lys Trp Val Lys Lys His Ile Arg Asp Thr Leu Asn Ile
850                 855                 860

Glu Val Ala Lys Ala Glu Val Val Ala Gln Asp Ala Leu Ala Thr Asn
865                 870                 875                 880

Asp Glu Ile Thr Lys Ala Leu Glu Asp Leu Thr Lys Ala Ala Gly Ile
                885                 890                 895

Phe Asp Gln Tyr Thr Lys Thr Lys Ser Ser Pro Thr Gly Asn Arg Gly
                900                 905                 910

Ala Lys Phe Ser Phe Glu Asp Gly Glu Ala Ala Tyr Thr His Asn
                915                 920                 925

Val Asp Thr Val Thr Thr Thr Thr Gly Ser Gln Gly Ala Thr Asp Gly
                930                 935                 940

Ser Lys Ala Leu Gln Ala Glu Phe Thr Ser Phe Thr Ala Phe Ala Trp
945                 950                 955                 960
```

```
Asp Thr Thr Gly Thr Tyr Ser Gly Ser Leu Asp Phe Thr Ala Pro Glu
            965                 970                 975

Glu Gly Trp Ser Leu Gly Thr Thr Pro Ile Thr Phe Asp Val Thr Asn
            980                 985                 990

Leu Arg Ser Tyr Ala Thr Gln Leu Arg Val Glu Val Thr Asp Thr Ser
            995                 1000                1005

Asp Val Lys Gly Thr Tyr Tyr Phe Thr Leu Gly Ala Asp Ala Ser
        1010                1015                1020

Arg Ser Ile Ser Ile Ala Asp Phe Gly Ile Ala Gly Gly Thr Trp
        1025                1030                1035

Leu Ala Asp Gly Asn Phe Pro Arg Asn Ala Ala Ile Asp Thr Glu
        1040                1045                1050

Asn Leu Lys Ser Ile Arg Leu Phe Val Phe Ser Pro Thr Ala Ala
        1055                1060                1065

Pro Val Thr Asn Ala Ala Leu Ala Ile Asp His Ile Ile Ile Gly
        1070                1075                1080

Ser Ala Ser Asp Pro Gly Pro Gly Pro Gly Asn Pro Asn Gly Val
        1085                1090                1095

Phe Leu Ser Phe Glu Asp Gln Glu Glu Val Val Tyr Thr Thr Asn
        1100                1105                1110

Gly Gln Asp Ile Thr Val Thr Arg Ser Glu Gln Gly Ala Thr His
        1115                1120                1125

Gly Ser Lys Ala Leu His Ala Glu Phe Asp Ser Phe Thr Ala Tyr
        1130                1135                1140

Asp Trp Asp Thr Ser Gly Lys Tyr Ser Gly Asn Ile Asp Phe Thr
        1145                1150                1155

Ala Pro Glu Gly Gly Trp Ser Leu Gly Ser Lys Pro Leu Gln Leu
        1160                1165                1170

Asp Val Thr Asn Leu Val Asn Thr Gly Ala Gln Leu Arg Val Glu
        1175                1180                1185

Val Thr Asp Val Glu Asn His Arg Gly Ile Tyr Tyr Phe Ala Ile
        1190                1195                1200

Ala Pro Asn Gln Ala Arg Thr Leu Thr Ile Ser Asp Phe Gly Ile
        1205                1210                1215

Ser Ala Ala Ser Trp Leu Ala Asp Gly Tyr Phe Ala Lys Ala Ala
        1220                1225                1230

Ala Ile Asp Thr Thr Lys Leu Lys Ser Ile Arg Leu Tyr Val Phe
        1235                1240                1245

Glu Pro Thr Ala Ile Thr Val Gly His Ala Ala Leu Ala Phe Asp
        1250                1255                1260

Ser Leu Ile Ile Gly Asn Glu Pro Ile Gln Pro Thr Glu Glu Gln
        1265                1270                1275

Leu Ala Ala Glu Ala Ala Asn Ala Leu Thr Ala Ala Ser Leu Thr
        1280                1285                1290

Phe Ala Ala Gly Asp Met Ala Gln Ala Val Thr Asn His Ile Ser
        1295                1300                1305

Leu Pro Ser Ala Gly Leu His Gly Ala Ser Leu Thr Trp Ala Ser
        1310                1315                1320

Ser His Pro Ser Thr Val Ala Thr Asp Gly Thr Val Thr Arg Pro
        1325                1330                1335

Gln His Gly Ser Gly Asn Gln Val Val Leu Thr Ala Thr Val
        1340                1345                1350
```

-continued

Met Ile Gly Ala Ala Ser Ser Thr Lys Ala Ile Glu Val Thr Val
1355             1360             1365

Leu Gln Gln Ala Ser Thr Ser Asn Pro Pro Gly Gly Asn Glu Asn
1370             1375             1380

Pro Ser His Pro Glu Pro Ser Ser Pro Pro Glu Val His Val Asp
1385             1390             1395

Ile Leu Val Asp Gly Lys Lys Gln Asp Lys Ile Ala Ser Ser Val
1400             1405             1410

Thr Thr Thr Glu Ala Gly Arg Thr Val Thr Thr Ile Thr Val Asp
1415             1420             1425

Gln Gln Leu Leu Lys Asn Ser Leu Ser Asn Met Ala Asn Asn Gly
1430             1435             1440

Ile Ile Thr Ile Pro Val Ser Ser Gly Ser Asp Val Val Asn Gly
1445             1450             1455

Lys Leu Asn Gly Gln Ile Val Lys Asp Leu Gln Gln Lys Asn Ala
1460             1465             1470

Phe Phe Glu Leu Arg Thr Gly Thr Phe Ser Tyr Lys Leu Pro Ile
1475             1480             1485

Lys Gln Ile Asn Ile Asn Glu Ile Ala Lys Gly Leu Gly Ser Asp
1490             1495             1500

Val Lys Leu Glu Asp Ile Thr Leu Asp Leu Thr Ile Ser Gln Val
1505             1510             1515

Asp Ala Gly Thr Gln Gln Val Leu Glu Asn Ser Ala Lys Gln Gly
1520             1525             1530

Gly Phe Thr Val Val Ala Pro Pro Val Asp Phe His Ile Thr Tyr
1535             1540             1545

Thr Tyr Gln Gly Ala Thr Val Glu Phe Arg Thr Phe Asn Thr Phe
1550             1555             1560

Val Glu Arg Ala Val Ile Ile Pro Asp Gly Val Asp Pro Thr Gln
1565             1570             1575

Ile Thr Thr Gly Val Val Met Glu Ala Asp Gly Thr Val Arg Gln
1580             1585             1590

Ile Pro Thr Arg Leu Val Arg Val Asn Gly Ser Tyr His Ala Val
1595             1600             1605

Met Asn Ser Met Thr Asn Ser Thr Tyr Ala Ile Ile Trp Asn Pro
1610             1615             1620

Ala Ala Phe Gln Asp Val Ser Gly His Trp Val Glu Glu Ala Val
1625             1630             1635

Asn Asp Leu Gly Ser Arg Leu Val Ile Ser Gly Val Asp Gly Asn
1640             1645             1650

Arg Phe Glu Pro Asp Arg Ser Ile Thr Arg Ala Glu Phe Thr Ala
1655             1660             1665

Ile Leu Val Arg Ala Leu Gly Leu Arg Ala Glu Ser Gly Glu Pro
1670             1675             1680

Ala Tyr Ser Asp Val Ala Lys Gly Val Trp Tyr Glu Gly Tyr Leu
1685             1690             1695

Asn Thr Ala Thr Lys Tyr Asp Leu Ile Asn Gly Tyr Ala Asn Gly
1700             1705             1710

Gln Phe Gly Ala Asn Asp Leu Ile Thr Arg Glu Gln Val Met Ser
1715             1720             1725

Ile Met Glu Arg Ala Met Ala Leu Thr Gly Leu Asp Ser Ala Ala
1730             1735             1740

Glu Met Ala Glu Ala Asp Glu Leu Leu Ser Ser Phe Lys Asp Gly

```
                    1745                1750                1755

Ser Glu Ala Ala Ala Tyr Ala Lys Ser Gly Ile Ala Ala Ser Ile
              1760                1765                1770

Lys Ala Gly Leu Val Leu Gly Arg Ser Glu Gln Val Leu Ala Pro
        1775                1780                1785

Lys Ala Ala Ile Thr Arg Ala Glu Val Ala Glu Val Val Arg Arg
        1790                1795                1800

Leu Leu Glu Lys Ser Asp Leu Ile
        1805                1810

<210> SEQ ID NO 2
<211> LENGTH: 1380
<212> TYPE: PRT
<213> ORGANISM: Paenibacillus agarexedens

<400> SEQUENCE: 2

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45

Ile Gln Arg Ile Asn Phe Leu Gln Phe Pro Asp Gly Gln Tyr Leu Gln
50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Ser Val Ala Gln Thr
                85                  90                  95

Met Glu Leu Tyr Val Ile Asp Pro Asn Gly Val Glu Thr His Trp Thr
            100                 105                 110

Val Phe Gln Asn Gly Gly Trp Lys Asp Gly Ile Thr Gly Leu Tyr Thr
        115                 120                 125

Asn Tyr Thr Lys Met Gly Phe Gln Glu Asp Asn Pro Thr Glu Gly Ile
    130                 135                 140

Thr His Pro Trp Leu Ile Lys Gly Thr Asn Gly Asp Ile Ile Tyr Glu
145                 150                 155                 160

Gly Tyr Lys Met Lys Ile Val Gly Asn Gly Thr Leu Arg Ser Val Tyr
                165                 170                 175

His Trp Glu Glu Glu Gly Val Pro Leu Glu Phe Asp Thr Ser Ala Trp
            180                 185                 190

Thr Val Leu Gly Gly Asp Lys Asp Ile Leu Asn Val Ser Val Asn Val
        195                 200                 205

Asp Ala Leu Thr Asn Leu Ser Met Asp Gly Val Asp Lys Leu Pro Glu
    210                 215                 220

Glu Val Phe Lys Arg Tyr His Val Asn Ser Gly Pro Ile Gly Leu Glu
225                 230                 235                 240

Gln Ala Gly Gly Glu Phe Thr Val Leu Asp Glu Ala Tyr His Arg Thr
                245                 250                 255

Thr His Asp Tyr Gly Phe Thr Pro Gly Arg Gly Ala Phe His Tyr Asn
            260                 265                 270

Leu Leu Thr Ser Trp Ala Gly Leu Lys Glu Asp Pro Ala Arg Pro Gly
        275                 280                 285

Tyr Ala Asp Phe Thr Ala Thr Asn Glu Val Tyr Ala Lys Ser Gln Pro
    290                 295                 300
```

```
Ala Ile Asp Lys Phe Glu Ser Leu Tyr Pro Ser Ile Gly Lys Asp Tyr
305                 310                 315                 320

Val Leu Thr Leu Asp Gly Trp Pro Arg Trp Met Trp Glu Ser Pro Asn
            325                 330                 335

Ser Gly Gln Ser Glu His Phe Gly Thr Pro Ser Arg Ala Asn Phe Asp
        340                 345                 350

Ala Ala Ala Asp Ala Ser Ala Lys Leu Ile Lys Ser Ile Asp Thr Arg
    355                 360                 365

Phe Asp Gly Leu Gly Pro Lys Tyr Val Glu Val Lys Asn Glu Ser Thr
370                 375                 380

Ile Pro Gln Glu Trp Trp Phe Gln Ser Glu Pro Glu Gln Ala Trp
385                 390                 395                 400

Ser Tyr Leu Ser Glu Phe His Asn Lys Val Ala Ala Glu Val Lys Ala
            405                 410                 415

Glu Asn Pro Asp Val Leu Val Gly Gly Pro Ser Ser Ala Phe Met Tyr
        420                 425                 430

Leu Glu Lys Asn Asp Phe Asp Glu Ala Arg Ala Gln Leu Lys Phe Met
    435                 440                 445

Asp Asp Thr Lys Asp Ser Leu Asp Trp Tyr Ser His His Phe Tyr Glu
450                 455                 460

Asn Ala Asn Leu Phe Ile His Asp Arg Glu Asn Asn Ser Asp Gly Phe
465                 470                 475                 480

Leu Ser Gly Arg Met Glu Ala Val Leu Asp Leu Leu Asn Ala His Met
            485                 490                 495

Ala Asn Thr Asp Asn Val Lys Pro Ile Tyr Ile Thr Glu Gly Thr
        500                 505                 510

Tyr Asn Thr Ala Gly Ser Asp Ala Asp Tyr Phe Gln Lys Leu Val Ala
    515                 520                 525

Phe Asn Gly Tyr Met Leu Arg Phe Ile Asn Tyr Ser Asp Thr Ile Gly
530                 535                 540

Met Leu Val Pro Tyr Leu Tyr Pro Ile Ile Asn Trp Arg Pro Asn Ser
545                 550                 555                 560

Thr Gly Thr Phe Tyr Lys Tyr Asn Glu Thr Gln Asn Gly Leu Leu Glu
            565                 570                 575

Glu Met Thr Pro Met Glu Ala Tyr Leu Asp Met Trp Lys Asp Tyr Arg
        580                 585                 590

Gly Ala Phe Leu Pro Ser Glu Ala Asp Gln Glu Arg Val Phe Thr Asn
    595                 600                 605

Ala Val Arg Tyr Asn Asp Lys Val Tyr Val Ala Val His Asn Leu Asn
610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
            645                 650                 655

Thr Tyr Glu Gln Lys Asn Val Ala Asp Leu Asn Asn Val Tyr Met Arg
        660                 665                 670

Val Gln Glu Met Ser Val Phe Glu Ile Thr Leu Asp Ser Asn Pro Pro
    675                 680                 685

Phe Thr Lys Thr Trp Glu Arg Glu Phe Ala Tyr Ala Pro Gln Glu Leu
690                 695                 700

Val Pro Thr Ser Val Asn Ala Pro Ala Ser Phe Thr Val Gln Ala Arg
705                 710                 715                 720

Pro Ala Asp Leu Ala Lys Ala Thr Leu Arg Ile Gly Phe Gly Lys Thr
```

-continued

```
                725                 730                 735
Gly Ser Gly Phe Ala Glu Asp Met Gln Val Val Asn Ser Gly Asp
            740                 745                 750
Thr Ala Asn Met Gln Ser Phe Ser Lys Asp Leu Ala Tyr Thr Asp Lys
        755                 760                 765
Pro Gly Asn Leu Leu Thr Phe Ala Glu Phe Glu Leu Asp Thr Ser Lys
    770                 775                 780
Leu Leu Thr Ser Asn Thr Ile Glu Ile Thr Leu Pro Asp Asp Gly
785                 790                 795             800
Tyr Ile Thr Ser Val Gln Ile Ile Glu Tyr His Glu Gln Pro Ala Pro
                805                 810                 815
Thr Gly Ile Ala Thr Ser Ala Leu Ala Ala Pro Val Ala Asp Ala Lys
            820                 825                 830
Ser Lys Leu Ala Ser Thr Ile Ile Ser Ser Thr Gly Asn Glu Val Glu
        835                 840                 845
Pro Gly Gln Lys Trp Val Lys Lys His Ile Arg Asp Thr Leu Asn Ile
    850                 855                 860
Glu Val Ala Lys Ala Glu Val Val Ala Gln Asp Ala Leu Ala Thr Asn
865                 870                 875                 880
Asp Glu Ile Thr Lys Ala Leu Glu Asp Leu Thr Lys Ala Ala Gly Ile
                885                 890                 895
Phe Asp Gln Tyr Thr Lys Thr Lys Ser Ser Pro Thr Gly Asn Arg Gly
            900                 905                 910
Ala Lys Phe Ser Phe Glu Asp Gly Glu Glu Ala Ala Tyr Thr His Asn
        915                 920                 925
Val Asp Thr Val Thr Thr Thr Gly Ser Gln Gly Ala Thr Asp Gly
    930                 935                 940
Ser Lys Ala Leu Gln Ala Glu Phe Thr Ser Phe Thr Ala Phe Ala Trp
945                 950                 955                 960
Asp Thr Thr Gly Thr Tyr Ser Gly Ser Leu Asp Phe Thr Ala Pro Glu
                965                 970                 975
Glu Gly Trp Ser Leu Gly Thr Thr Pro Ile Thr Phe Asp Val Thr Asn
            980                 985                 990
Leu Arg Ser Tyr Ala Thr Gln Leu Arg Val Glu Val Thr Asp Thr Ser
        995                 1000                1005
Asp Val Lys Gly Thr Tyr Tyr Phe Thr Leu Gly Ala Asp Ala Ser
    1010                1015                1020
Arg Ser Ile Ser Ile Ala Asp Phe Gly Ile Ala Gly Gly Thr Trp
    1025                1030                1035
Leu Ala Asp Gly Asn Phe Pro Arg Asn Ala Ala Ile Asp Thr Glu
    1040                1045                1050
Asn Leu Lys Ser Ile Arg Leu Phe Val Phe Ser Pro Thr Ala Ala
    1055                1060                1065
Pro Val Thr Asn Ala Ala Leu Ala Ile Asp His Ile Ile Ile Gly
    1070                1075                1080
Ser Ala Ser Asp Pro Gly Pro Gly Pro Gly Asn Pro Asn Gly Val
    1085                1090                1095
Phe Leu Ser Phe Glu Asp Gln Glu Glu Val Val Tyr Thr Thr Asn
    1100                1105                1110
Gly Gln Asp Ile Thr Val Thr Arg Ser Glu Gln Gly Ala Thr His
    1115                1120                1125
Gly Ser Lys Ala Leu His Ala Glu Phe Asp Ser Phe Thr Ala Tyr
    1130                1135                1140
```

Asp Trp Asp Thr Ser Gly Lys Tyr Ser Gly Asn Ile Asp Phe Thr
1145                1150                1155

Ala Pro Glu Gly Gly Trp Ser Leu Gly Ser Lys Pro Leu Gln Leu
1160                1165                1170

Asp Val Thr Asn Leu Val Asn Thr Gly Ala Gln Leu Arg Val Glu
1175                1180                1185

Val Thr Asp Val Glu Asn His Arg Gly Ile Tyr Tyr Phe Ala Ile
1190                1195                1200

Ala Pro Asn Gln Ala Arg Thr Leu Thr Ile Ser Asp Phe Gly Ile
1205                1210                1215

Ser Ala Ala Ser Trp Leu Ala Asp Gly Tyr Phe Ala Lys Ala Ala
1220                1225                1230

Ala Ile Asp Thr Thr Lys Leu Lys Ser Ile Arg Leu Tyr Val Phe
1235                1240                1245

Glu Pro Thr Ala Ile Thr Val Gly His Ala Ala Leu Ala Phe Asp
1250                1255                1260

Ser Leu Ile Ile Gly Asn Glu Pro Ile Gln Pro Thr Glu Glu Gln
1265                1270                1275

Leu Ala Ala Glu Ala Ala Asn Ala Leu Thr Ala Ala Ser Leu Thr
1280                1285                1290

Phe Ala Ala Gly Asp Met Ala Gln Ala Val Thr Asn His Ile Ser
1295                1300                1305

Leu Pro Ser Ala Gly Leu His Gly Ala Ser Leu Thr Trp Ala Ser
1310                1315                1320

Ser His Pro Ser Thr Val Ala Thr Asp Gly Thr Val Thr Arg Pro
1325                1330                1335

Gln His Gly Ser Gly Asn Gln Val Val Thr Leu Thr Ala Thr Val
1340                1345                1350

Met Ile Gly Ala Ala Ser Ser Thr Lys Ala Ile Glu Val Thr Val
1355                1360                1365

Leu Gln Gln Ala Ser Thr Ser Asn Pro Pro Gly Gly
1370                1375                1380

<210> SEQ ID NO 3
<211> LENGTH: 1275
<212> TYPE: PRT
<213> ORGANISM: Paenibacillus agarexedens

<400> SEQUENCE: 3

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
                20                  25                  30

Gly Asp Asn Ala Val Ala Tyr Phe Asn Ser Ile Asn Gly Glu Ser Arg
            35                  40                  45

Ile Gln Arg Ile Asn Phe Leu Gln Phe Pro Asp Gly Gln Tyr Leu Gln
        50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Gly Ser Val Ala Gln Thr
                85                  90                  95

Met Glu Leu Tyr Val Ile Asp Pro Asn Gly Val Glu Thr His Trp Thr
                100                 105                 110

Val Phe Gln Asn Gly Gly Trp Lys Asp Gly Ile Thr Gly Leu Tyr Thr

-continued

```
            115                 120                 125
Asn Tyr Thr Lys Met Gly Phe Gln Glu Asp Asn Pro Thr Glu Gly Ile
130                 135                 140

Thr His Pro Trp Leu Ile Lys Gly Thr Asn Gly Asp Ile Ile Tyr Glu
145                 150                 155                 160

Gly Tyr Lys Met Lys Ile Val Gly Asn Gly Thr Leu Arg Ser Val Tyr
                    165                 170                 175

His Trp Glu Glu Gly Val Pro Leu Glu Phe Asp Thr Ser Ala Trp
                180                 185                 190

Thr Val Leu Gly Gly Asp Lys Asp Ile Leu Asn Val Ser Val Asn Val
            195                 200                 205

Asp Ala Leu Thr Asn Leu Ser Met Asp Gly Val Asp Lys Leu Pro Glu
210                 215                 220

Glu Val Phe Lys Arg Tyr His Val Asn Ser Gly Pro Ile Gly Leu Glu
225                 230                 235                 240

Gln Ala Gly Gly Glu Phe Thr Val Leu Asp Glu Ala Tyr His Arg Thr
                    245                 250                 255

Thr His Asp Tyr Gly Phe Thr Pro Gly Arg Gly Ala Phe His Tyr Asn
                260                 265                 270

Leu Leu Thr Ser Trp Ala Gly Leu Lys Glu Asp Pro Ala Arg Pro Gly
            275                 280                 285

Tyr Ala Asp Phe Thr Ala Thr Asn Glu Val Tyr Ala Lys Ser Gln Pro
290                 295                 300

Ala Ile Asp Lys Phe Glu Ser Leu Tyr Pro Ser Ile Gly Lys Asp Tyr
305                 310                 315                 320

Val Leu Thr Leu Asp Gly Trp Pro Arg Trp Met Trp Glu Ser Pro Asn
                    325                 330                 335

Ser Gly Gln Ser Glu His Phe Gly Thr Pro Ser Arg Ala Asn Phe Asp
                340                 345                 350

Ala Ala Ala Asp Ala Ser Ala Lys Leu Ile Lys Ser Ile Asp Thr Arg
            355                 360                 365

Phe Asp Gly Leu Gly Pro Lys Tyr Val Glu Val Lys Asn Glu Ser Thr
370                 375                 380

Ile Pro Gln Glu Trp Trp Phe Phe Gln Ser Glu Pro Glu Gln Ala Trp
385                 390                 395                 400

Ser Tyr Leu Ser Glu Phe His Asn Lys Val Ala Ala Glu Val Lys Ala
                    405                 410                 415

Glu Asn Pro Asp Val Leu Val Gly Gly Pro Ser Ser Ala Phe Met Tyr
                420                 425                 430

Leu Glu Lys Asn Asp Phe Asp Glu Ala Arg Ala Gln Leu Lys Phe Met
            435                 440                 445

Asp Asp Thr Lys Asp Ser Leu Asp Trp Tyr Ser His His Phe Tyr Glu
450                 455                 460

Asn Ala Asn Leu Phe Ile His Asp Arg Glu Asn Asn Ser Asp Gly Phe
465                 470                 475                 480

Leu Ser Gly Arg Met Glu Ala Val Leu Asp Leu Leu Asn Ala His Met
                    485                 490                 495

Ala Asn Thr Asp Asn Val Lys Pro Ile Tyr Ile Thr Glu Glu Gly Thr
                500                 505                 510

Tyr Asn Thr Ala Gly Ser Asp Ala Asp Tyr Phe Gln Lys Leu Val Ala
            515                 520                 525

Phe Asn Gly Tyr Met Leu Arg Phe Ile Asn Tyr Ser Asp Thr Ile Gly
530                 535                 540
```

```
Met Leu Val Pro Tyr Leu Tyr Pro Ile Ile Asn Trp Arg Pro Asn Ser
545                 550                 555                 560

Thr Gly Thr Phe Tyr Lys Tyr Asn Glu Thr Gln Asn Gly Leu Leu Glu
                565                 570                 575

Glu Met Thr Pro Met Glu Ala Tyr Leu Asp Met Trp Lys Asp Tyr Arg
            580                 585                 590

Gly Ala Phe Leu Pro Ser Glu Ala Asp Gln Glu Arg Val Phe Thr Asn
        595                 600                 605

Ala Val Arg Tyr Asn Asp Lys Val Tyr Val Ala Val His Asn Leu Asn
610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
                645                 650                 655

Thr Tyr Glu Gln Lys Asn Val Ala Asp Leu Asn Asn Val Tyr Met Arg
            660                 665                 670

Val Gln Glu Met Ser Val Phe Glu Ile Thr Leu Asp Ser Asn Pro Pro
        675                 680                 685

Phe Thr Lys Thr Trp Glu Arg Glu Phe Ala Tyr Ala Pro Gln Glu Leu
690                 695                 700

Val Pro Thr Ser Val Asn Ala Pro Ala Ser Phe Thr Val Gln Ala Arg
705                 710                 715                 720

Pro Ala Asp Leu Ala Lys Ala Thr Leu Arg Ile Gly Phe Gly Lys Thr
                725                 730                 735

Gly Ser Gly Phe Ala Glu Asp Met Gln Val Val Asn Ser Gly Asp
            740                 745                 750

Thr Ala Asn Met Gln Ser Phe Ser Lys Asp Leu Ala Tyr Thr Asp Lys
            755                 760                 765

Pro Gly Asn Leu Leu Thr Phe Ala Glu Phe Glu Leu Asp Thr Ser Lys
        770                 775                 780

Leu Leu Thr Ser Asn Thr Ile Glu Ile Thr Leu Pro Asp Asp Asp Gly
785                 790                 795                 800

Tyr Ile Thr Ser Val Gln Ile Ile Glu Tyr His Glu Gln Pro Ala Pro
                805                 810                 815

Thr Gly Ile Ala Thr Ser Ala Leu Ala Ala Pro Val Ala Asp Ala Lys
            820                 825                 830

Ser Lys Leu Ala Ser Thr Ile Ile Ser Ser Thr Gly Asn Glu Val Glu
        835                 840                 845

Pro Gly Gln Lys Trp Val Lys Lys His Ile Arg Asp Thr Leu Asn Ile
        850                 855                 860

Glu Val Ala Lys Ala Glu Val Val Ala Gln Asp Ala Leu Ala Thr Asn
865                 870                 875                 880

Asp Glu Ile Thr Lys Ala Leu Glu Asp Leu Thr Lys Ala Ala Gly Ile
                885                 890                 895

Phe Asp Gln Tyr Thr Lys Thr Lys Ser Ser Pro Thr Gly Asn Arg Gly
            900                 905                 910

Ala Lys Phe Ser Phe Glu Asp Gly Glu Glu Ala Ala Tyr Thr His Asn
        915                 920                 925

Val Asp Thr Val Thr Thr Thr Gly Ser Gln Gly Ala Thr Asp Gly
            930                 935                 940

Ser Lys Ala Leu Gln Ala Glu Phe Thr Ser Phe Thr Ala Phe Ala Trp
945                 950                 955                 960
```

```
Asp Thr Thr Gly Thr Tyr Ser Gly Ser Leu Asp Phe Thr Ala Pro Glu
            965                 970                 975

Glu Gly Trp Ser Leu Gly Thr Thr Pro Ile Thr Phe Asp Val Thr Asn
        980                 985                 990

Leu Arg Ser Tyr Ala Thr Gln Leu Arg Val Glu Val Thr Asp Thr Ser
            995                 1000                1005

Asp Val Lys Gly Thr Tyr Tyr Phe Thr Leu Gly Ala Asp Ala Ser
    1010                1015                1020

Arg Ser Ile Ser Ile Ala Asp Phe Gly Ile Ala Gly Gly Thr Trp
    1025                1030                1035

Leu Ala Asp Gly Asn Phe Pro Arg Asn Ala Ala Ile Asp Thr Glu
    1040                1045                1050

Asn Leu Lys Ser Ile Arg Leu Phe Val Phe Ser Pro Thr Ala Ala
    1055                1060                1065

Pro Val Thr Asn Ala Ala Leu Ala Ile Asp His Ile Ile Ile Gly
    1070                1075                1080

Ser Ala Ser Asp Pro Gly Pro Gly Pro Gly Asn Pro Asn Gly Val
    1085                1090                1095

Phe Leu Ser Phe Glu Asp Gln Glu Glu Val Val Tyr Thr Thr Asn
    1100                1105                1110

Gly Gln Asp Ile Thr Val Thr Arg Ser Glu Gln Gly Ala Thr His
    1115                1120                1125

Gly Ser Lys Ala Leu His Ala Glu Phe Asp Ser Phe Thr Ala Tyr
    1130                1135                1140

Asp Trp Asp Thr Ser Gly Lys Tyr Ser Gly Asn Ile Asp Phe Thr
    1145                1150                1155

Ala Pro Glu Gly Gly Trp Ser Leu Gly Ser Lys Pro Leu Gln Leu
    1160                1165                1170

Asp Val Thr Asn Leu Val Asn Thr Gly Ala Gln Leu Arg Val Glu
    1175                1180                1185

Val Thr Asp Val Glu Asn His Arg Gly Ile Tyr Tyr Phe Ala Ile
    1190                1195                1200

Ala Pro Asn Gln Ala Arg Thr Leu Thr Ile Ser Asp Phe Gly Ile
    1205                1210                1215

Ser Ala Ala Ser Trp Leu Ala Asp Gly Tyr Phe Ala Lys Ala Ala
    1220                1225                1230

Ala Ile Asp Thr Thr Lys Leu Lys Ser Ile Arg Leu Tyr Val Phe
    1235                1240                1245

Glu Pro Thr Ala Ile Thr Val Gly His Ala Ala Leu Ala Phe Asp
    1250                1255                1260

Ser Leu Ile Ile Gly Asn Glu Pro Ile Gln Pro Thr
    1265                1270                1275

<210> SEQ ID NO 4
<211> LENGTH: 1096
<212> TYPE: PRT
<213> ORGANISM: Paenibacillus agarexedens

<400> SEQUENCE: 4

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45
```

-continued

```
Ile Gln Arg Ile Asn Phe Leu Gln Phe Pro Asp Gly Gln Tyr Leu Gln
    50                      55                  60
Ile Asn Gly Glu Val Thr Phe Asp Ile Pro Ala Met Asp Ala Arg Val
65                      70                  75                  80
Trp Arg Leu Phe Gly Asp Val Arg Phe Glu Gly Ser Val Ala Gln Thr
                85                  90                  95
Met Glu Leu Tyr Val Ile Asp Pro Asn Gly Val Glu Thr His Trp Thr
                100                 105                 110
Val Phe Gln Asn Gly Gly Trp Lys Asp Gly Ile Thr Gly Leu Tyr Thr
            115                 120                 125
Asn Tyr Thr Lys Met Gly Phe Gln Glu Asp Asn Pro Thr Glu Gly Ile
    130                 135                 140
Thr His Pro Trp Leu Ile Lys Gly Thr Asn Gly Asp Ile Ile Tyr Glu
145                 150                 155                 160
Gly Tyr Lys Met Lys Ile Val Gly Asn Gly Thr Leu Arg Ser Val Tyr
                165                 170                 175
His Trp Glu Glu Gly Val Pro Leu Glu Phe Asp Thr Ser Ala Trp
            180                 185                 190
Thr Val Leu Gly Gly Asp Lys Asp Ile Leu Asn Val Ser Val Asn Val
    195                 200                 205
Asp Ala Leu Thr Asn Leu Ser Met Asp Gly Val Asp Lys Leu Pro Glu
    210                 215                 220
Glu Val Phe Lys Arg Tyr His Val Asn Ser Gly Pro Ile Gly Leu Glu
225                 230                 235                 240
Gln Ala Gly Gly Glu Phe Thr Val Leu Asp Glu Ala Tyr His Arg Thr
                245                 250                 255
Thr His Asp Tyr Gly Phe Thr Pro Gly Arg Gly Ala Phe His Tyr Asn
            260                 265                 270
Leu Leu Thr Ser Trp Ala Gly Leu Lys Glu Asp Pro Ala Arg Pro Gly
    275                 280                 285
Tyr Ala Asp Phe Thr Ala Thr Asn Glu Val Tyr Ala Lys Ser Gln Pro
    290                 295                 300
Ala Ile Asp Lys Phe Glu Ser Leu Tyr Pro Ser Ile Gly Lys Asp Tyr
305                 310                 315                 320
Val Leu Thr Leu Asp Gly Trp Pro Arg Trp Met Trp Glu Ser Pro Asn
                325                 330                 335
Ser Gly Gln Ser Glu His Phe Gly Thr Pro Ser Arg Ala Asn Phe Asp
            340                 345                 350
Ala Ala Ala Asp Ala Ser Ala Lys Leu Ile Lys Ser Ile Asp Thr Arg
    355                 360                 365
Phe Asp Gly Leu Gly Pro Lys Tyr Val Glu Val Lys Asn Glu Ser Thr
    370                 375                 380
Ile Pro Gln Glu Trp Trp Phe Phe Gln Ser Glu Pro Glu Gln Ala Trp
385                 390                 395                 400
Ser Tyr Leu Ser Glu Phe His Asn Lys Val Ala Ala Glu Val Lys Ala
                405                 410                 415
Glu Asn Pro Asp Val Leu Val Gly Gly Pro Ser Ser Ala Phe Met Tyr
            420                 425                 430
Leu Glu Lys Asn Asp Phe Asp Glu Ala Arg Ala Gln Leu Lys Phe Met
    435                 440                 445
Asp Asp Thr Lys Asp Ser Leu Asp Trp Tyr Ser His Phe Tyr Glu
    450                 455                 460
```

```
Asn Ala Asn Leu Phe Ile His Asp Arg Glu Asn Ser Asp Gly Phe
465                 470                 475                 480

Leu Ser Gly Arg Met Glu Ala Val Leu Asp Leu Leu Asn Ala His Met
            485                 490                 495

Ala Asn Thr Asp Asn Val Lys Pro Ile Tyr Ile Thr Glu Glu Gly Thr
            500                 505                 510

Tyr Asn Thr Ala Gly Ser Asp Ala Asp Tyr Phe Gln Lys Leu Val Ala
            515                 520                 525

Phe Asn Gly Tyr Met Leu Arg Phe Ile Asn Tyr Ser Asp Thr Ile Gly
            530                 535                 540

Met Leu Val Pro Tyr Leu Tyr Pro Ile Ile Asn Trp Arg Pro Asn Ser
545                 550                 555                 560

Thr Gly Thr Phe Tyr Lys Tyr Asn Glu Thr Gln Asn Gly Leu Leu Glu
                565                 570                 575

Glu Met Thr Pro Met Glu Ala Tyr Leu Asp Met Trp Lys Asp Tyr Arg
                580                 585                 590

Gly Ala Phe Leu Pro Ser Glu Ala Asp Gln Glu Arg Val Phe Thr Asn
                595                 600                 605

Ala Val Arg Tyr Asn Asp Lys Val Tyr Val Ala Val His Asn Leu Asn
            610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
                645                 650                 655

Thr Tyr Glu Gln Lys Asn Val Ala Asp Leu Asn Asn Val Tyr Met Arg
                660                 665                 670

Val Gln Glu Met Ser Val Phe Glu Ile Thr Leu Asp Ser Asn Pro Pro
            675                 680                 685

Phe Thr Lys Thr Trp Glu Arg Glu Phe Ala Tyr Ala Pro Gln Glu Leu
            690                 695                 700

Val Pro Thr Ser Val Asn Ala Pro Ala Ser Phe Thr Val Gln Ala Arg
705                 710                 715                 720

Pro Ala Asp Leu Ala Lys Ala Thr Leu Arg Ile Gly Phe Gly Lys Thr
                725                 730                 735

Gly Ser Gly Phe Ala Glu Asp Met Gln Val Val Asn Ser Gly Asp
                740                 745                 750

Thr Ala Asn Met Gln Ser Phe Ser Lys Asp Leu Ala Tyr Thr Asp Lys
            755                 760                 765

Pro Gly Asn Leu Leu Thr Phe Ala Glu Phe Glu Leu Asp Thr Ser Lys
            770                 775                 780

Leu Leu Thr Ser Asn Thr Ile Glu Ile Thr Leu Pro Asp Asp Gly
785                 790                 795                 800

Tyr Ile Thr Ser Val Gln Ile Ile Glu Tyr His Glu Gln Pro Ala Pro
                805                 810                 815

Thr Gly Ile Ala Thr Ser Ala Leu Ala Ala Pro Val Ala Asp Ala Lys
                820                 825                 830

Ser Lys Leu Ala Ser Thr Ile Ile Ser Ser Thr Gly Asn Glu Val Glu
            835                 840                 845

Pro Gly Gln Lys Trp Val Lys Lys His Ile Arg Asp Thr Leu Asn Ile
            850                 855                 860

Glu Val Ala Lys Ala Glu Val Val Ala Gln Asp Ala Leu Ala Thr Asn
865                 870                 875                 880

Asp Glu Ile Thr Lys Ala Leu Glu Asp Leu Thr Lys Ala Ala Gly Ile
```

-continued

```
                    885                 890                 895
Phe Asp Gln Tyr Thr Lys Thr Lys Ser Ser Pro Thr Gly Asn Arg Gly
                900                 905                 910

Ala Lys Phe Ser Phe Glu Asp Gly Glu Ala Ala Tyr Thr His Asn
            915                 920                 925

Val Asp Thr Val Thr Thr Thr Gly Ser Gln Gly Ala Thr Asp Gly
    930                 935                 940

Ser Lys Ala Leu Gln Ala Glu Phe Thr Ser Phe Thr Ala Phe Ala Trp
945                 950                 955                 960

Asp Thr Thr Gly Thr Tyr Ser Gly Ser Leu Asp Phe Thr Ala Pro Glu
                965                 970                 975

Glu Gly Trp Ser Leu Gly Thr Thr Pro Ile Thr Phe Asp Val Thr Asn
                980                 985                 990

Leu Arg Ser Tyr Ala Thr Gln Leu Arg Val Glu Val Thr Asp Thr Ser
                995                 1000                1005

Asp Val Lys Gly Thr Tyr Tyr Phe Thr Leu Gly Ala Asp Ala Ser
        1010                1015                1020

Arg Ser Ile Ser Ile Ala Asp Phe Gly Ile Ala Gly Gly Thr Trp
        1025                1030                1035

Leu Ala Asp Gly Asn Phe Pro Arg Asn Ala Ala Ile Asp Thr Glu
        1040                1045                1050

Asn Leu Lys Ser Ile Arg Leu Phe Val Phe Ser Pro Thr Ala Ala
        1055                1060                1065

Pro Val Thr Asn Ala Ala Leu Ala Ile Asp His Ile Ile Ile Gly
        1070                1075                1080

Ser Ala Ser Asp Pro Gly Pro Gly Pro Gly Asn Pro Asn
        1085                1090                1095

<210> SEQ ID NO 5
<211> LENGTH: 975
<212> TYPE: PRT
<213> ORGANISM: Paenibacillus agarexedens

<400> SEQUENCE: 5

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45

Ile Gln Arg Ile Asn Phe Leu Gln Phe Pro Asp Gly Gln Tyr Leu Gln
    50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Gly Ser Val Ala Gln Thr
                85                  90                  95

Met Glu Leu Tyr Val Ile Asp Pro Asn Gly Val Glu Thr His Trp Thr
                100                 105                 110

Val Phe Gln Asn Gly Gly Trp Lys Asp Gly Ile Thr Gly Leu Tyr Thr
            115                 120                 125

Asn Tyr Thr Lys Met Gly Phe Gln Glu Asp Asn Pro Thr Glu Gly Ile
        130                 135                 140

Thr His Pro Trp Leu Ile Lys Gly Thr Asn Gly Asp Ile Ile Tyr Glu
145                 150                 155                 160
```

-continued

```
Gly Tyr Lys Met Lys Ile Val Gly Asn Gly Thr Leu Arg Ser Val Tyr
            165                 170                 175
His Trp Glu Glu Glu Gly Val Pro Leu Glu Phe Asp Thr Ser Ala Trp
            180                 185                 190
Thr Val Leu Gly Gly Asp Lys Asp Ile Leu Asn Val Ser Val Asn Val
            195                 200                 205
Asp Ala Leu Thr Asn Leu Ser Met Asp Gly Val Asp Lys Leu Pro Glu
            210                 215                 220
Glu Val Phe Lys Arg Tyr His Val Asn Ser Gly Pro Ile Gly Leu Glu
225                 230                 235                 240
Gln Ala Gly Gly Glu Phe Thr Val Leu Asp Glu Ala Tyr His Arg Thr
            245                 250                 255
Thr His Asp Tyr Gly Phe Thr Pro Gly Arg Gly Ala Phe His Tyr Asn
            260                 265                 270
Leu Leu Thr Ser Trp Ala Gly Leu Lys Glu Asp Pro Ala Arg Pro Gly
            275                 280                 285
Tyr Ala Asp Phe Thr Ala Thr Asn Glu Val Tyr Ala Lys Ser Gln Pro
            290                 295                 300
Ala Ile Asp Lys Phe Glu Ser Leu Tyr Pro Ser Ile Gly Lys Asp Tyr
305                 310                 315                 320
Val Leu Thr Leu Asp Gly Trp Pro Arg Trp Met Trp Glu Ser Pro Asn
            325                 330                 335
Ser Gly Gln Ser Glu His Phe Gly Thr Pro Ser Arg Ala Asn Phe Asp
            340                 345                 350
Ala Ala Ala Asp Ala Ser Ala Lys Leu Ile Lys Ser Ile Asp Thr Arg
            355                 360                 365
Phe Asp Gly Leu Gly Pro Lys Tyr Val Glu Val Lys Asn Glu Ser Thr
            370                 375                 380
Ile Pro Gln Glu Trp Trp Phe Phe Gln Ser Glu Pro Glu Gln Ala Trp
385                 390                 395                 400
Ser Tyr Leu Ser Glu Phe His Asn Lys Val Ala Ala Glu Val Lys Ala
            405                 410                 415
Glu Asn Pro Asp Val Leu Val Gly Gly Pro Ser Ser Ala Phe Met Tyr
            420                 425                 430
Leu Glu Lys Asn Asp Phe Asp Glu Ala Arg Ala Gln Leu Lys Phe Met
            435                 440                 445
Asp Asp Thr Lys Asp Ser Leu Asp Trp Tyr Ser His His Phe Tyr Glu
            450                 455                 460
Asn Ala Asn Leu Phe Ile His Asp Arg Glu Asn Asn Ser Asp Gly Phe
465                 470                 475                 480
Leu Ser Gly Arg Met Glu Ala Val Leu Asp Leu Leu Asn Ala His Met
            485                 490                 495
Ala Asn Thr Asp Asn Val Lys Pro Ile Tyr Ile Thr Glu Glu Gly Thr
            500                 505                 510
Tyr Asn Thr Ala Gly Ser Asp Ala Asp Tyr Phe Gln Lys Leu Val Ala
            515                 520                 525
Phe Asn Gly Tyr Met Leu Arg Phe Ile Asn Tyr Ser Asp Thr Ile Gly
            530                 535                 540
Met Leu Val Pro Tyr Leu Tyr Pro Ile Ile Asn Trp Arg Pro Asn Ser
545                 550                 555                 560
Thr Gly Thr Phe Tyr Lys Tyr Asn Glu Thr Gln Asn Gly Leu Leu Glu
            565                 570                 575
Glu Met Thr Pro Met Glu Ala Tyr Leu Asp Met Trp Lys Asp Tyr Arg
```

```
            580             585             590
Gly Ala Phe Leu Pro Ser Glu Ala Asp Gln Glu Arg Val Phe Thr Asn
            595                 600                 605

Ala Val Arg Tyr Asn Asp Lys Val Tyr Val Ala Val His Asn Leu Asn
    610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
                645                 650                 655

Thr Tyr Glu Gln Lys Asn Val Ala Asp Leu Asn Asn Val Tyr Met Arg
            660                 665                 670

Val Gln Glu Met Ser Val Phe Glu Ile Thr Leu Asp Ser Asn Pro Pro
        675                 680                 685

Phe Thr Lys Thr Trp Glu Arg Glu Phe Ala Tyr Ala Pro Gln Glu Leu
    690                 695                 700

Val Pro Thr Ser Val Asn Ala Pro Ala Ser Phe Thr Val Gln Ala Arg
705                 710                 715                 720

Pro Ala Asp Leu Ala Lys Ala Thr Leu Arg Ile Gly Phe Gly Lys Thr
                725                 730                 735

Gly Ser Gly Phe Ala Glu Asp Met Gln Val Val Asn Ser Gly Asp
            740                 745                 750

Thr Ala Asn Met Gln Ser Phe Ser Lys Asp Leu Ala Tyr Thr Asp Lys
        755                 760                 765

Pro Gly Asn Leu Leu Thr Phe Ala Glu Phe Glu Leu Asp Thr Ser Lys
    770                 775                 780

Leu Leu Thr Ser Asn Thr Ile Glu Ile Thr Leu Pro Asp Asp Asp Gly
785                 790                 795                 800

Tyr Ile Thr Ser Val Gln Ile Ile Glu Tyr His Glu Gln Pro Ala Pro
                805                 810                 815

Thr Gly Ile Ala Thr Ser Ala Leu Ala Ala Pro Val Ala Asp Ala Lys
            820                 825                 830

Ser Lys Leu Ala Ser Thr Ile Ile Ser Ser Thr Gly Asn Glu Val Glu
        835                 840                 845

Pro Gly Gln Lys Trp Val Lys Lys His Ile Arg Asp Thr Leu Asn Ile
    850                 855                 860

Glu Val Ala Lys Ala Glu Val Val Ala Gln Asp Ala Leu Ala Thr Asn
865                 870                 875                 880

Asp Glu Ile Thr Lys Ala Leu Glu Asp Leu Thr Lys Ala Ala Gly Ile
                885                 890                 895

Phe Asp Gln Tyr Thr Lys Thr Lys Ser Ser Pro Thr Gly Asn Arg Gly
            900                 905                 910

Ala Lys Phe Ser Phe Glu Asp Gly Glu Glu Ala Ala Tyr Thr His Asn
        915                 920                 925

Val Asp Thr Val Thr Thr Thr Thr Gly Ser Gln Gly Ala Thr Asp Gly
    930                 935                 940

Ser Lys Ala Leu Gln Ala Glu Phe Thr Ser Phe Thr Ala Phe Ala Trp
945                 950                 955                 960

Asp Thr Thr Gly Thr Tyr Ser Gly Ser Leu Asp Phe Thr Ala Pro
                965                 970                 975

<210> SEQ ID NO 6
<211> LENGTH: 875
<212> TYPE: PRT
<213> ORGANISM: Paenibacillus agarexedens
```

```
<400> SEQUENCE: 6

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45

Ile Gln Arg Ile Asn Phe Leu Gln Phe Pro Asp Gly Gln Tyr Leu Gln
    50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Gly Ser Val Ala Gln Thr
                85                  90                  95

Met Glu Leu Tyr Val Ile Asp Pro Asn Gly Val Glu Thr His Trp Thr
            100                 105                 110

Val Phe Gln Asn Gly Gly Trp Lys Asp Gly Ile Thr Gly Leu Tyr Thr
        115                 120                 125

Asn Tyr Thr Lys Met Gly Phe Gln Glu Asp Asn Pro Thr Glu Gly Ile
    130                 135                 140

Thr His Pro Trp Leu Ile Lys Gly Thr Asn Gly Asp Ile Ile Tyr Glu
145                 150                 155                 160

Gly Tyr Lys Met Lys Ile Val Gly Asn Gly Thr Leu Arg Ser Val Tyr
                165                 170                 175

His Trp Glu Glu Glu Gly Val Pro Leu Glu Phe Asp Thr Ser Ala Trp
            180                 185                 190

Thr Val Leu Gly Gly Asp Lys Asp Ile Leu Asn Val Ser Val Asn Val
        195                 200                 205

Asp Ala Leu Thr Asn Leu Ser Met Asp Gly Val Asp Lys Leu Pro Glu
    210                 215                 220

Glu Val Phe Lys Arg Tyr His Val Asn Ser Gly Pro Ile Gly Leu Glu
225                 230                 235                 240

Gln Ala Gly Gly Glu Phe Thr Val Leu Asp Glu Ala Tyr His Arg Thr
                245                 250                 255

Thr His Asp Tyr Gly Phe Thr Pro Gly Arg Gly Ala Phe His Tyr Asn
            260                 265                 270

Leu Leu Thr Ser Trp Ala Gly Leu Lys Glu Asp Pro Ala Arg Pro Gly
        275                 280                 285

Tyr Ala Asp Phe Thr Ala Thr Asn Glu Val Tyr Ala Lys Ser Gln Pro
    290                 295                 300

Ala Ile Asp Lys Phe Glu Ser Leu Tyr Pro Ser Ile Gly Lys Asp Tyr
305                 310                 315                 320

Val Leu Thr Leu Asp Gly Trp Pro Arg Trp Met Trp Glu Ser Pro Asn
                325                 330                 335

Ser Gly Gln Ser Glu His Phe Gly Thr Pro Ser Arg Ala Asn Phe Asp
            340                 345                 350

Ala Ala Ala Asp Ala Ser Ala Lys Leu Ile Lys Ser Ile Asp Thr Arg
        355                 360                 365

Phe Asp Gly Leu Gly Pro Lys Tyr Val Glu Val Lys Asn Glu Ser Thr
    370                 375                 380

Ile Pro Gln Glu Trp Trp Phe Phe Gln Ser Glu Pro Glu Gln Ala Trp
385                 390                 395                 400

Ser Tyr Leu Ser Glu Phe His Asn Lys Val Ala Ala Glu Val Lys Ala
```

```
                405                 410                 415
Glu Asn Pro Asp Val Leu Val Gly Gly Pro Ser Ser Ala Phe Met Tyr
            420                 425             430
Leu Glu Lys Asn Asp Phe Asp Glu Ala Arg Ala Gln Leu Lys Phe Met
        435                 440             445
Asp Asp Thr Lys Asp Ser Leu Asp Trp Tyr Ser His Phe Tyr Glu
    450             455             460
Asn Ala Asn Leu Phe Ile His Asp Arg Glu Asn Asn Ser Asp Gly Phe
465             470             475             480
Leu Ser Gly Arg Met Glu Ala Val Leu Asp Leu Leu Asn Ala His Met
            485             490             495
Ala Asn Thr Asp Asn Val Lys Pro Ile Tyr Ile Thr Glu Glu Gly Thr
        500             505             510
Tyr Asn Thr Ala Gly Ser Asp Ala Asp Tyr Phe Gln Lys Leu Val Ala
        515             520             525
Phe Asn Gly Tyr Met Leu Arg Phe Ile Asn Tyr Ser Asp Thr Ile Gly
    530             535             540
Met Leu Val Pro Tyr Leu Tyr Pro Ile Ile Asn Trp Arg Pro Asn Ser
545             550             555             560
Thr Gly Thr Phe Tyr Lys Tyr Asn Glu Thr Gln Asn Gly Leu Leu Glu
            565             570             575
Glu Met Thr Pro Met Glu Ala Tyr Leu Asp Met Trp Lys Asp Tyr Arg
        580             585             590
Gly Ala Phe Leu Pro Ser Glu Ala Asp Gln Glu Arg Val Phe Thr Asn
        595             600             605
Ala Val Arg Tyr Asn Asp Lys Val Tyr Val Ala Val His Asn Leu Asn
    610             615             620
Ser Gln Arg Val Asn Leu Asp Leu Asn Val Phe Thr Gly Gly Ala Asn
625             630             635             640
Ile Ala Gly Val Thr Arg Lys His Phe Phe Leu Glu Lys Gly Asp Leu
            645             650             655
Thr Tyr Glu Gln Lys Asn Val Ala Asp Leu Asn Asn Val Tyr Met Arg
            660             665             670
Val Gln Glu Met Ser Val Phe Glu Ile Thr Leu Asp Ser Asn Pro Pro
        675             680             685
Phe Thr Lys Thr Trp Glu Arg Glu Phe Ala Tyr Ala Pro Gln Glu Leu
    690             695             700
Val Pro Thr Ser Val Asn Ala Pro Ala Ser Phe Thr Val Gln Ala Arg
705             710             715             720
Pro Ala Asp Leu Ala Lys Ala Thr Leu Arg Ile Gly Phe Gly Lys Thr
            725             730             735
Gly Ser Gly Phe Ala Glu Asp Met Gln Val Val Asn Ser Gly Asp
            740             745             750
Thr Ala Asn Met Gln Ser Phe Ser Lys Asp Leu Ala Tyr Thr Asp Lys
        755             760             765
Pro Gly Asn Leu Leu Thr Phe Ala Glu Phe Glu Leu Asp Thr Ser Lys
    770             775             780
Leu Leu Thr Ser Asn Thr Ile Glu Ile Thr Leu Pro Asp Asp Gly
785             790             795             800
Tyr Ile Thr Ser Val Gln Ile Ile Glu Tyr His Glu Gln Pro Ala Pro
            805             810             815
Thr Gly Ile Ala Thr Ser Ala Leu Ala Ala Pro Val Ala Asp Ala Lys
        820             825             830
```

```
Ser Lys Leu Ala Ser Thr Ile Ile Ser Ser Thr Gly Asn Glu Val Glu
            835                 840                 845

Pro Gly Gln Lys Trp Val Lys Lys His Ile Arg Asp Thr Leu Asn Ile
850                 855                 860

Glu Val Ala Lys Ala Glu Val Ala Gln Asp
865                 870                 875

<210> SEQ ID NO 7
<211> LENGTH: 775
<212> TYPE: PRT
<213> ORGANISM: Paenibacillus agarexedens

<400> SEQUENCE: 7

Ala Glu Val Asn Asp Glu Leu Pro Glu Asn Ile Arg Thr Asp Lys Ala
1               5                   10                  15

Asp Phe Asp Thr Ile Pro Ala Val Ala Glu His Tyr Lys Gly Gln Phe
            20                  25                  30

Gly Asp Asn Ala Val Ala Tyr Phe Asn Ser Ile Asn Gly Glu Ser Arg
        35                  40                  45

Ile Gln Arg Ile Asn Phe Leu Gln Phe Pro Asp Gly Gln Tyr Leu Gln
50                  55                  60

Ile Asn Gly Glu Val Thr Phe Asp Ile Pro Ala Met Asp Ala Arg Val
65                  70                  75                  80

Trp Arg Leu Phe Gly Asp Val Arg Phe Glu Gly Ser Val Ala Gln Thr
                85                  90                  95

Met Glu Leu Tyr Val Ile Asp Pro Asn Gly Val Glu Thr His Trp Thr
            100                 105                 110

Val Phe Gln Asn Gly Gly Trp Lys Asp Gly Ile Thr Gly Leu Tyr Thr
        115                 120                 125

Asn Tyr Thr Lys Met Gly Phe Gln Glu Asp Asn Pro Thr Glu Gly Ile
130                 135                 140

Thr His Pro Trp Leu Ile Lys Gly Thr Asn Gly Asp Ile Ile Tyr Glu
145                 150                 155                 160

Gly Tyr Lys Met Lys Ile Val Gly Asn Gly Thr Leu Arg Ser Val Tyr
                165                 170                 175

His Trp Glu Glu Glu Gly Val Pro Leu Glu Phe Asp Thr Ser Ala Trp
            180                 185                 190

Thr Val Leu Gly Gly Asp Lys Asp Ile Leu Asn Val Ser Val Asn Val
        195                 200                 205

Asp Ala Leu Thr Asn Leu Ser Met Asp Gly Val Asp Lys Leu Pro Glu
210                 215                 220

Glu Val Phe Lys Arg Tyr His Val Asn Ser Gly Pro Ile Gly Leu Glu
225                 230                 235                 240

Gln Ala Gly Gly Glu Phe Thr Val Leu Asp Glu Ala Tyr His Arg Thr
                245                 250                 255

Thr His Asp Tyr Gly Phe Thr Pro Gly Arg Gly Ala Phe His Tyr Asn
            260                 265                 270

Leu Leu Thr Ser Trp Ala Gly Leu Lys Glu Asp Pro Ala Arg Pro Gly
        275                 280                 285

Tyr Ala Asp Phe Thr Ala Thr Asn Glu Val Tyr Ala Lys Ser Gln Pro
290                 295                 300

Ala Ile Asp Lys Phe Glu Ser Leu Tyr Pro Ser Ile Gly Lys Asp Tyr
305                 310                 315                 320

Val Leu Thr Leu Asp Gly Trp Pro Arg Trp Met Trp Glu Ser Pro Asn
```

```
            325                 330                 335
Ser Gly Gln Ser Glu His Phe Gly Thr Pro Ser Arg Ala Asn Phe Asp
            340                 345                 350

Ala Ala Ala Asp Ala Ser Ala Lys Leu Ile Lys Ser Ile Asp Thr Arg
            355                 360                 365

Phe Asp Gly Leu Gly Pro Lys Tyr Val Glu Val Lys Asn Glu Ser Thr
370                 375                 380

Ile Pro Gln Glu Trp Trp Phe Phe Gln Ser Glu Pro Glu Gln Ala Trp
385                 390                 395                 400

Ser Tyr Leu Ser Glu Phe His Asn Lys Val Ala Ala Glu Val Lys Ala
                405                 410                 415

Glu Asn Pro Asp Val Leu Val Gly Gly Pro Ser Ser Ala Phe Met Tyr
            420                 425                 430

Leu Glu Lys Asn Asp Phe Asp Glu Ala Arg Ala Gln Leu Lys Phe Met
            435                 440                 445

Asp Asp Thr Lys Asp Ser Leu Asp Trp Tyr Ser His His Phe Tyr Glu
450                 455                 460

Asn Ala Asn Leu Phe Ile His Asp Arg Glu Asn Asn Ser Asp Gly Phe
465                 470                 475                 480

Leu Ser Gly Arg Met Glu Ala Val Leu Asp Leu Leu Asn Ala His Met
                485                 490                 495

Ala Asn Thr Asp Asn Val Lys Pro Ile Tyr Ile Thr Glu Glu Gly Thr
            500                 505                 510

Tyr Asn Thr Ala Gly Ser Asp Ala Asp Tyr Phe Gln Lys Leu Val Ala
            515                 520                 525

Phe Asn Gly Tyr Met Leu Arg Phe Ile Asn Tyr Ser Asp Thr Ile Gly
            530                 535                 540

Met Leu Val Pro Tyr Leu Tyr Pro Ile Ile Asn Trp Arg Pro Asn Ser
545                 550                 555                 560

Thr Gly Thr Phe Tyr Lys Tyr Asn Glu Thr Gln Asn Gly Leu Leu Glu
                565                 570                 575

Glu Met Thr Pro Met Glu Ala Tyr Leu Asp Met Trp Lys Asp Tyr Arg
            580                 585                 590

Gly Ala Phe Leu Pro Ser Glu Ala Asp Gln Glu Arg Val Phe Thr Asn
            595                 600                 605

Ala Val Arg Tyr Asn Asp Lys Val Tyr Val Ala Val His Asn Leu Asn
            610                 615                 620

Ser Gln Arg Val Asn Leu Asp Leu Asn Val Phe Thr Gly Gly Ala Asn
625                 630                 635                 640

Ile Ala Gly Val Thr Arg Lys His Phe Phe Leu Glu Lys Gly Asp Leu
                645                 650                 655

Thr Tyr Glu Gln Lys Asn Val Ala Asp Leu Asn Asn Val Tyr Met Arg
            660                 665                 670

Val Gln Glu Met Ser Val Phe Glu Ile Thr Leu Asp Ser Asn Pro Pro
            675                 680                 685

Phe Thr Lys Thr Trp Glu Arg Glu Phe Ala Tyr Ala Pro Gln Glu Leu
690                 695                 700

Val Pro Thr Ser Val Asn Ala Pro Ala Ser Phe Thr Gln Ala Arg
705                 710                 715                 720

Pro Ala Asp Leu Ala Lys Ala Thr Leu Arg Ile Gly Phe Gly Lys Thr
                725                 730                 735

Gly Ser Gly Phe Ala Glu Asp Met Gln Val Val Asn Ser Gly Asp
            740                 745                 750
```

```
            Thr Ala Asn Met Gln Ser Phe Ser Lys Asp Leu Ala Tyr Thr Asp Lys
                755                 760                 765

Pro Gly Asn Leu Leu Thr Phe
                770                 775

<210> SEQ ID NO 8
<211> LENGTH: 5436
<212> TYPE: DNA
<213> ORGANISM: Paenibacillus agarexedens

<400> SEQUENCE: 8
gcagaggtca acgacgagct tcctgagaat attagaaccg acaaggcaga tttcgatacc        60
attcctgccg ttgccgagca ttacaaggga caattcggcg ataatgcggt agcttatttc       120
aacagtatta acgagaaaag ccggattcag cgcattaact tcctgcaatt cccgatgggg       180
caatatttgc agattaatgg cgaggtaacg tttgatattc ctgccatgga tgcgcgagtg       240
tggcgtctgt tcggtgatgt gcgcttcgag ggatccgtcg cgcaaacgat ggagctatat       300
gtcattgacc cgaatggggt cgagacacat tggacagtat tccagaatgg cggctggaag       360
gacggcatca ccggattata taccaactat acgaagatgg gcttccagga agacaacccg       420
acggagggta ttacccatcc ttggctgatt aagggtacga acggcgacat tatttatgaa       480
ggctacaaaa tgaaaatcgt cggcaacgga acgcttcgca cgtctacca ctgggaagag        540 gaaggcgtgc cgctggagtt cgacacctcc gcatggaccg ttcttggtgg agacaaggac       600
attctgaatg tgtccgtcaa tgtggatgcg cttacaaact taagtatgga cggtgtcgat       660
aagctgcccg aggaagtgtt caagcgttac catgtgaaca gtggtccgat cggcttagag       720
caagccggcg cgaatttac ggtgttggac gaggcgtacc acagaacgac tcatgattac         780
ggctttactc ccggccgagg tgcgtttcat tataatctac tgacgagctg gcgggtctt         840 aaggaagatc ctgcgcgccc tggatatgct gactttacag cgacgaatga ggtttatgcg       900
aagagtcagc ctgccatcga caaattcgaa agtctgtatc catccatcgg caaggattat       960
gtcctgacgc tagacggctg gccgaggtgg atgtgggaat cccctaattc cggacaatcg      1020
gagcatttcg gcacaccgtc ccgcgccaac ttcgatgcag cggcggacgc ctcggccaag      1080
ctgatcaaaa gcatcgatac tagatttgac ggactgggtc ccaagtacgt ggaggttaag      1140
aacgaatcga ccatcccgca ggagtggtgg ttcttccagt cggagccaga gcaagcgtgg      1200
agctatttgt ccgagttcca caacaaggta gccgcggaag tgaaggcgga gaatccggac      1260
gtattagtgg gcgaccatc aagcgcattc atgtatttgg agaaaaatga tttcgacgaa        1320
gcgcgcgccc agctgaaatt tatggatgac acgaaagatt ccttggattg gtattcgcat      1380
cacttctatg aaaatgccaa cctgttcatt catgacagag agaacaactc ggatggcttc      1440
ttgagcgggc gaatggaagc ggtgcttgac ctgcttaacg ctcacatggc gaatacggat      1500
aacgtgaagc cgatctatat tacagaagaa ggcacctaca atacggctgg aagcgatgcg      1560
gattacttcc agaagctagt ggccttcaac ggctacatgc tgcgtttcat taattattcc      1620
gatacaatcg gcatgctggt tccttatctg tatcccatca ttaactggcg ccccaactcc      1680
acgggtacgt tctacaaata taatgaaaca cagaatggat tattgaagaa atgacgcca        1740 atggaagcgt atctggacat gtggaaggat tatcgcggtg cattcctgcc ttctgaagcg      1800
gatcaagagc gcgtcttcac gaatgcggtc cgctacaatg acaaggtgta tgtagccgtg      1860
cacaatctga actcgcagcg ggtgaacctt gatctgaatg tgttcacggg aggcgctaat      1920
```

-continued

```
attgcaggcg taactcggaa gcatttcttc ctggagaagg gcgacctgac ctatgaacaa    1980
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttacggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga aatctgctga cctttgcgga atttgagttg    2340
gacaccagca agctgctgac gagcaatacg attgaaatta cgcttccaga cgatgacggc    2400
tatattacaa gcgtacagat tatcgagtac cacgagcagc cggctccaac aggcattgcg    2460
accagcgcac ttgctgcgcc tgttgcggac gccaagtcga agcttgcgtc tactatcata    2520
tcgtctacag gcaatgaggt tgagccaggc cagaagtggg tgaaaaaaca tatccgcgat    2580
acgctcaaca ttgaggtggc aaaagcggag gttgttgcgc aggatgctct agcaacaaac    2640
gatgaaataa cgaaggcgct ggaggatcta accaaagcgg ctggtatttt tgatcaatat    2700
accaaaacaa aatcatctcc aaccggcaat cggggagcca aattctcctt cgaggacgga    2760
gaagaggcag cgtatacaca caatgtggac acggtgacga caacaacagg ctcgcaaggc    2820
gcaacggacg gcagtaaggc acttcaagcg gaatttacgt cctttactgc ctttgcgtgg    2880
gatacaacag gtacgtactc gggcagcctt gattttactg ccccggagga aggctggagc    2940
ctgggtacta cacccattac gttcgacgtt acgaatctga aagctacgc gacacagctg    3000 cgggtagagg tgacagacac atcggacgtt aaaggcactt attatttcac gctgggagca    3060
gatgcttcgc gaagcatcag cattgctgat ttcggcattg cgggaggcac ttggcttgcg    3120
gacggcaatt tcccgagaaa cgcagctatc gataccgaga atctgaagtc gattcgactg    3180
tttgtgtttt ctccaacggc cgctcctgtt acgaacgcag cgcttgccat tgatcatatc    3240
ataattggca gtgcatcgga tccagggcca ggacctggca atccgaacgg tgtgttccta    3300
tccttcgagg atcaggaaga ggttgtctat acgactaatg ccaagacat taccgttacc    3360 agatcagaac agggcgcgac acatggcagc aaagcgctgc atgcggagtt cgattccttc    3420
accgcatacg actgggatac gagcggcaag tattccggca atattgattt tacagcgccg    3480 gagggggct ggagcctggg cagcaagccg cttcagctgg atgtcacgaa tctcgtgaac    3540
acaggagccc agcttcgcgt cgaggttacc gacgttgaga atcatagagg tatttattac    3600
tttgcaattg ctcctaatca agctcgaacg cttacgatat cggatttcgg catctctgcg    3660
gcaagctggc tggcagacgg ctatttcgca aaggcagcgg caattgacac caccaagctg    3720
aaatccattc gattgtatgt atttgagcct accgctatca ccgtgggtca tgccgcactc    3780
gccttcgaca gtctgatcat tggcaacgag ccgatccagc ctactgagga gcagctggca    3840
gccgaagcgg cgaatgcgct gacggcagcc tccttaacct ttgcagcggg ggacatggcg    3900
caagcggtaa cgaaccatat ctcattgcca tctgcagggc ttcatggagc aagccttaca    3960
tgggcatcca gccatccgtc gacggtggcg actgacggga cggttacgag accgcagcat    4020
ggaagcggga atcaggttgt cacgctgact gctaccgtca tgattggagc agcaagctca    4080
accaaggcta ttgaagtcac tgtgcttcaa caagcttcga cttccaatcc acctggtggc    4140
aatgaaaatc cgtctcatcc agagccaagc agtcctccgg aagttcatgt cgatattctg    4200
gtggatggca agaagcagga taagattgct agctccgtta caacaacgga ggcaggacgt    4260
acggttacaa cgattactgt cgatcaacag ttattgaaga acagtctgag caatatggct    4320
```

```
aataacggta tcattacgat tcctgtttct agcggatctg atgttgtgaa tggcaagctt    4380
aatggtcaga tcgtgaagga tcttcagcag aagaatgcgt tcttcgagct aagaaccggc    4440 acctttcct ataagcttcc tataaagcag atcaatataa atgaaatagc caaaggactt     4500
ggatcggatg taaagcttga ggatataacc cttgatctga caatcagtca agtagatgcg    4560
ggaacccagc aggtattgga gaactcggca aagcaaggcg gattcacggt tgttgcccct    4620
cctgttgact tccacatcac ttacacttac caggggcta cggtagaatt ccgaacattc     4680
aacacgttcg tcgagagagc tgtcattatt ccggatggtg tggatccgac tcagattact    4740
acaggggtag tgatggaagc ggatggcaca gtgagacaga ttccgactcg actcgtcaga    4800
gtgaatggca gctaccatgc tgttatgaat agtatgacca acagcactta cgcaatcatt    4860
tggaaccctg cagcttttcca ggatgtgtcc ggtcactggg tagaggaagc tgtgaatgac    4920
ttgggctcca gattggtaat ctcgggcgtt gacggcaatc gcttcgaacc tgatcgatcg    4980
attacccgtg ccgagtttac cgctattctg gtcagagctc ttggattgag gcagagtct    5040 ggcgagccgg catacagcga tgttgcaaaa ggcgtctggt atgaaggtta cctgaatacg    5100
gcgacgaagt acgacttgat taacggctat gccaatggtc aattcggtgc gaatgatctg    5160
atcacacgtg aacaggttat gagtatcatg aacgagcta tggcgctcac tggacttgat     5220
tctgcggcag atatggcaga agcggatgag ctgttgtcca gcttcaagga tggctccgag    5280
gcggcagcct acgcgaagag cggtattgca gccagcatca aggcaggtct cgtactgggc    5340
agaagcgagc aagtgcttgc tccgaaagca gctattacaa gagcggaagt cgcggaggtt    5400
gttcgaagat tgctagagaa gtctgatctg atctag                              5436

<210> SEQ ID NO 9
<211> LENGTH: 4140
<212> TYPE: DNA
<213> ORGANISM: Paenibacillus agarexedens

<400> SEQUENCE: 9
gcagaggtca acgacgagct tcctgagaat attagaaccg acaaggcaga tttcgatacc      60
attcctgccg ttgccgagca ttacaaggga caattcggcg ataatgcggt agcttatttc     120
aacagtatta acggagaaag ccggattcag cgcattaact tcctgcaatt cccggatggg    180
caatatttgc agattaatgg cgaggtaacg tttgatattc ctgccatgga tgcgcgagtg    240
tggcgtctgt tcggtgatgt gcgcttcgag ggatccgtcg cgcaaacgat ggagctatat    300
gtcattgacc cgaatggggt cgagacacat tggacagtat tccagaatgg cggctggaag    360
gacggcatca ccggattata taccaactat acgaagatgg gcttccagga agacaacccg    420
acggagggta ttacccatcc ttggctgatt aagggtacga acggcgacat tatttatgaa    480
ggctacaaaa tgaaaatcgt cggcaacgga acgcttcgca gcgtctacca ctgggaagag    540
gaaggcgtgc cgctggagtt cgacacctcc gcatggaccc ttcttggtgg agacaaggac    600
attctgaatg tgtccgtcaa tgtggatgcg cttacaaact taagtatgga cggtgtcgat    660
aagctgcccg aggaagtgtt caagcgttac catgtgaaca gtggtccgat cggcttagag    720
caagccggcg gcgaatttac ggtgttggac gaggcgtacc acagaacgac tcatgattac    780
ggctttactc ccggccgagg tgcgtttcat tataatctac tgacgagctg gcgggtctt     840 aaggaagatc ctgcgcgccc tggatatgct gactttacag cgacgaatga ggtttatgcg    900
aagagtcagc ctgccatcga caaattcgaa agtctgtatc catccatcgg caaggattat    960
```

```
gtcctgacgc tagacggctg gccgaggtgg atgtgggaat cccctaattc cggacaatcg    1020
gagcatttcg gcacaccgtc ccgcgccaac ttcgatgcag cggcggacgc ctcggccaag    1080
ctgatcaaaa gcatcgatac tagatttgac ggactgggtc ccaagtacgt ggaggttaag    1140
aacgaatcga ccatcccgca ggagtggtgg ttcttccagt cggagccaga gcaagcgtgg    1200
agctatttgt ccgagttcca caacaaggta gccgcgaagt gaaggcggaa gaatccggac    1260
gtattagtgg gcggaccatc aagcgcattc atgtatttgg agaaaaatga tttcgacgaa    1320
gcgcgcgccc agctgaaatt tatggatgac acgaaagatt ccttggattg gtattcgcat    1380
cacttctatg aaaatgccaa cctgttcatt catgacagag agaacaactc ggatggcttc    1440
ttgagcgggc gaatggaagc ggtgcttgac ctgcttaacg ctcacatggc gaatacggat    1500
aacgtgaagc cgatctatat tacagaagaa ggcacctaca atacggctgg aagcgatgcg    1560
gattacttcc agaagctagt ggccttcaac ggctacatgc tgcgtttcat taattattcc    1620
gatacaatcg gcatgctggt tccttatctg tatcccatca ttaactgcg ccccaactcc     1680 acgggtacgt tctacaaata taatgaaaca cagaatggat tattgaaga aatgacgcca     1740 atggaagcgt atctggacat gtggaaggat tatcgcggtg cattcctgcc ttctgaagcg    1800
gatcaagagc gcgtcttcac gaatgcggtc cgctacaatg acaaggtgta tgtagccgtg    1860
cacaatctga actcgcagcg ggtgaacctt gatctgaatg tgttcacggg aggcgctaat    1920
attgcaggcg taactcggaa gcatttcttc ctggagaagg gcgacctgac ctatgaacaa    1980
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttacggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga atctgctga cctttgcgga atttgagttg     2340
gacaccagca agctgctgac gagcaatacg attgaaatta cgcttccaga cgatgacggc    2400
tatattacaa gcgtacagat tatcgagtac cacgagcagc cggctccaac aggcattgcg    2460
accagcgcac ttgctgcgcc tgttgcggac gccaagtcga agcttgcgtc tactatcata    2520
tcgtctacag gcaatgaggt tgagccaggc cagaagtggg tgaaaaaaca tatccgcgat    2580
acgctcaaca ttgaggtggc aaaagcggag gttgttgcgc aggatgctct agcaacaaac    2640
gatgaaataa cgaaggcgct ggaggatcta accaaagcgg ctggtatttt tgatcaatat    2700
accaaaacaa aatcatctcc aaccggcaat cggggagcca aattctcctt cgaggacgga    2760
gaagaggcag cgtatacaca caatgtggac acggtgacga caacaacagg ctcgcaaggc    2820
gcaacggacg gcagtaaggc acttcaagcg gaatttacgt cctttactgc ctttgcgtgg    2880
gatacaacag gtacgtactc gggcagcctt gattttactg ccccggagga aggctggagc    2940
ctgggtacta cacccattac gttcgacgtt acgaatctga aagctacgc gacacagctg     3000 cgggtagagg tgacagacac atcggacgtt aaaggcactt attatttcac gctgggagca    3060
gatgcttcgc gaagcatcag cattgctgat ttcggcattg cggaggcac ttggcttgcg     3120 gacggcaatt tcccgagaaa cgcagctatc gataccgaga atctgaagtc gattcgactg    3180
tttgtgtttt ctccaacggc cgctcctgtt acgaacgcag cgcttgccat tgatcatatc    3240
ataattggca gtgcatcgga tccagggcca ggacctggca atccgaacgg tgtgttccta    3300
tccttcgagg atcaggaaga ggttgtctat acgactaatg gccaagacat taccgttacc    3360
```

-continued

```
agatcagaac agggcgcgac acatggcagc aaagcgctgc atgcggagtt cgattccttc    3420
accgcatacg actgggatac gagcggcaag tattccggca atattgattt tacagcgccg    3480 gagggggggct ggagcctggg cagcaagccg cttcagctgg atgtcacgaa tctcgtgaac    3540
acaggagccc agcttcgcgt cgaggttacc gacgttgaga atcatagagg tatttattac    3600
tttgcaattg ctcctaatca agctcgaacg cttacgatat cggatttcgg catctctgcg    3660
gcaagctggc tggcagacgg ctatttcgca aaggcagcgg caattgacac caccaagctg    3720
aaatccattc gattgtatgt atttgagcct accgctatca ccgtgggtca tgccgcactc    3780
gccttcgaca gtctgatcat tggcaacgag ccgatccagc ctactgagga gcagctggca    3840
gccgaagcgg cgaatgcgct gacggcagcc tccttaacct ttgcagcggg ggacatggcg    3900
caagcggtaa cgaaccatat ctcattgcca tctgcagggc ttcatggagc aagccttaca    3960
tgggcatcca gccatccgtc gacggtggcg actgacggga cggttacgag accgcagcat    4020
ggaagcggga atcaggttgt cacgctgact gctaccgtca tgattggagc agcaagctca    4080
accaaggcta ttgaagtcac tgtgcttcaa caagcttcga cttccaatcc acctggtggc    4140
```

<210> SEQ ID NO 10
<211> LENGTH: 3825
<212> TYPE: DNA
<213> ORGANISM: Paenibacillus agarexedens

<400> SEQUENCE: 10

```
gcagaggtca acgacgagct tcctgagaat attagaaccg acaaggcaga tttcgatacc      60
attcctgccg ttgccgagca ttacaaggga caattcggcg ataatgcggt agcttatttc     120
aacagtatta acgagaaaag ccggattcag cgcattaact tcctgcaatt cccgatgggg     180
caatatttgc agattaatgg cgaggtaacg tttgatattc ctgccatgga tgcgcgagtg     240
tggcgtctgt tcggtgatgt gcgcttcgag ggatccgtcg cgcaaacgat ggagctatat     300
gtcattgacc cgaatggggt cgagacacat tggacagtat tccagaatgg cggctggaag     360
gacggcatca ccggattata taccaactat acgaagatgg gcttccagga agacaacccg     420
acggagggta ttacccatcc ttggctgatt aagggtacga acggcgacat tatttatgaa     480
ggctacaaaa tgaaaatcgt cggcaacgga acgcttcgca gcgtctacca ctgggaagag     540
gaaggcgtgc cgctggagtt cgacacctcc gcatggaccc ttcttggtgg agacaaggac     600
attctgaatg tgtccgtcaa tgtggatgcg cttacaaact taagtatgga cggtgtcgat     660
aagctgcccg aggaagtgtt caagcgttac catgtgaaca gtggtccgat cggcttagag     720
caagccggcg gcgaatttac ggtgttggac gaggcgtacc acagaacgac tcatgattac     780
ggctttactc ccgccgagg tgcgtttcat tataatctac tgacgagctg gcgggtctt     840 aaggaagatc ctgcgcgccc tggatatgct gactttacag cgacgaatga ggtttatgcg     900
aagagtcagc ctgccatcga caattcgaa agtctgtatc catccatcgg caaggattat     960
gtcctgacgc tagacggctg gccgaggtgg atgtgggaat cccctaattc cggacaatcg    1020
gagcatttcg gcacaccgtc ccgcgccaac ttcgatgcag cggcggacgc ctcggccaag    1080
ctgatcaaaa gcatcgatac tagatttgac ggactgggtc ccaagtacgt ggaggttaag    1140
aacgaatcga ccatcccgca ggagtggtgg ttcttccagt cggagccaga gcaagcgtgg    1200
agctatttgt ccgagttcca caacaaggta gccgcgaag tgaaggcgga gaatccggac    1260
gtattagtgg gcggaccatc aagcgcattc atgtatttgg agaaaaatga tttcgacgaa    1320
```

```
gcgcgcgccc agctgaaatt tatggatgac acgaaagatt ccttggattg gtattcgcat    1380
cacttctatg aaaatgccaa cctgttcatt catgacagag agaacaactc ggatggcttc    1440
ttgagcgggc gaatggaagc ggtgcttgac ctgcttaacg ctcacatggc gaatacggat    1500
aacgtgaagc cgatctatat tacagaagaa ggcacctaca atacggctgg aagcgatgcg    1560
gattacttcc agaagctagt ggccttcaac ggctacatgc tgcgtttcat taattattcc    1620
gatacaatcg gcatgctggt tccttatctg tatcccatca ttaactgcg ccccaactcc     1680 acgggtacgt tctacaaata taatgaaaca cagaatggat tattggaaga aatgacgcca    1740
atggaagcgt atctggacat gtggaaggat tatcgcggtg cattcctgcc ttctgaagcg    1800
gatcaagagc gcgtcttcac gaatgcggtc cgctacaatg acaaggtgta tgtagccgtg    1860
cacaatctga actcgcagcg ggtgaacctt gatctgaatg tgttcacggg aggcgctaat    1920
attgcaggcg taactcggaa gcatttcttc ctggagaagg gcgacctgac ctatgaacaa    1980
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttacggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga atctgctga cctttgcgga atttgagttg      2340
gacaccagca agctgctgac gagcaatacg attgaaatta cgcttccaga cgatgacggc    2400
tatattacaa gcgtacagat tatcgagtac cacgagcagc cggctccaac aggcattgcg    2460
accagcgcac ttgctgcgcc tgttgcggac gccaagtcga agcttgcgtc tactatcata    2520
tcgtctacag gcaatgaggt tgagccaggc cagaagtggg tgaaaaaaca tatccgcgat    2580
acgctcaaca ttgaggtggc aaaagcggag gttgttgcgc aggatgctct agcaacaaac    2640
gatgaaataa cgaaggcgct ggaggatcta accaaagcgg ctggtatttt tgatcaatat    2700
accaaaacaa aatcatctcc aaccggcaat cggggagcca aattctcctt cgaggacgga    2760
gaagaggcag cgtatacaca caatgtggac acggtgacga caacaacagg ctcgcaaggc    2820
gcaacggacg gcagtaaggc acttcaagcg gaatttacgt cctttactgc cttttgcgtgg   2880 gatacaacag gtacgtactc gggcagcctt gattttactg ccccggagga aggctggagc    2940
ctgggtacta cacccattac gttcgacgtt acgaatctga gaagctacgc gacacagctg    3000
cgggtagagg tgacagacac atcggacgtt aaaggcactt attatttcac gctgggagca    3060
gatgcttcgc gaagcatcag cattgctgat ttcggcattg cgggaggcac ttggcttgcg    3120
gacggcaatt tcccgagaaa cgcagctatc gataccgaga atctgaagtc gattcgactg    3180
tttgtgtttt ctccaacggc cgctcctgtt acgaacgcag cgcttgccat tgatcatatc    3240
ataattggca gtgcatcgga tccagggcca ggacctggca atccgaacgg tgtgttccta    3300
tccttcgagg atcaggaaga ggttgtctat acgactaatg ccaagacat taccgttacc     3360 agatcagaac agggcgcgac acatggcagc aaagcgctgc atgcggagtt cgattccttc    3420
accgcatacg actgggatac gagcggcaag tattccggca atattgattt tacagcgccg    3480 gagggggggct ggagcctggg cagcaagccg cttcagctgg atgtcacgaa tctcgtgaac   3540
acaggagccc agcttcgcgt cgaggttacc gacgttgaga tcatagagg tatttattac     3600 tttgcaattg ctcctaatca agctcgaacg cttacgatat cggatttcgg catctctgcg    3660
gcaagctggc tggcagacgg ctatttcgca aaggcagcgg caattgacac caccaagctg    3720
```

```
aaatccattc gattgtatgt atttgagcct accgctatca ccgtgggtca tgccgcactc    3780
gccttcgaca gtctgatcat tggcaacgag ccgatccagc ctact                   3825

<210> SEQ ID NO 11
<211> LENGTH: 3288
<212> TYPE: DNA
<213> ORGANISM: Paenibacillus agarexedens

<400> SEQUENCE: 11
gcagaggtca acgacgagct tcctgagaat attagaaccg acaaggcaga tttcgatacc     60
attcctgccg ttgccgagca ttacaaggga caattcggcg ataatgcggt agcttatttc    120
aacagtatta acgagaaag ccggattcag cgcattaact tcctgcaatt cccggatggg    180
caatatttgc agattaatgg cgaggtaacg tttgatattc ctgccatgga tgcgcgagtg    240
tggcgtctgt tcggtgatgt gcgcttcgag ggatccgtcg cgcaaacgat ggagctatat    300
gtcattgacc cgaatggggt cgagacacat tggacagtat tccagaatgg cggctggaag    360
gacggcatca ccggattata taccaactat acgaagatgg gcttccagga agacaacccg    420
acggagggta ttacccatcc ttggctgatt aagggtacga acggcgacat tatttatgaa    480
ggctacaaaa tgaaaatcgt cggcaacgga acgcttcgca gcgtctacca ctgggaagag    540
gaaggcgtgc cgctggagtt cgacacctcc gcatggaccg ttcttggtgg agacaaggac    600
attctgaatg tgtccgtcaa tgtggatgcg cttacaaact taagtatgga cggtgtcgat    660
aagctgcccg aggaagtgtt caagcgttac catgtgaaca gtggtccgat cggcttagag    720
caagccggcg gcgaatttac ggtgttggac gaggcgtacc acagaacgac tcatgattac    780
ggctttactc ccggccgagg tgcgtttcat tataatctac tgacgagctg ggcgggtctt    840
aaggaagatc ctgcgcgccc tggatatgct gactttacag cgacgaatga ggtttatgcg    900
aagagtcagc ctgccatcga caaattcgaa agtctgtatc catccatcgg caaggattat    960
gtcctgacgc tagacggctg ccgaggtgg atgtgggaat cccctaattc cggacaatcg   1020
gagcatttcg gcacaccgtc ccgcgccaac ttcgatgcag cggcggacgc ctcggccaag   1080
ctgatcaaaa gcatcgatac tagatttgac ggactgggtc ccaagtacgt ggaggttaag   1140
aacgaatcga ccatcccgca ggagtggtgg ttcttccagt cggagccaga gcaagcgtgg   1200
agctatttgt ccgagttcca caacaaggta gccgcgaag tgaaggcgga gaatccggac   1260
gtattagtgg gcggaccatc aagcgcattc atgtatttgg agaaaaatga tttcgacgaa   1320
gcgcgcgccc agctgaaatt tatggatgac acgaaagatt ccttggattg gtattcgcat   1380
cacttctatg aaaatgccaa cctgttcatt catgacagag agaacaactc ggatggcttc   1440
ttgagcgggc gaatggaagc ggtgcttgac ctgcttaacg ctcacatggc gaatacggat   1500
aacgtgaagc cgatctatat tacagaagaa ggcacctaca atacggctgg aagcgatgcg   1560
gattacttcc agaagctagt ggccttcaac ggctacatgc tgcgtttcat taattattcc   1620
gatacaatcg gcatgctggt tccttatctg tatcccatca ttaactggcg ccccaactcc   1680
acgggtacgt tctacaaata taatgaaaca cagaatggat tattggaaga atgacgccca   1740
atggaagcgt atctggacat gtggaaggat tatcgcggtg cattcctgcc ttctgaagcg   1800
gatcaagagc gcgtcttcac gaatgcggtc cgctacaatg acaaggtgta tgtagccgtg   1860
cacaatctga actcgcagcg ggtgaacctt gatctgaatg tgttcacggg aggcgctaat   1920
attgcaggcg taactcggaa gcatttcttc ctggagaagg gcgacctgac ctatgaacaa   1980
```

```
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttacggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga aatctgctga cctttgcgga atttgagttg    2340
gacaccagca agctgctgac gagcaatacg attgaaatta cgcttccaga cgatgacggc    2400
tatattacaa gcgtacagat tatcgagtac cacgagcagc cggctccaac aggcattgcg    2460
accagcgcac ttgctgcgcc tgttgcggac gccaagtcga agcttgcgtc tactatcata    2520
tcgtctacag gcaatgaggt tgagccaggc cagaagtggg tgaaaaaaca tatccgcgat    2580
acgctcaaca ttgaggtggc aaaagcggag gttgttgcgc aggatgctct agcaacaaac    2640
gatgaaataa cgaaggcgct ggaggatcta accaaagcgg ctggtatttt tgatcaatat    2700
accaaaacaa aatcatctcc aaccggcaat cggggagcca aattctcctt cgaggacgga    2760
gaagaggcag cgtatacaca caatgtggac acggtgacga caacaacagg ctcgcaaggc    2820
gcaacggacg gcagtaaggc acttcaagcg gaatttacgt cctttactgc ctttgcgtgg    2880
gatacaacag gtacgtactc gggcagcctt gattttactg ccccggagga aggctggagc    2940
ctgggtacta cacccattac gttcgacgtt acgaatctga aagctacgc gacacagctg    3000 cgggtagagg tgacagacac atcggacgtt aaaggcactt attatttcac gctgggagca    3060
gatgcttcgc gaagcatcag cattgctgat ttcggcattg cggaggcac ttggcttgcg    3120 gacggcaatt tcccgagaaa cgcagctatc gataccgaga atctgaagtc gattcgactg    3180
tttgtgtttt ctccaacggc cgctcctgtt acgaacgcag cgcttgccat tgatcatatc    3240
ataattggca gtgcatcgga tccagggcca ggacctggca atccgaac              3288
```

<210> SEQ ID NO 12
<211> LENGTH: 2925
<212> TYPE: DNA
<213> ORGANISM: Paenibacillus agarexedens

<400> SEQUENCE: 12

```
gcagaggtca acgacgagct tcctgagaat attagaaccg acaaggcaga tttcgatacc     60
attcctgccg ttgccgagca ttacaaggga caattcggcg ataatgcggt agcttatttc    120
aacagtatta acggagaaag ccggattcag cgcattaact tcctgcaatt cccgatgggg    180
caatatttgc agattaatgg cgaggtaacg tttgatattc ctgccatgga tgcgcgagtg    240
tggcgtctgt tcggtgatgt gcgcttcgag ggatccgtcg cgcaaacgat ggagctatat    300
gtcattgacc cgaatggggt cgagacacat tggacagtat tccagaatgg cggctggaag    360
gacggcatca ccggattata taccaactat acgaagatgg gcttccagga agacaacccg    420
acggagggta ttacccatcc ttggctgatt aagggtacga acggcgacat tatttatgaa    480
ggctacaaaa tgaaaatcgt cggcaacgga acgcttcgca gcgtctacca ctgggaagag    540
gaaggcgtgc cgctggagtt cgacacctcc gcatggaccg ttcttggtgg agacaaggac    600
attctgaatg tgtccgtcaa tgtggatgcg cttacaaact taagtatgga cggtgtcgat    660
aagctgcccg aggaagtgtt caagcgttac catgtgaaca gtggtccgat cggcttagag    720
caagccggcg gcgaatttac ggtgttggac gaggcgtacc acagaacgac tcatgattac    780
ggctttactc ccggccgagg tgcgtttcat tataatctac tgacgagctg gcgggtctt    840
```

```
aaggaagatc ctgcgcgccc tggatatgct gactttacag cgacgaatga ggtttatgcg      900
aagagtcagc ctgccatcga caaattcgaa agtctgtatc catccatcgg caaggattat      960
gtcctgacgc tagacggctg gccgaggtgg atgtgggaat cccctaattc cggacaatcg     1020
gagcatttcg gcacaccgtc ccgcgccaac ttcgatgcag cggcggacgc ctcggccaag     1080
ctgatcaaaa gcatcgatac tagatttgac ggactgggtc ccaagtacgt ggaggttaag     1140
aacgaatcga ccatcccgca ggagtggtgg ttcttccagt cggagccaga gcaagcgtgg     1200
agctatttgt ccgagttcca caacaaggta gccgcggaag tgaaggcgga gaatccggac     1260
gtattagtgg gcgaccatc aagcgcattc atgtatttgg agaaaaatga tttcgacgaa      1320
gcgcgcgccc agctgaaatt tatggatgac acgaaagatt ccttggattg gtattcgcat     1380
cacttctatg aaaatgccaa cctgttcatt catgacagag agaacaactc ggatggcttc     1440
ttgagcgggc gaatggaagc ggtgcttgac ctgcttaacg ctcacatggc gaatacggat     1500
aacgtgaagc cgatctatat tacagaagaa ggcacctaca atacggctgg aagcgatgcg     1560
gattacttcc agaagctagt ggccttcaac ggctacatgc tgcgtttcat taattattcc     1620
gatacaatcg gcatgctggt tccttatctg tatcccatca ttaactggcg ccccaactcc     1680
acgggtacgt tctacaaata taatgaaaca cagaatggat tattggaaga aatgacgcca     1740
atggaagcgt atctggacat gtggaaggat tatcgcggtg cattcctgcc ttctgaagcg     1800
gatcaagagc gcgtcttcac gaatgcggtc cgctacaatg acaaggtgta tgtagccgtg     1860
cacaatctga actcgcagcg ggtgaacctt gatctgaatg tgttcacggg aggcgctaat     1920
attgcaggcg taactcggaa gcatttcttc ctggagaagg gcgacctgac ctatgaacaa     1980
aagaatgtag cagatctgaa caatgtgtat atgcgtgtgc aggagatgag cgtattcgag     2040
attacacttg attccaatcc tccattcacc aaaacatggg agagagaatt tgcatacgct     2100
cctcaggaac ttgtgccgac gagcgtaaat gcacccgcct catttacggt tcaagcgcgg     2160
cctgctgatc tcgccaaagc gactcttcgt attggcttcg gcaagacggg cagtgggttt     2220
gcagaggata tgcaagtggt tgtaaattcg ggtgatacgg ccaacatgca aagcttcagc     2280
aaggatctgg cctatacgga taagcctgga atctgctga cctttgcgga atttgagttg      2340
gacaccagca agctgctgac gagcaatacg attgaaatta cgcttccaga cgatgacggc     2400
tatattacaa gcgtacagat tatcgagtac cacgagcagc cggctccaac aggcattgcg     2460
accagcgcac ttgctgcgcc tgttgcggac gccaagtcga agcttgcgtc tactatcata     2520
tcgtctacag gcaatgaggt tgagccaggc cagaagtggg tgaaaaaaca tatccgcgat     2580
acgctcaaca ttgaggtggc aaaagcggag gttgttgcgc aggatgctct agcaacaaac     2640
gatgaaataa cgaaggcgct ggaggatcta accaaagcgg ctggtatttt tgatcaatat     2700
accaaaacaa aatcatctcc aaccggcaat cggggagcca aattctcctt cgaggacgga     2760
gaagaggcag cgtatacaca caatgtggac acggtgacga caacaacagg ctcgcaaggc     2820
gcaacggacg gcagtaaggc acttcaagcg gaatttacgt cctttactgc ctttgcgtgg     2880
gatacaacag gtacgtactc gggcagcctt gattttactg ccccg                    2925
```

<210> SEQ ID NO 13
<211> LENGTH: 2625
<212> TYPE: DNA
<213> ORGANISM: Paenibacillus agarexedens

<400> SEQUENCE: 13

```
gcagaggtca acgacgagct tcctgagaat attagaaccg acaaggcaga tttcgatacc      60
attcctgccg ttgccgagca ttacaaggga caattcggcg ataatgcggt agcttatttc     120
aacagtatta acggagaaag ccggattcag cgcattaact tcctgcaatt cccggatggg     180
caatatttgc agattaatgg cgaggtaacg tttgatattc ctgccatgga tgcgcgagtg     240
tggcgtctgt tcggtgatgt gcgcttcgag ggatccgtcg cgcaaacgat ggagctatat     300
gtcattgacc cgaatggggt cgagacacat tggacagtat tccagaatgg cggctggaag     360
gacggcatca ccggattata taccaactat acgaagatgg cttccagga agacaacccg     420
acggagggta ttacccatcc ttggctgatt aagggtacga acggcgacat tatttatgaa     480
ggctacaaaa tgaaaatcgt cggcaacgga acgcttcgca gcgtctacca ctgggaagag     540
gaaggcgtgc cgctggagtt cgacacctcc gcatggaccg ttcttggtgg agacaaggac     600
attctgaatg tgtccgtcaa tgtggatgcg cttacaaact taagtatgga cggtgtcgat     660
aagctgcccg aggaagtgtt caagcgttac catgtgaaca gtggtccgat cggcttagag     720
caagccggcg gcgaatttac ggtgttggac gaggcgtacc acagaacgac tcatgattac     780
ggctttactc ccggccgagg tgcgtttcat tataatctac tgacgagctg gcgggtctt      840
aaggaagatc ctgcgcgccc tggatatgct gactttacag cgacgaatga ggtttatgcg     900
aagagtcagc ctgccatcga caaattcgaa agtctgtatc catccatcgg caaggattat     960
gtcctgacgc tagacggctg gccgaggtgg atgtgggaat cccctaattc cggacaatcg    1020
gagcatttcg gcacaccgtc ccgcgccaac ttcgatgcag cggcggacgc ctcggccaag    1080
ctgatcaaaa gcatcgatac tagatttgac ggactgggtc ccaagtacgt ggaggttaag    1140
aacgaatcga ccatcccgca ggagtggtgg ttcttccagt cggagccaga gcaagcgtgg    1200
agctatttgt ccgagttcca caacaaggta gccgcgaag tgaaggcgga gaatccggac    1260
gtattagtgg gcggaccatc aagcgcattc atgtatttgg agaaaaatga tttcgacgaa    1320
gcgcgcgccc agctgaaatt tatggatgac acgaaagatt ccttggattg gtattcgcat    1380
cacttctatg aaaatgccaa cctgttcatt catgacagag agaacaactc ggatggcttc    1440
ttgagcgggc aatggaagc ggtgcttgac ctgcttaacg ctcacatggc gaatacggat    1500
aacgtgaagc cgatctatat tacagaagaa ggcacctaca atacggctgg aagcgatgcg    1560
gattacttcc agaagctagt ggccttcaac ggctacatgc tgcgtttcat taattattcc    1620
gatacaatcg gcatgctggt tccttatctg tatcccatca ttaactggcg ccccaactcc    1680
acgggtacgt tctacaaata taatgaaaca cagaatggat tattggaaga atgacgccca    1740
atggaagcgt atctggacat gtggaaggat tatcgcggtg cattcctgcc ttctgaagcg    1800
gatcaagagc gcgtcttcac gaatgcggtc cgctacaatg acaaggtgta tgtagccgtg    1860
cacaatctga actcgcagcg ggtgaacctt gatctgaatg tgttcacggg aggcgctaat    1920
attgcaggcg taactcggaa gcatttcttc ctggagaagg gcgacctgac ctatgaacaa    1980
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttaccggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga aatctgctga ccttttgcgga atttgagttg    2340
gacaccagca agctgctgac gagcaatacg attgaaatta cgcttccaga cgatgacggc    2400
```

| | | | | |
|---|---|---|---|---|
| tatattacaa | gcgtacagat | tatcgagtac | cacgagcagc | cggctccaac | aggcattgcg | 2460 |
| accagcgcac | ttgctgcgcc | tgttgcggac | gccaagtcga | agcttgcgtc | tactatcata | 2520 |
| tcgtctacag | gcaatgaggt | tgagccaggc | cagaagtggg | tgaaaaaaca | tatccgcgat | 2580 |
| acgctcaaca | ttgaggtggc | aaaagcggag | gttgttgcgc | aggat | | 2625 |

<210> SEQ ID NO 14
<211> LENGTH: 2325
<212> TYPE: DNA
<213> ORGANISM: Paenibacillus agarexedens

<400> SEQUENCE: 14

| | | | | | |
|---|---|---|---|---|---|
| gcagaggtca | acgacgagct | tcctgagaat | attagaaccg | acaaggcaga | tttcgatacc | 60 |
| attcctgccg | ttgccgagca | ttacaaggga | caattcggcg | ataatgcggt | agcttatttc | 120 |
| aacagtatta | acggagaaag | ccggattcag | cgcattaact | tcctgcaatt | cccggatggg | 180 |
| caatatttgc | agattaatgg | cgaggtaacg | tttgatattc | ctgccatgga | tgcgcgagtg | 240 |
| tggcgtctgt | tcggtgatgt | gcgcttcgag | ggatccgtcg | cgcaaacgat | ggagctatat | 300 |
| gtcattgacc | cgaatgggt | cgagacacat | tggacagtat | tccagaatgg | cggctggaag | 360 |
| gacggcatca | ccggattata | taccaactat | acgaagatgg | gcttccagga | agacaacccg | 420 |
| acggagggta | ttacccatcc | ttggctgatt | aagggtacga | acggcgacat | tatttatgaa | 480 |
| ggctacaaaa | tgaaaatcgt | cggcaacgga | acgcttcgca | gcgtctacca | ctgggaagag | 540 |
| gaaggcgtgc | cgctggagtt | cgacacctcc | gcatggaccg | ttcttggtgg | agacaaggac | 600 |
| attctgaatg | tgtccgtcaa | tgtggatgcg | cttacaaact | taagtatgga | cggtgtcgat | 660 |
| aagctgcccg | aggaagtgtt | caagcgttac | catgtgaaca | gtggtccgat | cggcttagag | 720 |
| caagccggcg | gcgaatttac | ggtgttggac | gaggcgtacc | acagaacgac | tcatgattac | 780 |
| ggctttactc | ccggccgagg | tcgtttcat | ataatctac | tgacgagctg | ggcgggtctt | 840 |
| aaggaagatc | ctgcgcgccc | tggatatgct | gactttacag | cgacgaatga | ggtttatgcg | 900 |
| aagagtcagc | ctgccatcga | caaattcgaa | agtctgtatc | catccatcgg | caaggattat | 960 |
| gtcctgacgc | tagacggctg | gccgaggtgg | atgtgggaat | cccctaattc | cggacaatcg | 1020 |
| gagcatttcg | gcacaccgtc | ccgcgccaac | ttcgatgcag | cggcggacgc | tcggccaag | 1080 |
| ctgatcaaaa | gcatcgatac | tagatttgac | ggactgggtc | ccaagtacgt | ggaggttaag | 1140 |
| aacgaatcga | ccatcccgca | ggagtggtgg | ttcttccagt | cggagccaga | gcaagcgtgg | 1200 |
| agctatttgt | ccgagttcca | caacaaggta | gccgcgaag | tgaaggcgga | gaatccggac | 1260 |
| gtattagtgg | gcggaccatc | aagcgcattc | atgtatttgg | agaaaaatga | tttcgacgaa | 1320 |
| gcgcgcgccc | agctgaaatt | tatggatgac | acgaaagatt | ccttggattg | gtattcgcat | 1380 |
| cacttctatg | aaaatgccaa | cctgttcatt | catgacagag | agaacaactc | ggatggcttc | 1440 |
| ttgagcgggc | gaatgaagc | ggtgcttgac | ctgcttaacg | ctcacatggc | gaatacggat | 1500 |
| aacgtgaagc | cgatctatat | tacagaagaa | ggcacctaca | atacggctgg | aagcgatgcg | 1560 |
| gattacttcc | agaagctagt | ggccttcaac | ggctacatgc | tgcgtttcat | taattattcc | 1620 |
| gatacaatcg | gcatgctggt | tccttatctg | tatcccatca | ttaactggcg | ccccaactcc | 1680 |
| acgggtacgt | tctacaaata | taatgaaaca | cagaatggat | tattggaaga | aatgacgcca | 1740 |
| atggaagcgt | atctggacat | gtggaaggat | tatcgcggtg | cattcctgcc | ttctgaagcg | 1800 |
| gatcaagagc | gcgtcttcac | gaatgcggtc | cgctacaatg | acaaggtgta | tgtagccgtg | 1860 |

```
cacaatctga actcgcagcg ggtgaacctt gatctgaatg tgttcacggg aggcgctaat    1920
attgcaggcg taactcggaa gcatttcttc ctggagaagg gcgacctgac ctatgaacaa    1980
aagaatgtag cagatctgaa caatgtgtat atgcgtgtgc aggagatgag cgtattcgag    2040
attacacttg attccaatcc tccattcacc aaaacatggg agagagaatt tgcatacgct    2100
cctcaggaac ttgtgccgac gagcgtaaat gcacccgcct catttacggt tcaagcgcgg    2160
cctgctgatc tcgccaaagc gactcttcgt attggcttcg gcaagacggg cagtgggttt    2220
gcagaggata tgcaagtggt tgtaaattcg ggtgatacgg ccaacatgca aagcttcagc    2280
aaggatctgg cctatacgga taagcctgga atctgctga cctt                    2325
```

<210> SEQ ID NO 15
<211> LENGTH: 10695
<212> TYPE: DNA
<213> ORGANISM: Artificial Sequence
<220> FEATURE:
<223> OTHER INFORMATION: vector

<400> SEQUENCE: 15

```
atccggatat agttcctcct ttcagcaaaa aaccctcaa gacccgttta gaggccccaa       60
ggggttatgc tagttattgc tcagcggtgg cagcagccaa ctcagcttcc tttcgggctt     120
tgttagcagc cggatctcag tggtggtggt ggtggtgctc gagttagtgg tggtggtggt     180
ggtggatcag atcagacttc tctagcaatc ttcgaacaac ctccgcgact ccgctcttg     240 taatagctgc tttcggagca agcacttgct cgcttctgcc cagtacgaga cctgccttga     300
tgctggctgc aataccgctc ttcgcgtagg ctgccgcctc ggagccatcc ttgaagctgg     360
acaacagctc atccgcttct gccatctctg ccgcagaatc aagtccagtg agcgccatag     420
ctcgttccat gatactcata acctgttcac gtgtgatcag atcattcgca ccgaattgac     480
cattggcata gccgttaatc aagtcgtact tcgtcgccgt attcaggtaa ccttcatacc     540
agacgccttt tgcaacatcg ctgtatgccg gctcgccaga ctctgccctc aatccaagag     600
ctctgaccag aatagcggta aactcggcac gggtaatcga tcgatcaggt tcgaagcgat     660
tgccgtcaac gcccgagatt accaatctgg agcccaagtc attcacagct tcctctaccc     720
agtgaccgga cacatcctgg aaagctgcag ggttccaaat gattgcgtaa gtgctgttgg     780
tcatactatt cataacagca tggtagctgc cattcactct gacgagtcga gtcggaatct     840
gtctcactgt gccatccgct tccatcacta ccctgtagt aatctgagtc ggatccacac      900
catccggaat aatgacagct ctctcgacga acgtgttgaa tgttcggaat tctaccgtag     960 cccctggta agtgtaagtg atgtggaagt caacaggagg ggcaacaacc gtgaatccgc     1020
cttgctttgc cgagttctcc aatacctgct gggttcccgc atctacttga ctgattgtca    1080
gatcaagggt tatatcctca agctttacat ccgatccaag tcctttggct atttcattta    1140
tattgatctg ctttatagga agcttatagg aaaaggtgcc ggttcttagc tcgaagaacg    1200
cattcttctg ctgaagatcc ttcacgatct gaccattaag cttgccattc acaacatcag    1260
atccgctaga aacaggaatc gtaatgatac cgttattagc catattgctc agactgttct    1320
tcaataactg ttgatcgaca gtaatcgttg taaccgtacg tcctgcctcc gttgttgtaa    1380
cggagctagc aatcttatcc tgcttcttgc catccaccag aatatcgaca tgaacttccg    1440
gaggactgct tggctctgga tgagacggat tttcattgcc accaggtgga ttggaagtcg    1500
aagcttgttg aagcacagtg acttcaatag ccttggttga gcttgctgct ccaatcatga    1560
cggtagcagt cagcgtgaca acctgattcc cgcttccatg ctgcggtctc gtaaccgtcc    1620
```

```
cgtcagtcgc caccgtcgac ggatggctgg atgcccatgt aaggcttgct ccatgaagcc   1680
ctgcagatgg caatgagata tggttcgtta ccgcttgcgc catgtccccc gctgcaaagg   1740
ttaaggaggc tgccgtcagc gcattcgccg cttcggctgc cagctgctcc tcagtaggct   1800
ggatcggctc gttgccaatg atcagactgt cgaaggcgag tgcggcatga cccacggtga   1860
tagcggtagg ctcaaataca tacaatcgaa tggatttcag cttggtggtg tcaattgccg   1920
ctgcctttgc gaaatagccg tctgccagcc agcttgccgc agagatgccg aaatccgata   1980
tcgtaagcgt tcgagcttga ttaggagcaa ttgcaaagta ataaatacct ctatgattct   2040
caacgtcggt aacctcgacg cgaagctggg ctcctgtgtt cacgagattc gtgacatcca   2100
gctgaagcgg cttgctgccc aggctccagc cccctccgg cgctgtaaaa tcaatattgc    2160
cggaatactt gccgctcgta tcccagtcgt atgcggtgaa ggaatcgaac tccgcatgca   2220
gcgctttgct gccatgtgtc gcgccctgtt ctgatctggt aacggtaatg tcttggccat   2280
tagtcgtata gacaacctct tcctgatcct cgaaggatag gaacacaccg ttcggattgc   2340
caggtcctgg ccctggatcc gatgcactgc caattatgat atgatcaatg gcaagcgctg   2400
cgttcgtaac aggagcggcc gttggagaaa acacaaacag tcgaatcgac ttcagattct   2460
cggtatcgat agctgcgttt ctcgggaaat tgccgtccgc aagccaagtg cctcccgcaa   2520
tgccgaaatc agcaatgctg atgcttcgcg aagcatctgc tcccagcgtg aaataataag   2580
tgcctttaac gtccgatgtg tctgtcacct ctacccgcag ctgtgtcgcg tagcttctca   2640
gattcgtaac gtcgaacgta atgggtgtag tacccaggct ccagccttcc tccggggcag   2700
taaaatcaag gctgcccgag tacgtacctg ttgtatccca cgcaaaggca gtaaaggacg   2760
taaattccgc ttgaagtgcc ttactgccgt ccgttgcgcc ttgcgagcct gttgttgtcg   2820
tcaccgtgtc cacattgtgt gtatacgctg cctcttctcc gtcctcgaag gagaatttgg   2880
ctccccgatt gccggttgga gatgattttg ttttggtata ttgatcaaaa ataccagccg   2940
ctttggttag atcctccagc gccttcgtta tttcatcgtt tgttgctaga gcatcctgcg   3000
caacaacctc cgcttttgcc acctcaatgt tgagcgtatc gcggatatgt ttttcaccc    3060 acttctggcc tggctcaacc tcattgcctg tagacgatat gatagtagac gcaagcttcg   3120
acttggcgtc cgcaacaggc gcagcaagtg cgctggtcgc aatgcctgtt ggagccggct   3180
gctcgtggta ctcgataatc tgtacgcttg taatatagcc gtcatcgtct ggaagcgtaa   3240
tttcaatcgt attgctcgtc agcagcttgc tggtgtccaa ctcaaattcc gcaaaggtca   3300
gcagatttcc aggcttatcc gtataggcca gatccttgct gaagctttgc atgttggccg   3360
tatcacccga atttacaacc acttgcatat cctctgcaaa cccactgccc gtcttgccga   3420
agccaatacg aagagtcgct ttggcgagat cagcaggccg cgcttgaacc gtaaatgagg   3480
cgggtgcatt tacgctcgtc ggcacaagtt cctgaggagc gtatgcaaat tctctctccc   3540
atgttttggt gaatggagga ttggaatcaa gtgtaatctc gaatacgctc atctcctgca   3600
cacgcatata cacattgttc agatctgcta cattcttttg ttcataggtc aggtcgccct   3660
tctccaggaa gaaatgcttc cgagttacgc ctgcaatatt agcgcctccc gtgaacacat   3720
tcagatcaag gttcacccgc tgcgagttca gattgtgcac ggctacatac accttgtcat   3780
tgtagcggac cgcattcgtg aagacgcgct cttgatccgc ttcagaaggc aggaatgcac   3840
cgcgataatc cttccacatg tccagatacg cttccattgg cgtcatttct tccaataatc   3900
cattctgtgt ttcattatat ttgtagaacg taccgtggc gttggggcgc cagttaatga    3960
```

```
tgggatacag ataaggaacc agcatgccga ttgtatcgga ataattaatg aaacgcagca    4020
tgtagccgtt gaaggccact agcttctgga agtaatccgc atcgcttcca gccgtattgt    4080
aggtgccttc ttctgtaata tagatcggct tcacgttatc cgtattcgcc atgtgagcgt    4140
taagcaggtc aagcaccgct tccattcgcc cgctcaagaa gccatccgag ttgttctctc    4200
tgtcatgaat gaacaggttg gcattttcat agaagtgatg cgaataccaa tccaaggaat    4260
ctttcgtgtc atccataaat ttcagctggg cgcgcgcttc gtcgaaatca tttttctcca    4320
aatacatgaa tgcgcttgat ggtccgccca ctaatacgtc cggattctcc gccttcactt    4380
ccgcggctac cttgttgtgg aactcggaca aatagctcca cgcttgctct ggctccgact    4440
ggaagaacca ccactcctgc gggatggtcg attcgttctt aacctccacg tacttgggac    4500
ccagtccgtc aaatctagta tcgatgcttt tgatcagctt ggccgaggcg tccgccgctg    4560
catcgaagtt ggcgcgggac ggtgtgccga aatgctccga ttgtccggaa ttaggggatt    4620
cccacatcca cctcggccag ccgtctagcg tcaggacata atccttgccg atggatggat    4680
acagactttc gaatttgtcg atggcaggct gactcttcgc ataaacctca ttcgtcgctg    4740
taaagtcagc atatccaggg cgcgcaggat cttccttaag acccgcccag ctcgtcagta    4800
gattataatg aaacgcacct cggccgggag taaagccgta atcatgagtc gttctgtggt    4860
acgcctcgtc caacaccgta aattcgccgc cggcttgctc taagccgatc ggaccactgt    4920
tcacatggta acgcttgaac acttcctcgg gcagcttatc gacaccgtcc atacttaagt    4980
ttgtaagcgc atccacattg acggacacat tcagaatgtc cttgtctcca ccaagaacgg    5040
tccatgcgga ggtgtcgaac tccagcggca cgccttcctc ttcccagtgg tagacgctgc    5100
gaagcgttcc gttgccgacg attttcattt tgtagccttc ataaataatg tcgccgttcg    5160 taccccttaat cagccaagga tgggtaatac cctccgtcgg gttgtcttcc tggaagccca    5220
tcttcgtata gttggtatat aatccggtga tgccgtcctt ccagccgcca ttctggaata    5280
ctgtccaatg tgtctcgacc ccattcgggt caatgacata tagctccatc gtttgcgcga    5340
cggatccctc gaagcgcaca tcaccgaaca gacgccacac tcgcgcatcc atggcaggaa    5400
tatcaaacgt tacctcgcca ttaatctgca aatattgccc atccgggaat tgcaggaagt    5460
taatgcgctg aatccggctt tctccgttaa tactgttgaa ataagctacc gcattatcgc    5520
cgaattgtcc cttgtaatgc tcggcaacgg caggaatggt atcgaaatct gccttgtcgg    5580
ttctaatatt ctcaggaagc tcgtcgttga cctctgccat atgtatatct ccttcttaaa    5640
gttaaacaaa attatttcta gagggggaatt gttatccgct cacaattccc ctatagtgag    5700
tcgtattaat ttcgcgggat cgagatcgat ctcgatcctc tacgccggac gcatcgtggc    5760
cggcatcacc ggcgccacag gtgcggttgc tggcgcctat atcgccgaca tcaccgatgg    5820
ggaagatcgg gctcgccact tcgggctcat gagcgcttgt ttcggcgtgg gtatggtggc    5880
aggccccgtg gccgggggac tgttgggcgc catctccttg catgcaccat tccttgcggc    5940
ggcggtgctc aacggcctca acctactact gggctgcttc ctaatgcagg agtcgcataa    6000
gggagagcgt cgagatcccg gacaccatcg aatggcgcaa aacctttcgc ggtatggcat    6060
gatagcgccc ggaagagagt caattcaggg tggtgaatgt gaaaccagta acgttatacg    6120
atgtcgcaga gtatgccggt gtctcttatc agaccgtttc ccgcgtggtg aaccaggcca    6180
gccacgtttc tgcgaaaacg cgggaaaaag tggaagcggc gatggcggag ctgaattaca    6240
ttcccaaccg cgtggcacaa caactggcgg gcaaacagtc gttgctgatt ggcgttgcca    6300
cctccagtct ggccctgcac gcgccgtcgc aaattgtcgc ggcgattaaa tctcgcgccg    6360
```

```
atcaactggg tgccagcgtg gtggtgtcga tggtagaacg aagcggcgtc gaagcctgta    6420
aagcggcggt gcacaatctt ctcgcgcaac gcgtcagtgg gctgatcatt aactatccgc    6480
tggatgacca ggatgccatt gctgtggaag ctgcctgcac taatgttccg gcgttatttc    6540
ttgatgtctc tgaccagaca cccatcaaca gtattatttt ctcccatgaa gacggtacgc    6600
gactgggcgt ggagcatctg gtcgcattgg gtcaccagca aatcgcgctg ttagcgggcc    6660
cattaagttc tgtctcggcg cgtctgcgtc tggctggctg gcataaatat ctcactcgca    6720
atcaaattca gccgatagcg gaacgggaag gcgactggag tgccatgtcc ggttttcaac    6780
aaaccatgca aatgctgaat gagggcatcg ttcccactgc gatgctggtt gccaacgatc    6840
agatggcgct gggcgcaatg cgcgccatta ccgagtccgg gctgcgcgtt ggtgcggaca    6900
tctcggtagt gggatacgac gataccgaag acagctcatg ttatatcccg ccgttaacca    6960
ccatcaaaca ggattttcgc ctgctggggc aaaccagcgt ggaccgcttg ctgcaactct    7020
ctcagggcca ggcggtgaag ggcaatcagc tgttgcccgt ctcactggtg aaagaaaaa    7080
ccaccctggc gcccaatacg caaaccgcct ctccccgcgc gttggccgat tcattaatgc    7140
agctggcacg acaggtttcc cgactggaaa gcgggcagtg agcgcaacgc aattaatgta    7200
agttagctca ctcattaggc accgggatct cgaccgatgc ccttgagagc cttcaaccca    7260
gtcagctcct tccggtgggc gcggggcatg actatcgtcg ccgcacttat gactgtcttc    7320
tttatcatgc aactcgtagg acaggtgccg gcagcgctct gggtcatttt cggcgaggac    7380
cgctttcgct ggagcgcgac gatgatcggc ctgtcgcttg cggtattcgg aatcttgcac    7440
gccctcgctc aagccttcgt cactggtccc gccaccaaac gtttcggcga agcaggcc    7500
attatcgccg gcatggcggc cccacgggtg cgcatgatcg tgctcctgtc gttgaggacc    7560
cggctaggct ggcggggttg ccttactggt tagcagaatg aatcaccgat acgcgagcga    7620
acgtgaagcg actgctgctg caaaacgtct gcgacctgag caacaacatg aatggtcttc    7680
ggtttccgtg tttcgtaaag tctggaaacg cggaagtcag cgccctgcac cattatgttc    7740
cggatctgca tcgcaggatg ctgctggcta ccctgtggaa cacctacatc tgtattaacg    7800
aagcgctggc attgaccctg agtgattttt ctctggtccc gccgcatcca taccgccagt    7860
tgtttaccct cacaacgttc cagtaaccgg gcatgttcat catcagtaac ccgtatcgtg    7920
agcatcctct ctcgtttcat cggtatcatt acccccatga acagaaatcc cccttacacg    7980
gaggcatcag tgaccaaaca ggaaaaaacc gcccttaaca tggcccgctt tatcagaagc    8040
cagacattaa cgcttctgga gaaactcaac gagctggacg cggatgaaca ggcagacatc    8100
tgtgaatcgc ttcacgacca cgctgatgag ctttaccgca gctgcctcgc gcgtttcggt    8160
gatgacggtg aaaacctctg acacatgcag ctcccggaga cggtcacagc ttgtctgtaa    8220
gcggatgccg ggagcagaca agcccgtcag gcgcgtcag cgggtgttgg cgggtgtcgg    8280
ggcgcagcca tgacccagtc acgtagcgat agcggagtgt atactggctt aactatgcgg    8340
catcagagca gattgtactg agagtgcacc atatatgcgg tgtgaaatac cgcacagatg    8400
cgtaaggaga aaataccgca tcaggcgctc ttccgcttcc tcgctcactg actcgctgcg    8460
ctcggtcgtt cggctgcggc gagcggtatc agctcactca aaggcggtaa tacggttatc    8520
cacagaatca ggggataacg caggaaagaa catgtgagca aaaggccagc aaaaggccag    8580
gaaccgtaaa aaggccgcgt tgctggcgtt tttccatagg ctccgccccc ctgacgagca    8640
tcacaaaaat cgacgctcaa gtcagaggtg gcgaaacccg acaggactat aaagatacca    8700
```

```
ggcgtttccc cctggaagct ccctcgtgcg ctctcctgtt ccgaccctgc cgcttaccgg      8760
atacctgtcc gcctttctcc cttcgggaag cgtggcgctt tctcatagct cacgctgtag      8820
gtatctcagt tcggtgtagg tcgttcgctc caagctgggc tgtgtgcacg aacccccgt       8880 tcagcccgac cgctgcgcct tatccggtaa ctatcgtctt gagtccaacc cggtaagaca      8940
cgacttatcg ccactggcag cagccactgg taacaggatt agcagagcga ggtatgtagg      9000
cggtgctaca gagttcttga agtggtggcc taactacggc tacactagaa ggacagtatt      9060
tggtatctgc gctctgctga agccagttac cttcggaaaa agagttggta gctcttgatc      9120
cggcaaacaa accaccgctg gtagcggtgg ttttttgtt tgcaagcagc agattacgcg        9180
cagaaaaaaa ggatctcaag aagatccttt gatcttttct acggggtctg acgctcagtg      9240
gaacgaaaac tcacgttaag ggattttggt catgaacaat aaaactgtct gcttacataa      9300
acagtaatac aaggggtgtt atgagccata ttcaacggga acgtcttgc tctaggccgc       9360 gattaaattc caacatggat gctgatttat atgggtataa atgggctcgc gataatgtcg      9420
ggcaatcagg tgcgacaatc tatcgattgt atgggaagcc cgatgcgcca gagttgtttc     9480
tgaaacatgg caaaggtagc gttgccaatg atgttacaga tgagatggtc agactaaact     9540
ggctgacgga atttatgcct cttccgacca tcaagcattt tatccgtact cctgatgatg      9600
catggttact caccactgcg atccccggga aaacagcatt ccaggtatta gaagaatatc      9660
ctgattcagg tgaaaatatt gttgatgcgc tggcagtgtt cctgcgccgg ttgcattcga     9720
ttcctgtttg taattgtcct tttaacagcg atcgcgtatt tcgtctcgct caggcgcaat      9780
cacgaatgaa taacggtttg gttgatgcga gtgattttga tgacgagcgt aatggctggc     9840
ctgttgaaca gtctggaaa gaaatgcata aactttgcc attctcaccg gattcagtcg       9900
tcactcatgg tgatttctca cttgataacc ttattttga cgaggggaaa ttaataggtt      9960
gtattgatgt tggacgagtc ggaatcgcag accgatacca ggatcttgcc atcctatgga     10020
actgcctcgg tgagttttct ccttcattac agaaacggct ttttcaaaaa tatggtattg     10080
ataatcctga tatgaataaa ttgcagtttc atttgatgct cgatgagttt ttctaagaat     10140
taattcatga gcggatacat atttgaatgt atttagaaaa ataaacaaat aggggttccg     10200
cgcacatttc cccgaaaagt gccacctgaa attgtaaacg ttaatatttt gttaaaattc     10260
gcgttaaatt tttgttaaat cagctcattt tttaaccaat aggccgaaat cggcaaaatc     10320
ccttataaat caaaagaata accgagata gggttgagtg ttgttccagt ttggaacaag      10380
agtccactat taagaacgt ggactccaac gtcaaaggc gaaaaccgt ctatcagggc        10440 gatggcccac tacgtgaacc atcaccctaa tcaagttttt tggggtcgag gtgccgtaaa     10500
gcactaaatc ggaaccctaa agggagcccc cgatttagag cttgacgggg aaagccggcg     10560
aacgtggcga gaaaggaagg gaagaaagcg aaaggagcgg cgctagggc gctggcaagt      10620 gtagcggtca cgctgcgcgt aaccaccaca cccgccgcgc ttaatgcgcc gctacagggc    10680
gcgtcccatt cgcca                                                      10695

<210> SEQ ID NO 16
<211> LENGTH: 9402
<212> TYPE: DNA
<213> ORGANISM: Artificial Sequence
<220> FEATURE:
<223> OTHER INFORMATION: vector

<400> SEQUENCE: 16
atccggatat agttcctcct ttcagcaaaa aacccctcaa gacccgttta gaggccccaa        60
```

```
ggggttatgc tagttattgc tcagcggtgg cagcagccaa ctcagcttcc tttcgggctt      120
tgttagcagc cggatctcag tggtggtggt ggtggtgctc gagttagtgg tggtggtggt      180
ggtggccacc aggtggattg gaagtcgaag cttgttgaag cacagtgact tcaatagcct      240
tggttgagct tgctgctcca atcatgacgg tagcagtcag cgtgacaacc tgattcccgc      300
ttccatgctg cggtctcgta accgtcccgt cagtcgccac cgtcgacgga tggctggatg      360
cccatgtaag gcttgctcca tgaagccctg cagatggcaa tgagatatgg ttcgttaccg      420
cttgcgccat gtccccgct gcaaaggtta aggaggctgc cgtcagcgca ttcgccgctt       480
cggctgccag ctgctcctca gtaggctgga tcggctcgtt gccaatgatc agactgtcga      540
aggcgagtgc ggcatgaccc acggtgatag cggtaggctc aaatacatac aatcgaatgg      600
atttcagctt ggtggtgtca attgccgctg cctttgcgaa atagccgtct gccagccagc      660
ttgccgcaga gatgccgaaa tccgatatcg taagcgttcg agcttgatta ggagcaattg      720
caaagtaata aatacctcta tgattctcaa cgtcggtaac ctcgacgcga agctgggctc      780
ctgtgttcac gagattcgtg acatccagct gaagcggctt gctgcccagg ctccagcccc      840
cctccggcgc tgtaaaatca atattgccgg aatacttgcc gctcgtatcc cagtcgtatg      900
cggtgaagga atcgaactcc gcatgcagcg ctttgctgcc atgtgtcgcg ccctgttctg      960
atctggtaac ggtaatgtct tggccattag tcgtatagac aacctcttcc tgatcctcga     1020
aggataggaa cacaccgttc ggattgccag gtcctggccc tggatccgat gcactgccaa     1080
ttatgatatg atcaatggca agcgctgcgt tcgtaacagg agcggccgtt ggagaaaaca     1140
caaacagtcg aatcgacttc agattctcgg tatcgatagc tgcgtttctc gggaaattgc     1200
cgtccgcaag ccaagtgcct cccgcaatgc cgaaatcagc aatgctgatg cttcgcgaag     1260
catctgctcc cagcgtgaaa taataagtgc ctttaacgtc cgatgtgtct gtcacctcta     1320
cccgcagctg tgtcgcgtag cttctcagat tcgtaacgtc gaacgtaatg ggtgtagtac     1380
ccaggctcca gccttcctcc ggggcagtaa aatcaaggct gcccgagtac gtacctgttg     1440
tatcccacgc aaaggcagta aaggacgtaa attccgcttg aagtgcctta ctgccgtccg     1500
ttgcgccttg cgagcctgtt gttgtcgtca ccgtgtccac attgtgtgta tacgctgcct     1560
cttctccgtc ctcgaaggag aatttggctc cccgattgcc ggttggagat gattttgttt     1620
tggtatattg atcaaaaata ccagccgctt tggttagatc ctccagcgcc ttcgttattt     1680
catcgtttgt tgctagagca tcctgcgcaa caacctccgc ttttgccacc tcaatgttga     1740
gcgtatcgcg gatatgtttt ttcacccact tctggcctgg ctcaacctca ttgcctgtag     1800
acgatatgat agtagacgca agcttcgact tggcgtccgc aacaggcgca gcaagtgcgc     1860
tggtcgcaat gcctgttgga gccggctgct cgtggtactc gataatctgt acgcttgtaa     1920
tatagccgtc atcgtctgga agcgtaattt caatcgtatt gctcgtcagc agcttgctgg     1980
tgtccaactc aaattccgca aaggtcagca gatttccagg cttatccgta taggccagat     2040
ccttgctgaa gctttgcatg ttggccgtat cacccgaatt tacaaccact tgcatatcct     2100
ctgcaaaccc actgcccgtc ttgccgaagc caatacgaag agtcgctttg gcagagatcag    2160 caggccgcgc ttgaaccgta aatgaggcgg gtgcatttac gctcgtcggc acaagttcct     2220
gaggagcgta tgcaaattct ctctcccatg tttttggtgaa tggaggattg gaatcaagtg    2280
taatctcgaa tacgctcatc tcctgcacac gcatatacac attgttcaga tctgctacat     2340
tcttttgttc ataggtcagg tcgccctct ccaggaagaa atgcttccga gttacgcctg      2400
```

```
caatattagc gcctcccgtg aacacattca gatcaaggtt caccogctgc gagttcagat    2460
tgtgcacggc tacatacacc ttgtcattgt agcggaccgc attcgtgaag acgcgctctt    2520
gatccgcttc agaaggcagg aatgcaccgc gataatcctt ccacatgtcc agatacgctt    2580
ccattggcgt catttcttcc aataatccat tctgtgtttc attatatttg tagaacgtac    2640
ccgtggagtt ggggcgccag ttaatgatgg gatacagata aggaaccagc atgccgattg    2700
tatcggaata attaatgaaa cgcagcatgt agccgttgaa ggccactagc ttctggaagt    2760
aatccgcatc gcttccagcc gtattgtagg tgccttcttc tgtaatatag atcggcttca    2820
cgttatccgt attcgccatg tgagcgttaa gcaggtcaag caccgcttcc attgccccgc    2880
tcaagaagcc atccgagttg ttctctctgt catgaatgaa caggttggca ttttcataga    2940
agtgatgcga ataccaatcc aaggaatctt tcgtgtcatc cataaatttc agctgggcgc    3000
gcgcttcgtc gaaatcattt ttctccaaat acatgaatgc gcttgatggt ccgcccacta    3060
atacgtccgg attctccgcc ttcacttccg cggctacctt gttgtggaac tcggacaaat    3120
agctccacgc ttgctctggc tccgactgga agaaccacca ctcctgcggg atggtcgatt    3180
cgttcttaac ctccacgtac ttgggaccca gtccgtcaaa tctagtatcg atgcttttga    3240
tcagcttggc cgaggcgtcc gccgctgcat cgaagttggc gcgggacggt gtgccgaaat    3300
gctccgattg tccggaatta ggggattccc acatccacct cggccagccg tctagcgtca    3360
ggacataatc cttgccgatg gatggataca gactttcgaa tttgtcgatg gcaggctgac    3420
tcttcgcata aacctcattc gtcgctgtaa agtcagcata tccagggcgc gcaggatctt    3480
ccttaagacc cgcccagctc gtcagtagat tataatgaaa cgcacctcgg ccgggagtaa    3540
agccgtaatc atgagtcgtt ctgtggtacg cctcgtccaa caccgtaaat tcgccgccgg    3600
cttgctctaa gccgatcgga ccactgttca catggtaacg cttgaacact tcctcgggca    3660
gcttatcgac accgtccata cttaagtttg taagcgcatc cacattgacg gacacattca    3720
gaatgtcctt gtctccacca agaacggtcc atgcggaggt gtcgaactcc agcggcacgc    3780
cttcctcttc ccagtggtag acgctgcgaa gcgttccgtt gccgacgatt ttcattttgt    3840
agccttcata aataatgtcg ccgttcgtac ccttaatcag ccaaggatgg gtaatacccct    3900
ccgtcgggtt gtcttcctgg aagcccatct tcgtatagtt ggtatataat ccggtgatgc    3960
cgtccttcca gccgccattc tggaatactg tccaatgtgt ctcgaccccca ttcgggtcaa    4020
tgacatatag ctccatcgtt tgcgcgacgg atccctcgaa gcgcacatca ccgaacagac    4080
gccacactcg cgcatccatg gcaggaatat caaacgttac ctcgccatta atctgcaaat    4140
attgcccatc cgggaattgc aggaagttaa tgcgctgaat ccggctttct ccgttaatac    4200
tgttgaaata agctaccgca ttatcgccga attgtccctt gtaatgctcg gcaacggcag    4260
gaatggtatc gaaatctgcc ttgtcggttc taatattctc aggaagctcg tcgttgacct    4320
ctgccatatg tatatctcct tcttaaagtt aaacaaaatt atttctagag ggaattgtt    4380
atccgctcac aattccccta tagtgagtcg tattaatttc gcgggatcga gatcgatctc    4440
gatcctctac gccggacgca tcgtggccgg catcaccggc gccacaggtg cggttgctgg    4500
cgcctatatc gccgacatca ccgatgggga agatcgggct cgccacttcg ggctcatgag    4560
cgcttgtttc ggcgtgggta tggtggcagg ccccgtggcc gggggactgt gggcgccat    4620
ctccttgcat gcaccattcc ttgcggcggc ggtgctcaac ggcctcaacc tactactggg    4680
ctgcttccta atgcaggagt cgcataaggg agagcgtcga gatcccggac accatcgaat    4740
ggcgcaaaac ctttcgcggt atggcatgat agcgcccgga agagagtcaa ttcagggtgg    4800
```

```
tgaatgtgaa accagtaacg ttatacgatg tcgcagagta tgccggtgtc tcttatcaga    4860
ccgtttcccg cgtggtgaac caggccagcc acgtttctgc gaaaacgcgg gaaaaagtgg    4920
aagcggcgat ggcggagctg aattacattc ccaaccgcgt ggcacaacaa ctggcgggca    4980
aacagtcgtt gctgattggc gttgccacct ccagtctggc cctgcacgcg ccgtcgcaaa    5040
ttgtcgcggc gattaaatct cgcgccgatc aactgggtgc cagcgtggtg gtgtcgatgg    5100
tagaacgaag cggcgtcgaa gcctgtaaag cggcggtgca caatcttctc gcgcaacgcg    5160
tcagtgggct gatcattaac tatccgctgg atgaccagga tgccattgct gtggaagctg    5220
cctgcactaa tgttccggcg ttatttcttg atgtctctga ccagacaccc atcaacagta    5280 ttatttctc ccatgaagac ggtacgcgac tgggcgtgga gcatctggtc gcattgggtc    5340
accagcaaat cgcgctgtta gcgggcccat taagttctgt ctcggcgcgt ctgcgtctgg    5400
ctggctggca taaatatctc actcgcaatc aaattcagcc gatagcggaa cgggaaggcg    5460
actggagtgc catgtccggt tttcaacaaa ccatgcaaat gctgaatgag gcatcgttc    5520 ccactgcgat gctggttgcc aacgatcaga tggcgctggg cgcaatgcgc gccattaccg    5580
agtccgggct gcgcgttggt gcggacatct cggtagtggg atacgacgat accgaagaca    5640
gctcatgtta tccccgccg ttaaccacca tcaaacagga ttttcgcctg ctggggcaaa    5700
ccagcgtgga ccgcttgctg caactctctc agggccaggc ggtgaagggc aatcagctgt    5760
tgcccgtctc actggtgaaa agaaaaacca ccctggcgcc caatacgcaa accgcctctc    5820
cccgcgcgtt ggccgattca ttaatgcagc tggcacgaca ggtttcccga ctggaaagcg    5880
ggcagtgagc gcaacgcaat taatgtaagt tagctcactc attaggcacc gggatctcga    5940
ccgatgccct tgagagcctt caacccagtc agctccttcc ggtgggcgcg gggcatgact    6000
atcgtcgccg cacttatgac tgtcttcttt atcatgcaac tcgtaggaca ggtgccggca    6060
gcgctctggg tcattttcgg cgaggaccgc tttcgctgga gcgcgacgat gatcggcctg    6120
tcgcttgcgg tattcggaat cttgcacgcc ctcgctcaag ccttcgtcac tggtcccgcc    6180
accaaacgtt tcggcgagaa gcaggccatt atcgccggca tggcggcccc acgggtgcgc    6240
atgatcgtgc tcctgtcgtt gaggacccgg ctaggctggc ggggttgcct tactggttag    6300
cagaatgaat caccgatacg cgagcgaacg tgaagcgact gctgctgcaa aacgtctgcg    6360
acctgagcaa caacatgaat ggtcttcggt tccgtgtttt cgtaaagtct ggaaacgcgg    6420
aagtcagcgc cctgcaccat tatgttccgg atctgcatcg caggatgctg ctggctaccc    6480 tgtgaacac ctacatctgt attaacgaag cgctggcatt gaccctgagt gatttttctc    6540
tggtcccgcc gcatccatac cgccagttgt ttaccctcac aacgttccag taaccgggca    6600
tgttcatcat cagtaacccg tatcgtgagc atcctctctc gtttcatcgg tatcattacc    6660
cccatgaaca gaaatccccc ttacacggag gcatcagtga ccaaacagga aaaaaccgcc    6720
cttaacatgg cccgctttat cagaagccag acattaacgc ttctggagaa actcaacgag    6780
ctggacgcgg atgaacaggc agacatctgt gaatcgcttc acgaccacgc tgatgagctt    6840
taccgcagct gcctcgcgcg tttcggtgat gacggtgaaa acctctgaca catgcagctc    6900
ccggagacgg tcacagcttg tctgtaagcg gatgccggga gcagacaagc ccgtcagggc    6960
gcgtcagcgg gtgttggcgg gtgtcggggc gcagccatga cccagtcacg tagcgatagc    7020
ggagtgtata ctggcttaac tatgcggcat cagagcagat tgtactgaga gtgcaccata    7080
tatgcggtgt gaaataccgc acagatgcgt aaggagaaaa taccgcatca ggcgctcttc    7140
```

```
cgcttcctcg ctcactgact cgctgcgctc ggtcgttcgg ctgcggcgag cggtatcagc    7200
tcactcaaag gcggtaatac ggttatccac agaatcaggg gataacgcag aaagaacat     7260
gtgagcaaaa ggccagcaaa aggccaggaa ccgtaaaaag gccgcgttgc tggcgttttt    7320
ccataggctc cgcccccctg acgagcatca aaaaatcga cgctcaagtc agaggtggcg     7380
aaacccgaca ggactataaa gataccaggc gtttccccct ggaagctccc tcgtgcgctc    7440
tcctgttccg accctgccgc ttaccggata cctgtccgcc tttctccctt cgggaagcgt    7500
ggcgctttct catagctcac gctgtaggta tctcagttcg gtgtaggtcg ttcgctccaa    7560
gctgggctgt gtgcacgaac ccccgttca gcccgaccgc tgcgccttat ccggtaacta     7620
tcgtcttgag tccaacccgg taagacacga cttatcgcca ctggcagcag ccactggtaa    7680
caggattagc agagcgaggt atgtaggcgg tgctacagag ttcttgaagt ggtggcctaa    7740
ctacggctac actagaagga cagtatttgg tatctgcgct ctgctgaagc cagttacctt    7800
cggaaaaaga gttggtagct cttgatccgg caaacaaacc accgctggta gcggtggttt    7860
ttttgtttgc aagcagcaga ttacgcgcag aaaaaaagga tctcaagaag atcctttgat    7920
cttttctacg gggtctgacg ctcagtggaa cgaaaactca cgttaaggga ttttggtcat    7980
gaacaataaa actgtctgct tacataaaca gtaatacaag gggtgttatg agccatattc    8040
aacgggaaac gtcttgctct aggccgcgat taaattccaa catggatgct gatttatatg    8100
ggtataaatg ggctcgcgat aatgtcgggc aatcaggtgc gacaatctat cgattgtatg    8160
ggaagcccga tgcgccagag ttgtttctga acatggcaa aggtagcgtt gccaatgatg     8220
ttacagatga gatggtcaga ctaaactggc tgacggaatt tatgcctctt ccgaccatca    8280
agcattttat ccgtactcct gatgatgcat ggttactcac cactgcgatc cccgggaaaa    8340
cagcattcca ggtattagaa gaatatcctg attcaggtga aaatattgtt gatgcgctgg    8400
cagtgttcct gcgccggttg cattcgattc ctgtttgtaa ttgtcctttt aacagcgatc    8460
gcgtatttcg tctcgctcag gcgcaatcac gaatgaataa cggtttggtt gatgcgagtg    8520
attttgatga cgagcgtaat ggctggcctg ttgaacaagt ctggaaagaa atgcataaac    8580
ttttgccatt ctcaccggat tcagtcgtca ctcatggtga tttctcactt gataacctta    8640
tttttgacga ggggaaatta ataggttgta ttgatgttgg acgagtcgga atcgcagacc    8700
gataccagga tcttgccatc ctatggaact gcctcggtga gttttctcct tcattacaga    8760
aacggctttt tcaaaaatat ggtattgata atcctgatat gaataaattg cagtttcatt    8820
tgatgctcga tgagttttc taagaattaa ttcatgagcg gatacatatt tgaatgtatt     8880
tagaaaaata acaaataggg gttccgcgc acatttcccc gaaaagtgcc acctgaaatt     8940
gtaaacgtta atattttgtt aaaattcgcg ttaaattttt gttaaatcag ctcatttttt    9000
aaccaatagg ccgaaatcgg caaaatccct tataaatcaa agaatagac cgagataggg     9060
ttgagtgttg ttccagtttg gaacaagagt ccactattaa agaacgtgga ctccaacgtc    9120
aaagggcgaa aaaccgtcta tcagggcgat ggcccactac gtgaaccatc acctaatca     9180
agttttttgg ggtcgaggtg ccgtaaagca ctaaatcgga accctaaagg agccccccga    9240
tttagagctt gacggggaaa gccggcgaac gtggcgagaa aggaagggaa gaaagcgaaa    9300
ggagcgggcg ctagggcgct ggcaagtgta gcggtcacgc tgcgcgtaac caccacaccc    9360
gccgcgctta atgcgccgct acagggcgcg tcccattcgc ca                      9402
```

<210> SEQ ID NO 17
<211> LENGTH: 9087

<212> TYPE: DNA
<213> ORGANISM: Artificial Sequence
<220> FEATURE:
<223> OTHER INFORMATION: vector

<400> SEQUENCE: 17

| | | | | | |
|---|---|---|---|---|---|
| atccggatat | agttcctcct | ttcagcaaaa | aaccccctcaa | gacccgttta | gaggccccaa | 60 |
| ggggttatgc | tagttattgc | tcagcggtgg | cagcagccaa | ctcagcttcc | tttcgggctt | 120 |
| tgttagcagc | cggatctcag | tggtggtggt | ggtggtgctc | gagttagtgg | tggtggtggt | 180 |
| ggtgagtagg | ctggatcggc | tcgttgccaa | tgatcagact | gtcgaaggcg | agtgcggcat | 240 |
| gacccacggt | gatagcggta | ggctcaaata | catacaatcg | aatggatttc | agcttggtgg | 300 |
| tgtcaattgc | cgctgccttt | gcgaaatagc | cgtctgccag | ccagcttgcc | gcagagatgc | 360 |
| cgaaatccga | tatcgtaagc | gttcgagctt | gattaggagc | aattgcaaag | taataaatac | 420 |
| ctctatgatt | ctcaacgtcg | gtaacctcga | cgcgaagctg | ggctcctgtg | ttcacgagat | 480 |
| tcgtgacatc | cagctgaagc | ggcttgctgc | ccaggctcca | gccccctcc | ggcgctgtaa | 540 |
| aatcaatatt | gccggaatac | ttgccgctcg | tatcccagtc | gtatgcggtg | aaggaatcga | 600 |
| actccgcatg | cagcgctttg | ctgccatgtg | tcgcgcctg | ttctgatctg | gtaacggtaa | 660 |
| tgtcttggcc | attagtcgta | tagacaacct | cttcctgatc | ctcgaaggat | aggaacacac | 720 |
| cgttcggatt | gccaggtcct | ggccctggat | ccgatgcact | gccaattatg | atatgatcaa | 780 |
| tggcaagcgc | tgcgttcgta | acaggagcgg | ccgttggaga | aaacacaaac | agtcgaatcg | 840 |
| acttcagatt | ctcggtatcg | atagctgcgt | ttctcgggaa | attgccgtcc | gcaagccaag | 900 |
| tgcctcccgc | aatgccgaaa | tcagcaatgc | tgatgcttcg | cgaagcatct | gctcccagcg | 960 |
| tgaaataata | agtgccttta | acgtccgatg | tgtctgtcac | ctctacccgc | agctgtgtcg | 1020 |
| cgtagcttct | cagattcgta | acgtcgaacg | taatgggtgt | agtacccagg | ctccagcctt | 1080 |
| cctccgggc | agtaaaatca | aggctgcccg | agtacgtacc | tgttgtatcc | cacgcaaagg | 1140 |
| cagtaaagga | cgtaaattcc | gcttgaagtg | ccttactgcc | gtccgttgcg | ccttgcgagc | 1200 |
| ctgttgttgt | cgtcaccgtg | tccacattgt | gtgtatacgc | tgcctcttct | ccgtcctcga | 1260 |
| aggagaattt | ggctccccga | ttgccggttg | gagatgattt | tgttttggta | tattgatcaa | 1320 |
| aaataccagc | cgctttggtt | agatcctcca | gcgccttcgt | tatttcatcg | tttgttgcta | 1380 |
| gagcatcctg | cgcaacaacc | tccgcttttg | ccacctcaat | gttgagcgta | tcgcggatat | 1440 |
| gttttttcac | ccacttctgg | cctggctcaa | cctcattgcc | tgtagacgat | atgatagtag | 1500 |
| acgcaagctt | cgacttggcg | tccgcaacag | gcgcagcaag | tgcgctggtc | gcaatgcctg | 1560 |
| ttggagccgg | ctgctcgtgg | tactcgataa | tctgtacgct | tgtaatatag | ccgtcatcgt | 1620 |
| ctggaagcgt | aatttcaatc | gtattgctcg | tcagcagctt | gctggtgtcc | aactcaaatt | 1680 |
| ccgcaaaggt | cagcagattt | ccaggcttat | ccgtataggc | cagatccttg | ctgaagcttt | 1740 |
| gcatgttggc | cgtatcaccc | gaatttacaa | ccacttgcat | atcctctgca | aacccactgc | 1800 |
| ccgtcttgcc | gaagccaata | cgaagagtcg | ctttggcgag | atcagcaggc | gcgcgcttgaa | 1860 |
| ccgtaaatga | ggcgggtgca | tttacgctcg | tcggcacaag | ttcctgagga | gcgtatgcaa | 1920 |
| attctctctc | ccatgttttg | gtgaatggag | gattggaatc | aagtgtaatc | tcgaatacgc | 1980 |
| tcatctcctg | cacacgcata | tacacattgt | tcagatctgc | tacattcttt | tgttcatagg | 2040 |
| tcaggtcgcc | cttctccagg | aagaaatgct | tccgagttac | gcctgcaata | ttagcgcctc | 2100 |
| ccgtgaacac | attcagatca | aggttcaccc | gctgcgagtt | cagattgtgc | acggctacat | 2160 |

```
acaccttgtc attgtagcgg accgcattcg tgaagacgcg ctcttgatcc gcttcagaag    2220
gcaggaatgc accgcgataa tccttccaca tgtccagata cgcttccatt ggcgtcattt    2280
cttccaataa tccattctgt gtttcattat atttgtagaa cgtacccgtg gagttggggc    2340
gccagttaat gatgggatac agataaggaa ccagcatgcc gattgtatcg gaataattaa    2400
tgaaacgcag catgtagccg ttgaaggcca ctagcttctg gaagtaatcc gcatcgcttc    2460
cagccgtatt gtaggtgcct tcttctgtaa tatagatcgg cttcacgtta tccgtattcg    2520
ccatgtgagc gttaagcagg tcaagcaccg cttccattcg cccgctcaag aagccatccg    2580
agttgttctc tctgtcatga atgaacaggt tggcattttc atagaagtga tgcgaatacc    2640
aatccaagga atctttcgtg tcatccataa atttcagctg ggcgcgcgct cgtcgaaat    2700
cattttctc caaatacatg aatgcgcttg atggtccgcc cactaatacg tccggattct    2760
ccgccttcac ttccgcggct accttgttgt ggaactcgga caaatagctc cacgcttgct    2820
ctggctccga ctggaagaac caccactcct gcgggatggt cgattcgttc ttaacctcca    2880
cgtacttggg acccagtccg tcaaatctag tatcgatgct tttgatcagc ttggccgagg    2940
cgtccgccgc tgcatcgaag ttggcgcggg acggtgtgcc gaaatgctcc gattgtccgg    3000
aattagggga ttcccacatc caactcggcc agccgtctag cgtcaggaca taatccttgc    3060
cgatggatgg atacagactt tcgaatttgt cgatggcagg ctgactcttc gcataaacct    3120
cattcgtcgc tgtaaagtca gcatatccag ggcgcgcagg atcttcctta agacccgccc    3180
agctcgtcag tagattataa tgaaacgcac ctcggccggg agtaaagccg taatcatgag    3240
tcgttctgtg gtacgcctcg tccaacaccg taaattcgcc gccggcttgc tctaagccga    3300
tcggaccact gttcacatgg taacgcttga acacttcctc gggcagctta cgacaccgt     3360
ccatacttaa gtttgtaagc gcatccacat tgacggacac attcagaatg tccttgtctc    3420
caccaagaac ggtccatgcg gaggtgtcga actccagcgg cacgccttcc tcttcccagt    3480
ggtagacgct gcgaagcgtt ccgttgccga cgattttcat tttgtagcct tcataaataa    3540
tgtcgccgtt cgtacccta atcagccaag gatgggtaat accctccgtc gggttgtctt     3600
cctggaagcc catcttcgta tagttggtat ataatccggt gatgccgtcc ttccagccgc    3660
cattctggaa tactgtccaa tgtgtctcga ccccattcgg gtcaatgaca tatagctcca    3720
tcgtttgcgc gacggatccc tcgaagcgca catcaccgaa cagacgccac actcgcgcat    3780
ccatggcagg aatatcaaac gttacctcgc cattaatctg caaatattgc ccatccggga    3840
attgcaggaa gttaatgcgc tgaatccggc tttctccgtt aatactgttg aaataagcta    3900
ccgcattatc gccgaattgt cccttgtaat gctcggcaac ggcaggaatg gtatcgaaat    3960
ctgccttgtc ggttctaata ttctcaggaa gctcgtcgtt gacctctgcc atatgtatat    4020
ctccttctta aagttaaaca aaattattc tagagggaa ttgttatccg ctcacaattc      4080
ccctatagtg agtcgtatta atttcgcggg atcgagatcg atctcgatcc tctacgccgg    4140
acgcatcgtg gccggcatca ccggcgccac aggtgcggtt gctggcgcct atatcgccga    4200
catcaccgat ggggaagatc gggctcgcca cttcgggctc atgagcgctt gtttcggcgt    4260
gggtatggtg gcaggcccg tggccgggg actgttgggc gccatctcct gcatgcacc       4320
attccttgcg gcggcggtgc tcaacggcct caacctacta ctgggctgct tcctaatgca    4380
ggagtcgcat aagggagagc gtcgagatcc cggacaccat cgaatggcgc aaaacctttc    4440
gcggtatggc atgatagcgc ccggaagaga gtcaattcag ggtggtgaat gtgaaaccag    4500
taacgttata cgatgtcgca gagtatgccg gtgtctctta tcagaccgtt tcccgcgtgg    4560
```

```
tgaaccaggc cagccacgtt tctgcgaaaa cgcgggaaaa agtggaagcg gcgatggcgg    4620
agctgaatta cattcccaac cgcgtggcac aacaactggc gggcaaacag tcgttgctga    4680
ttggcgttgc cacctccagt ctggccctgc acgcgccgtc gcaaattgtc gcggcgatta    4740
aatctcgcgc cgatcaactg ggtgccagcg tggtggtgtc gatggtagaa cgaagcggcg    4800
tcgaagcctg taaagcggcg gtgcacaatc ttctcgcgca acgcgtcagt gggctgatca    4860
ttaactatcc gctggatgac caggatgcca ttgctgtgga agctgcctgc actaatgttc    4920
cggcgttatt tcttgatgtc tctgaccaga cacccatcaa cagtattatt ttctcccatg    4980
aagacggtac gcgactgggc gtggagcatc tggtcgcatt gggtcaccag caaatcgcgc    5040
tgttagcggg cccattaagt tctgtctcgg cgcgtctgcg tctggctggc tggcataaat    5100
atctcactcg caatcaaatt cagccgatag cggaacggga aggcgactgg agtgccatgt    5160
ccggttttca acaaaccatg caaatgctga atgagggcat cgttcccact gcgatgctgg    5220
ttgccaacga tcagtggcg ctgggcgcaa tgcgcgccat taccgagtcc gggctgcgcg    5280
ttggtgcgga catctcggta gtgggatacg acgataccga agacagctca tgttatatcc    5340
cgccgttaac caccatcaaa caggattttc gcctgctggg gcaaaccagc gtggaccgct    5400
tgctgcaact ctctcagggc caggcggtga agggcaatca gctgttgccc gtctcactgg    5460
tgaaaagaaa aaccaccctg cgcccaata cgcaaaccgc ctctccccgc gcgttggccg    5520
attcattaat gcagctggca cgacaggttt cccgactgga aagcgggcag tgagcgcaac    5580
gcaattaatg taagttagct cactcattag gcaccgggat ctcgaccgat gcccttgaga    5640
gccttcaacc cagtcagctc cttccggtgg gcgcggggca tgactatcgt cgccgcactt    5700
atgactgtct tctttatcat gcaactcgta ggacaggtgc cggcagcgct ctgggtcatt    5760
ttcggcgagg accgctttcg ctggagcgcg acgatgatcg gcctgtcgct tgcggtattc    5820
ggaatcttgc acgccctcgc tcaagccttc gtcactggtc cgccaccaa acgtttcggc    5880 gagaagcagg ccattatcgc cggcatggcg gccccacggg tgcgcatgat cgtgctcctg    5940
tcgttgagga cccggctagg ctggcggggt tgccttactg gttagcagaa tgaatcaccg    6000
atacgcgagc gaacgtgaag cgactgctgc tgcaaaacgt ctgcgacctg agcaacaaca    6060
tgaatggtct tcggtttccg tgtttcgtaa agtctggaaa cgcggaagtc agcgccctgc    6120
accattatgt tccggatctg catcgcagga tgctgctggc tacccgtgg aacacctaca    6180 tctgtattaa cgaagcgctg gcattgaccc tgagtgattt ttctctggtc ccgccgcatc    6240
cataccgcca gttgtttacc ctcacaacgt tccagtaacc gggcatgttc atcatcagta    6300
acccgtatcg tgagcatcct ctctcgtttc atcggtatca ttaccccat gaacagaaat    6360 cccccttaca cggaggcatc agtgaccaaa caggaaaaaa ccgcccttaa catggcccgc    6420
tttatcagaa gccagacatt aacgcttctg gagaaactca acgagctgga cgcggatgaa    6480
caggcagaca tctgtgaatc gcttcacgac cacgctgatg agctttaccg cagctgcctc    6540
gcgcgtttcg gtgatgacgg tgaaaacctc tgacacatgc agctcccgga cggtcaca    6600 gcttgtctgt aagcggatgc cgggagcaga caagcccgtc agggcgcgtc agcgggtgtt    6660
ggcgggtgtc ggggcgcagc catgacccag tcacgtagcg atagcggagt gtatactggc    6720
ttaactatgc ggcatcagag cagattgtac tgagagtgca ccatatatgc ggtgtgaaat    6780
accgcacaga tgcgtaagga gaaaataccg catcaggcgc tcttccgctt cctcgctcac    6840
tgactcgctg cgctcggtcg ttcggctgcg gcgagcggta tcagctcact caaaggcggt    6900
```

```
aatacggtta tccacagaat caggggataa cgcaggaaag aacatgtgag caaaaggcca    6960
gcaaaaggcc aggaaccgta aaaaggccgc gttgctggcg ttttttccata ggctccgccc    7020 ccctgacgag catcacaaaa atcgacgctc aagtcagagg tggcgaaacc cgacaggact    7080
ataaagatac caggcgtttc ccctggaag ctccctcgtg cgctctcctg ttccgaccct     7140
gccgcttacc ggatacctgt ccgcctttct cccttcggga agcgtggcgc tttctcatag    7200
ctcacgctgt aggtatctca gttcggtgta ggtcgttcgc tccaagctgg gctgtgtgca    7260 cgaaccccc gttcagcccg accgctgcgc cttatccggt aactatcgtc ttgagtccaa     7320
cccggtaaga cacgacttat cgccactggc agcagccact ggtaacagga ttagcagagc    7380
gaggtatgta ggcggtgcta cagagttctt gaagtggtgg cctaactacg gctacactag    7440
aaggacagta tttggtatct gcgctctgct gaagccagtt accttcggaa aaagagttgg    7500
tagctcttga tccggcaaac aaaccaccgc tggtagcggt ggtttttttg tttgcaagca    7560
gcagattacg cgcagaaaaa aaggatctca agaagatcct ttgatctttt ctacggggtc    7620
tgacgctcag tggaacgaaa actcacgtta agggattttg gtcatgaaca ataaaactgt    7680
ctgcttacat aaacagtaat acaaggggtg ttatgagcca tattcaacgg gaaacgtctt    7740
gctctaggcc gcgattaaat tccaacatgg atgctgattt atatgggtat aaatgggctc    7800
gcgataatgt cgggcaatca ggtgcgacaa tctatcgatt gtatgggaag cccgatgcgc    7860
cagagttgtt tctgaaacat ggcaaaggta gcgttgccaa tgatgttaca gatgagatgg    7920
tcagactaaa ctggctgacg gaatttatgc ctcttccgac catcaagcat tttatccgta    7980
ctcctgatga tgcatggtta ctcaccactg cgatccccgg aaaacagca ttccaggtat     8040 tagaagaata tcctgattca ggtgaaaata ttgttgatgc gctggcagtg ttcctgcgcc    8100
ggttgcattc gattcctgtt tgtaattgtc cttttaacag cgatcgcgta tttcgtctcg    8160
ctcaggcgca atcacgaatg aataacggtt tggttgatgc gagtgatttt gatgacgagc    8220
gtaatggctg gcctgttgaa caagtctgga agaaatgca taaactttg ccattctcac      8280 cggattcagt cgtcactcat ggtgatttct cacttgataa ccttattttt gacgagggga    8340
aattaatagg ttgtattgat gttggacgag tcggaatcgc agaccgatac caggatcttg    8400
ccatcctatg aactgcctc ggtgagtttt ctccttcatt acagaaacgg ctttttcaaa     8460
aatatggtat tgataatcct gatatgaata aattgcagtt tcatttgatg ctcgatgagt    8520
ttttctaaga attaattcat gagcggatac atatttgaat gtatttagaa aaataaacaa    8580
ataggggttc cgcgcacatt tccccgaaaa gtgccacctg aaattgtaaa cgttaatatt    8640
ttgttaaaat tcgcgttaaa ttttttgttaa atcagctcat tttttaacca ataggccgaa    8700
atcggcaaaa tcccttataa atcaaaagaa tagaccgaga tagggttgag tgttgttcca    8760
gtttggaaca agagtccact attaaagaac gtggactcca acgtcaaagg gcgaaaaacc    8820
gtctatcagg gcgatggccc actacgtgaa ccatcaccct aatcaagttt ttggggtcg     8880 aggtgccgta agcactaaa tcggaacccct aaagggagcc cccgatttag agcttgacgg    8940
ggaaagccgg cgaacgtggc gagaaaggaa gggaagaaag cgaaaggagc gggcgctagg    9000
gcgctggcaa gtgtagcggt cacgctgcgc gtaaccacca cacccgccgc gcttaatgcg    9060
ccgctacagg gcgcgtccca ttcgcca                                        9087
```

<210> SEQ ID NO 18
<211> LENGTH: 8550
<212> TYPE: DNA
<213> ORGANISM: Artificial Sequence
<220> FEATURE:
<223> OTHER INFORMATION: vector

<400> SEQUENCE: 18

```
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagttagtgg tggtggtggt     180
ggtggttcgg attgccaggt cctggccctg gatccgatgc actgccaatt atgatatgat     240
caatggcaag cgctgcgttc gtaacaggag cggccgttgg agaaaacaca acagtcgaa      300
tcgacttcag attctcggta tcgatagctg cgtttctcgg gaaattgccg tccgcaagcc     360
aagtgcctcc cgcaatgccg aaatcagcaa tgctgatgct tcgcgaagca tctgctccca     420
gcgtgaaata ataagtgcct ttaacgtccg atgtgtctgt cacctctacc cgcagctgtg     480
tcgcgtagct tctcagattc gtaacgtcga acgtaatggg tgtagtaccc aggctccagc     540
cttcctccgg ggcagtaaaa tcaaggctgc ccgagtacgt acctgttgta tcccacgcaa     600
aggcagtaaa ggacgtaaat tccgcttgaa gtgccttact gccgtccgtt gcgccttgcg     660
agcctgttgt tgtcgtcacc gtgtccacat tgtgtgtata cgctgcctct tctccgtcct     720
cgaaggagaa tttggctccc cgattgccgg ttggagatga ttttgttttg gtatattgat     780
caaaaatacc agccgctttg gttagatcct ccagcgcctt cgttatttca tcgtttgttg     840
ctagagcatc ctgcgcaaca acctccgctt ttgccacctc aatgttgagc gtatcgcgga     900
tatgttttt cacccacttc tggcctggct caacctcatt gcctgtagac gatatgatag     960
tagacgcaag cttcgacttg gcgtccgcaa caggcgcagc aagtgcgctg tcgcaatgc    1020
ctgttggagc cggctgctcg tggtactcga taatctgtac gcttgtaata tagccgtcat    1080
cgtctggaag cgtaatttca atcgtattgc tcgtcagcag cttgctggtg tccaactcaa    1140
attccgcaaa ggtcagcaga tttccaggct tatccgtata ggccagatcc ttgctgaagc    1200
tttgcatgtt ggccgtatca cccgaattta caaccacttg catatcctct gcaaacccac    1260
tgcccgtctt gccgaagcca atacgaagag tcgctttggc gagatcagca ggccgcgctt    1320
gaaccgtaaa tgaggcgggt gcatttacgc tcgtcggcac aagttcctga ggagcgtatg    1380
caaattctct ctcccatgtt ttggtgaatg gaggattgga atcaagtgta atctcgaata    1440
cgctcatctc ctgcacacgc atatacacat tgttcagatc tgctacattc ttttgttcat    1500
aggtcaggtc gcccttctcc aggaagaaat gcttccgagt tacgcctgca atattagcgc    1560
ctcccgtgaa cacattcaga tcaaggttca cccgctgcga gttcagattg tgcacggcta    1620
catacacctt gtcattgtag cggaccgcat tcgtgaagac gcgctcttga tccgcttcag    1680
aaggcaggaa tgcaccgcga taatccttcc acatgtccag atacgcttcc attggcgtca    1740
tttcttccaa taatccattc tgtgtttcat tatatttgta gaacgtaccc gtggagttgg    1800
ggcgccagtt aatgatggga tacagataag gaaccagcat gccgattgta tcggaataat    1860
taatgaaacg cagcatgtag ccgttgaagg ccactagctt ctggaagtaa tccgcatcgc    1920
ttccagccgt attgtaggtg ccttcttctg taatatagat cggcttcacg ttatccgtat    1980
tcgccatgtg agcgttaagc aggtcaagca ccgcttccat tcgcccgctc aagaagccat    2040
ccgagttgtt ctctctgtca tgaatgaaca ggttggcatt ttcatagaag tgatgcgaat    2100
accaatccaa ggaatctttc gtgtcatcca taaatttcag ctgggcgcgc gcttcgtcga    2160
aatcattttt ctccaaatac atgaatgcgc ttgatggtcc gcccactaat acgtccggat    2220
```

```
tctccgcctt cacttccgcg gctaccttgt tgtggaactc ggacaaatag ctccacgctt    2280
gctctggctc cgactggaag aaccaccact cctgcgggat ggtcgattcg ttcttaacct    2340
ccacgtactt gggacccagt ccgtcaaatc tagtatcgat gcttttgatc agcttggccg    2400
aggcgtccgc cgctgcatcg aagttggcgc gggacggtgt gccgaaatgc tccgattgtc    2460
cggaattagg ggattcccac atccacctcg gccagccgtc tagcgtcagg acataatcct    2520
tgccgatgga tggatacaga ctttcgaatt tgtcgatggc aggctgactc ttcgcataaa    2580
cctcattcgt cgctgtaaag tcagcatatc cagggcgcgc aggatcttcc ttaagacccg    2640
cccagctcgt cagtagatta taatgaaacg caccctcggcc gggagtaaag ccgtaatcat    2700
gagtcgttct gtggtacgcc tcgtccaaca ccgtaaattc gccgccggct tgctctaagc    2760
cgatcggacc actgttcaca tggtaacgct tgaacacttc ctcgggcagc ttatcgacac    2820
cgtccatact taagtttgta agcgcatcca cattgacgga cacattcaga atgtccttgt    2880
ctccaccaag aacggtccat gcggaggtgt cgaactccag cggcacgcct tcctcttccc    2940
agtggtagac gctgcgaagc gttccgttgc cgacgatttt cattttgtag ccttcataaa    3000
taatgtcgcc gttcgtaccc ttaatcagcc aaggatgggt aataccctcc gtcgggttgt    3060
cttcctggaa gcccatcttc gtatagttgg tatataatcc ggtgatgccg tccttccagc    3120
cgccattctg gaatactgtc caatgtgtct cgaccccatt cgggtcaatg acatatagct    3180
ccatcgtttg cgcgacggat ccctcgaagc gcacatcacc gaacagacgc cacactcgcg    3240
catccatggc aggaatatca aacgttacct cgccattaat ctgcaaatat gcccatccg    3300 ggaattgcag gaagttaatg cgctgaatcc ggctttctcc gttaatactg ttgaaataag    3360
ctaccgcatt atcgccgaat tgtcccttgt aatgctcggc aacggcagga atggtatcga    3420
aatctgcctt gtcggttcta atattctcag gaagctcgtc gttgacctct gccatatgta    3480
tatctccttc ttaaagttaa acaaaattat ttctagaggg gaattgttat ccgctcacaa    3540 ttccctata gtgagtcgta ttaatttcgc gggatcgaga tcgatctcga tcctctacgc    3600
cggacgcatc gtggccggca tcaccggcgc cacaggtgcg gttgctggcg cctatatcgc    3660
cgacatcacc gatggggaag atcgggctcg ccacttcggg ctcatgagcg cttgtttcgg    3720
cgtgggtatg gtggcaggcc ccgtggccgg gggactgttg ggcgccatct ccttgcatgc    3780
accattcctt gcggcggcgg tgctcaacgg cctcaaccta ctactgggct gcttcctaat    3840
gcaggagtcg cataagggag agcgtcgaga tcccggacac catcgaatgg cgcaaaacct    3900
ttcgcggtat ggcatgatag cgcccggaag agagtcaatt cagggtggtg aatgtgaaac    3960
cagtaacgtt atacgatgtc gcagagtatg ccggtgtctc ttatcagacc gtttcccgcg    4020
tggtgaacca ggccagccac gtttctgcga aaacgcggga aaaagtggaa gcggcgatgg    4080
cggagctgaa ttacattccc aaccgcgtgg cacaacaact ggcgggcaaa cagtcgttgc    4140
tgattggcgt tgccacctcc agtctggccc tgcacgcgcc gtcgcaaatt gtcgcggcga    4200
ttaaatctcg cgccgatcaa ctgggtgcca gcgtggtggt gtcgatggta gaacgaagcg    4260
gcgtcgaagc ctgtaaagcg gcggtgcaca atcttctcgc gcaacgcgtc agtgggctga    4320
tcattaacta tccgctggat gaccaggatg ccattgctgt ggaagctgcc tgcactaatg    4380
ttccggcgtt atttcttgat gtctctgacc agacacccat caacagtatt attttctccc    4440
atgaagacgg tacgcgactg ggcgtggagc atctggtcgc attgggtcac cagcaaatcg    4500
cgctgttagc gggcccatta agttctgtct cggcgcgtct gcgtctggct ggctggcata    4560
aatatctcac tcgcaatcaa attcagccga tagcggaacg ggaaggcgac tggagtgcca    4620
```

```
tgtccggttt tcaacaaacc atgcaaatgc tgaatgaggg catcgttccc actgcgatgc    4680
tggttgccaa cgatcagatg gcgctgggcg caatgcgcgc cattaccgag tccgggctgc    4740
gcgttggtgc ggacatctcg gtagtgggat acgacgatac cgaagacagc tcatgttata    4800
tcccgccgtt aaccaccatc aaacaggatt ttcgcctgct ggggcaaacc agcgtggacc    4860
gcttgctgca actctctcag ggccaggcgg tgaagggcaa tcagctgttg cccgtctcac    4920
tggtgaaaag aaaaaccacc ctggcgccca atacgcaaac cgcctctccc cgcgcgttgg    4980
ccgattcatt aatgcagctg gcacgacagg tttcccgact ggaaagcggg cagtgagcgc    5040
aacgcaatta atgtaagtta gctcactcat taggcaccgg gatctcgacc gatgcccttg    5100
agagccttca acccagtcag ctccttccgg tgggcgcggg gcatgactat cgtcgccgca    5160
cttatgactg tcttctttat catgcaactc gtaggacagg tgccggcagc gctctgggtc    5220
attttcggcg aggaccgctt tcgctggagc gcgacgatga tcggcctgtc gcttgcggta    5280
ttcggaatct tgcacgccct cgctcaagcc ttcgtcactg gtcccgccac caaacgtttc    5340
ggcgagaagc aggccattat cgccggcatg gcggccccac gggtgcgcat gatcgtgctc    5400
ctgtcgttga gacccggct aggctggcgg ggttgcctta ctggttagca gaatgaatca    5460
ccgatacgcg agcgaacgtg aagcgactgc tgctgcaaaa cgtctgcgac ctgagcaaca    5520
acatgaatgt cttcggtttt ccgtgtttcg taaagtctgg aaacgcggaa gtcagcgccc    5580
tgcaccatta tgttccggat ctgcatcgca ggatgctgct ggctaccctg tggaacacct    5640
acatctgtat taacgaagcg ctggcattga ccctgagtga ttttctctg gtcccgccgc    5700 atccataccg ccagttgttt accctcacaa cgttccagta accgggcatg ttcatcatca    5760
gtaacccgta tcgtgagcat cctctctcgt ttcatcggta tcattacccc catgaacaga    5820
aatccccctt acacggaggc atcagtgacc aaacaggaaa aaaccgccct taacatggcc    5880
cgctttatca gaagccagac attaacgctt ctggagaaac tcaacgagct ggacgcggat    5940
gaacaggcag acatctgtga atcgcttcac gaccacgctg atgagcttta ccgcagctgc    6000
ctcgcgcgtt tcggtgatga cggtgaaaac ctctgacaca tgcagctccc ggagacggtc    6060
acagcttgtc tgtaagcgga tgccgggagc agacaagccc gtcagggcgc gtcagcgggt    6120
gttggcgggt gtcggggcgc agccatgacc cagtcacgta gcgatagcgg agtgtatact    6180
ggcttaacta tgcggcatca gagcagattg tactgagagt gcaccatata tgcggtgtga    6240
aataccgcac agatgcgtaa ggagaaaata ccgcatcagg cgctcttccg cttcctcgct    6300
cactgactcg ctgcgctcgg tcgttcggct gcggcgagcg gtatcagctc actcaaaggc    6360
ggtaatacgg ttatccacag aatcagggga taacgcagga agaacatgt gagcaaaagg    6420 ccagcaaaag gccaggaacc gtaaaaaggc cgcgttgctg gcgttttttcc ataggctccg    6480 ccccccctgac gagcatcaca aaaatcgacg ctcaagtcag aggtggcgaa acccgacagg    6540
actataaaga taccaggcgt ttccccctgg aagctccctc gtgcgctctc ctgttccgac    6600
cctgccgctt accggatacc tgtccgcctt tctcccttcg ggaagcgtgg cgctttctca    6660
tagctcacgc tgtaggtatc tcagttcggt gtaggtcgtt cgctccaagc tgggctgtgt    6720
gcacgaaccc cccgttcagc ccgaccgctg cgccttatcc ggtaactatc gtcttgagtc    6780
caacccggta agacacgact tatcgccact ggcagcagcc actggtaaca ggattagcag    6840
agcgaggtat gtaggcggtg ctacagagtt cttgaagtgg tggcctaact acggctacac    6900
tagaaggaca gtatttggta tctgcgctct gctgaagcca gttaccttcg gaaaaagagt    6960
```

```
tggtagctct tgatccggca aacaaaccac cgctggtagc ggtggttttt ttgtttgcaa    7020
gcagcagatt acgcgcagaa aaaaggatc tcaagaagat cctttgatct tttctacggg    7080
gtctgacgct cagtggaacg aaaactcacg ttaagggatt ttggtcatga acaataaaac    7140
tgtctgctta cataaacagt aatacaaggg gtgttatgag ccatattcaa cgggaaacgt    7200
cttgctctag gccgcgatta aattccaaca tggatgctga tttatatggg tataaatggg    7260
ctcgcgataa tgtcgggcaa tcaggtgcga caatctatcg attgtatggg aagcccgatg    7320
cgccagagtt gtttctgaaa catggcaaag gtagcgttgc caatgatgtt acagatgaga    7380
tggtcagact aaactggctg acggaattta tgcctcttcc gaccatcaag cattttatcc    7440
gtactcctga tgatgcatgg ttactcacca ctgcgatccc cgggaaaaca gcattccagg    7500
tattagaaga atatcctgat tcaggtgaaa atattgttga tgcgctggca gtgttcctgc    7560
gccggttgca ttcgattcct gtttgtaatt gtccttttaa cagcgatcgc gtatttcgtc    7620
tcgctcaggc gcaatcacga atgaataacg gtttggttga tgcgagtgat tttgatgacg    7680
agcgtaatgg ctggcctgtt gaacaagtct ggaaagaaat gcataaactt ttgccattct    7740
caccggattc agtcgtcact catggtgatt tctcacttga taaccttatt tttgacgagg    7800
ggaaattaat aggttgtatt gatgttggac gagtcggaat cgcagaccga taccaggatc    7860
ttgccatcct atggaactgc ctcggtgagt tttctccttc attacagaaa cggctttttc    7920
aaaaatatgg tattgataat cctgatatga ataaattgca gtttcatttg atgctcgatg    7980
agttttttcta gaattaatt catgagcgga tacatatttg aatgtattta gaaaaataaa    8040
caaatagggg ttccgcgcac atttccccga aaagtgccac ctgaaattgt aaacgttaat    8100
attttgttaa aattcgcgtt aaattttttgt taaatcagct cattttttaa ccaataggcc    8160
gaaatcggca aaatccctta taaatcaaaa gaatagaccg agatagggtt gagtgttgtt    8220
ccagtttgga acaagagtcc actattaaag aacgtggact ccaacgtcaa agggcgaaaa    8280
accgtctatc agggcgatgg cccactacgt gaaccatcac cctaatcaag ttttttgggg    8340
tcgaggtgcc gtaaagcact aaatcggaac cctaaaggga gcccccgatt tagagcttga    8400
cggggaaagc cggcgaacgt ggcgagaaag gaagggaaga agcgaaagg agcgggcgct    8460
agggcgctgg caagtgtagc ggtcacgctg cgcgtaacca ccacacccgc cgcgcttaat    8520
gcgccgctac agggcgcgtc ccattcgcca                                    8550

<210> SEQ ID NO 19
<211> LENGTH: 8187
<212> TYPE: DNA
<213> ORGANISM: Artificial Sequence
<220> FEATURE:
<223> OTHER INFORMATION: vector

<400> SEQUENCE: 19
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagttagtgg tggtggtggt    180
ggtgcgggga agtaaaatca aggctgcccg agtacgtacc tgttgtatcc cacgcaaagg    240
cagtaaagga cgtaaattcc gcttgaagtg ccttactgcc gtccgttgcg ccttgcgagc    300
ctgttgttgt cgtcaccgtg tccacattgt gtgtatacgc tgcctcttct ccgtcctcga    360
aggagaattt ggctccccga ttgccggttg gagatgattt tgtttggta tattgatcaa    420
aaataccagc cgctttggtt agatcctcca gcgccttcgt tatttcatcg tttgttgcta    480
```

```
gagcatcctg cgcaacaacc tccgcttttg ccacctcaat gttgagcgta tcgcggatat   540 gtttttcac  ccacttctgg cctggctcaa cctcattgcc tgtagacgat atgatagtag   600
acgcaagctt cgacttggcg tccgcaacag gcgcagcaag tgcgctggtc gcaatgcctg   660
ttggagccgg ctgctcgtgg tactcgataa tctgtacgct tgtaatatag ccgtcatcgt   720
ctggaagcgt aatttcaatc gtattgctcg tcagcagctt gctggtgtcc aactcaaatt   780
ccgcaaaggt cagcagattt ccaggcttat ccgtataggc cagatccttg ctgaagcttt   840
gcatgttggc cgtatcaccc gaatttacaa ccacttgcat atcctctgca aacccactgc   900
ccgtcttgcc gaagccaata cgaagagtcg ctttggcgag atcagcaggc cgcgcttgaa   960
ccgtaaatga ggcgggtgca tttacgctcg tcggcacaag ttcctgagga gcgtatgcaa  1020
attctctctc ccatgttttg gtgaatggag gattggaatc aagtgtaatc tcgaatacgc  1080
tcatctcctg cacacgcata tacacattgt tcagatctgc tacattcttt tgttcatagg  1140
tcaggtcgcc cttctccagg aagaaatgct tccgagttac gcctgcaata ttagcgcctc  1200
ccgtgaacac attcagatca aggttcaccc gctgcgagtt cagattgtgc acggctacat  1260
acaccttgtc attgtagcgg accgcattcg tgaagacgcg ctcttgatcc gcttcagaag  1320
gcaggaatgc accgcgataa tccttccaca tgtccagata cgcttccatt ggcgtcattt  1380
cttccaataa tccattctgt gtttcattat atttgtagaa cgtacccgtg agttggggc   1440 gccagttaat gatgggatac agataaggaa ccagcatgcc gattgtatcg gaataattaa  1500
tgaaacgcag catgtagccg ttgaaggcca ctagcttctg gaagtaatcc gcatcgcttc  1560
cagccgtatt gtaggtgcct tcttctgtaa tatagatcgg cttcacgtta tccgtattcg  1620
ccatgtgagc gttaagcagg tcaagcaccg cttccattcg cccgctcaag aagccatccg  1680
agttgttctc tctgtcatga atgaacaggt tggcatttc atagaagtga tgcgaatacc  1740
aatccaagga atctttcgtg tcatccataa atttcagctg ggcgcgcgct tcgtcgaaat  1800 cattttctc  caaatacatg aatgcgcttg atggtccgcc cactaatacg tccggattct  1860
ccgccttcac ttccgcggct accttgttgt ggaactcgga caaatagctc cacgcttgct  1920
ctggctccga ctgaagaaac caccactcct gcgggatggt cgattcgttc ttaacctcca  1980
cgtacttggg acccagtccg tcaaatctag tatcgatgct tttgatcagc ttggccgagg  2040
cgtccgccgc tgcatcgaag ttggcgcggg acggtgtgcc gaaatgctcc gattgtccgg  2100
aattagggga ttcccacatc cacctcggcc agccgtctag cgtcaggaca taatccttgc  2160
cgatggatgg atacagactt tcgaatttgt cgatggcagg ctgactcttc gcataaacct  2220
cattcgtcgc tgtaaagtca gcatatccag ggcgcgcagg atcttcctta agacccgccc  2280
agctcgtcag tagattataa tgaaacgcac ctcggccggg agtaaagccg taatcatgag  2340
tcgttctgtg gtacgcctcg tccaacaccg taaattcgcc gccggcttgc tctaagccga  2400
tcggaccact gttcacatgg taacgcttga acacttcctc gggcagctta tcgacaccgt  2460
ccatacttaa gtttgtaagc gcatccacat tgacggacac attcagaatg tccttgtctc  2520
caccaagaac ggtccatgcg gaggtgtcga actccagcgg cacgccttcc tcttcccagt  2580
ggtagacgct gcgaagcgtt ccgttgccga cgattttcat tttgtagcct tcataaataa  2640
tgtcgccgtt cgtacccta  atcagccaag gatgggtaat accctccgtc gggttgtctt  2700
cctggaagcc catcttcgta tagttggtat ataatccggt gatgccgtcc ttccagccgc  2760
cattctggaa tactgtccaa tgtgtctcga ccccattcgg gtcaatgaca tatagctcca  2820
```

```
tcgtttgcgc gacggatccc tcgaagcgca catcaccgaa cagacgccac actcgcgcat    2880
ccatggcagg aatatcaaac gttacctcgc cattaatctg caaatattgc ccatccggga    2940
attgcaggaa gttaatgcgc tgaatccggc tttctccgtt aatactgttg aaataagcta    3000
ccgcattatc gccgaattgt cccttgtaat gctcggcaac ggcaggaatg gtatcgaaat    3060
ctgccttgtc ggttctaata ttctcaggaa gctcgtcgtt gacctctgcc atatgtatat    3120
ctccttctta aagttaaaca aaattatttc tagaggggaa ttgttatccg ctcacaattc    3180
ccctatagtg agtcgtatta atttcgcggg atcgagatcg atctcgatcc tctacgccgg    3240
acgcatcgtg gccggcatca ccggcgccac aggtgcggtt gctggcgcct atatcgccga    3300
catcaccgat ggggaagatc gggctcgcca cttcgggctc atgagcgctt gtttcggcgt    3360
gggtatggtg gcaggccccg tggccggggg actgttgggc gccatctcct tgcatgcacc    3420
attccttgcg gcggcggtgc tcaacggcct caacctacta ctgggctgct tcctaatgca    3480
ggagtcgcat aagggagagc gtcgagatcc cggacaccat cgaatggcgc aaaacctttc    3540
gcggtatggc atgatagcgc ccggaagaga gtcaattcag gtggtgaat gtgaaaccag    3600
taacgttata cgatgtcgca gagtatgccg gtgtctctta tcagaccgtt tcccgcgtgg    3660
tgaaccaggc cagccacgtt tctgcgaaaa cgcgggaaaa agtggaagcg gcgatggcgg    3720
agctgaatta cattcccaac cgcgtggcac aacaactggc gggcaaacag tcgttgctga    3780
ttggcgttgc cacctccagt ctggccctgc acgcgccgtc gcaaattgtc gcggcgatta    3840
aatctcgcgc cgatcaactg ggtgccagcg tggtggtgtc gatggtagaa cgaagcggcg    3900
tcgaagcctg taaagcggcg gtgcacaatc ttctcgcgca acgcgtcagt gggctgatca    3960
ttaactatcc gctggatgac caggatgcca ttgctgtgga agctgcctgc actaatgttc    4020
cggcgttatt tcttgatgtc tctgaccaga cacccatcaa cagtattatt ttctcccatg    4080
aagacggtac gcgactgggc gtggagcatc tggtcgcatt gggtcaccag caaatcgcgc    4140
tgttagcggg cccattaagt tctgtctcgg cgcgtctgcg tctggctggc tggcataaat    4200
atctcactcg caatcaaatt cagccgatag cggaacggga aggcgactgg agtgccatgt    4260
ccggttttca acaaaccatg caaatgctga atgagggcat cgttcccact gcgatgctgg    4320
ttgccaacga tcagatggcg ctgggcgcaa tgcgcgccat taccgagtcc gggctgcgcg    4380
ttggtgcgga catctcggta gtgggatacg acgataccga agacagctca tgttatatcc    4440
cgccgttaac caccatcaaa caggattttc gcctgctggg gcaaaccagc gtggaccgct    4500
tgctgcaact ctctcagggc caggcggtga agggcaatca gctgttgccc gtctcactgg    4560
tgaaaagaaa aaccaccctg gcgcccaata cgcaaaccgc ctctccccgc gcgttggccg    4620
attcattaat gcagctggca cgacaggttt cccgactgga aagcgggcag tgagcgcaac    4680
gcaattaatg taagttagct cactcattag gcaccgggat ctcgaccgat gcccttgaga    4740
gccttcaacc cagtcagctc cttccggtgg gcgcggggca tgactatcgt cgccgcactt    4800
atgactgtct tctttatcat gcaactcgta ggacaggtgc cggcagcgct ctgggtcatt    4860
ttcggcgagg accgctttcg ctggagcgcg acgatgatcg gcctgtcgct tgcggtattc    4920
ggaatcttgc acgccctcgc tcaagccttc gtcactggtc cgccaccaa acgtttcggc    4980
gagaagcagg ccattatcgc cggcatggcg gccccacggg tgcgcatgat cgtgctcctg    5040
tcgttgagga cccggctagg ctggcggggt tgccttactg gttagcagaa tgaatcaccg    5100
atacgcgagc gaacgtgaag cgactgctgc tgcaaaacgt ctgcgacctg agcaacaaca    5160
tgaatggtct tcggtttccg tgtttcgtaa agtctggaaa cgcggaagtc agcgccctgc    5220
```

```
accattatgt tccggatctg catcgcagga tgctgctggc tacccgtgtg aacacctaca    5280
tctgtattaa cgaagcgctg gcattgaccc tgagtgattt ttctctggtc ccgccgcatc    5340
cataccgcca gttgtttacc ctcacaacgt tccagtaacc gggcatgttc atcatcagta    5400
acccgtatcg tgagcatcct ctctcgtttc atcggtatca ttaccccat gaacagaaat     5460 ccccttaca cggaggcatc agtgaccaaa caggaaaaaa ccgcccttaa catggcccgc     5520
tttatcagaa gccagacatt aacgcttctg gagaaactca acgagctgga cgcggatgaa    5580
caggcagaca tctgtgaatc gcttcacgac cacgctgatg agctttaccg cagctgcctc    5640
gcgcgtttcg gtgatgacgg tgaaaacctc tgacacatgc agctcccgga gacggtcaca    5700
gcttgtctgt aagcggatgc cgggagcaga caagcccgtc agggcgcgtc agcgggtgtt    5760
ggcgggtgtc ggggcgcagc catgacccag tcacgtagcg atagcggagt gtatactggc    5820
ttaactatgc ggcatcagag cagattgtac tgagagtgca ccatatatgc ggtgtgaaat    5880
accgcacaga tgcgtaagga gaaaataccg catcaggcgc tcttccgctt cctcgctcac    5940
tgactcgctg cgctcggtcg ttcggctgcg gcgagcggta tcagctcact caaaggcggt    6000
aatacggtta tccacagaat caggggataa cgcaggaaag aacatgtgag caaaaggcca    6060
gcaaaaggcc aggaaccgta aaaaggccgc gttgctggcg ttttccata ggctccgccc     6120 ccctgacgag catcacaaaa atcgacgctc aagtcagagg tggcgaaacc cgacaggact    6180
ataaagatac caggcgtttc cccctggaag ctccctcgtg cgctctcctg ttccgaccct    6240
gccgcttacc ggatacctgt ccgcctttct cccttcggga agcgtggcgc tttctcatag    6300
ctcacgctgt aggtatctca gttcggtgta ggtcgttcgc tccaagctgg gctgtgtgca    6360 cgaaccccc gttcagcccg accgctgcgc cttatccggt aactatcgtc ttgagtccaa     6420
cccggtaaga cacgacttat cgccactggc agcagccact ggtaacagga ttagcagagc    6480
gaggtatgta ggcggtgcta cagagttctt gaagtggtgg cctaactacg gctacactag    6540
aaggacagta tttggtatct gcgctctgct gaagccagtt accttcggaa aaagagttgg    6600
tagctcttga tccggcaaac aaaccaccgc tggtagcggt ggtttttttg tttgcaagca    6660
gcagattacg cgcagaaaaa aaggatctca agaagatcct ttgatctttt ctacggggtc    6720
tgacgctcag tggaacgaaa actcacgtta agggattttg gtcatgaaca ataaaactgt    6780
ctgcttacat aaacagtaat acaaggggtg ttatgagcca tattcaacgg gaaacgtctt    6840
gctctaggcc gcgattaaat tccaacatgg atgctgattt atatgggtat aaatgggctc    6900
gcgataatgt cgggcaatca ggtgcgacaa tctatcgatt gtatgggaag cccgatgcgc    6960
cagagttgtt tctgaaacat ggcaaaggta gcgttgccaa tgatgttaca gatgagatgg    7020
tcagactaaa ctggctgacg gaatttatgc ctcttccgac catcaagcat tttatccgta    7080
ctcctgatga tgcatggtta ctcaccactg cgatccccgg gaaaacagca ttccaggtat    7140
tagaagaata tcctgattca ggtgaaaata ttgttgatgc gctggcagtg ttcctgcgcc    7200
ggttgcattc gattcctgtt tgtaattgtc cttttaacag cgatcgcgta tttcgtctcg    7260
ctcaggcgca atcacgaatg aataacggtt tggttgatgc gagtgatttt gatgacgagc    7320
gtaatggctg gcctgttgaa caagtctgga agaaatgca taaactttg ccattctcac      7380 cggattcagt cgtcactcat ggtgatttct cacttgataa ccttattttt gacgagggga    7440
aattaatagg ttgtattgat gttggacgag tcggaatcgc agaccgatac caggatcttg    7500
ccatcctatg gaactgcctc ggtgagtttt ctccttcatt acagaaacgg ctttttcaaa    7560
```

```
aatatggtat tgataatcct gatatgaata aattgcagtt tcatttgatg ctcgatgagt    7620
ttttctaaga attaattcat gagcggatac atatttgaat gtatttagaa aaataaacaa    7680
ataggggttc cgcgcacatt tccccgaaaa gtgccacctg aaattgtaaa cgttaatatt    7740
ttgttaaaat tcgcgttaaa ttttgttaa atcagctcat ttttaacca ataggccgaa    7800 atcggcaaaa tcccttataa atcaaaagaa tagaccgaga tagggttgag tgttgttcca    7860
gtttggaaca agagtccact attaaagaac gtggactcca acgtcaaagg gcgaaaaacc    7920
gtctatcagg gcgatggccc actacgtgaa ccatcaccct aatcaagttt ttgggggtcg    7980
aggtgccgta aagcactaaa tcggaaccct aaagggagcc cccgatttag agcttgacgg    8040
ggaaagccgg cgaacgtggc gagaaaggaa gggaagaaag cgaaaggagc gggcgctagg    8100
gcgctggcaa gtgtagcggt cacgctgcgc gtaaccacca cacccgccgc gcttaatgcg    8160
ccgctacagg gcgcgtccca ttcgcca    8187

<210> SEQ ID NO 20
<211> LENGTH: 7887
<212> TYPE: DNA
<213> ORGANISM: Artificial Sequence
<220> FEATURE:
<223> OTHER INFORMATION: vector

<400> SEQUENCE: 20
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagttagtgg tggtggtggt     180
ggtgatcctg cgcaacaacc tccgcttttg ccacctcaat gttgagcgta tcgcggatat     240
gttttttcac ccacttctgg cctggctcaa cctcattgcc tgtagacgat atgatagtag     300
acgcaagctt cgacttggcg tccgcaacag gcgcagcaag tgcgctggtc gcaatgcctg     360
ttggagccgg ctgctcgtgg tactcgataa tctgtacgct tgtaatatag ccgtcatcgt     420
ctggaagcgt aatttcaatc gtattgctcg tcagcagctt gctggtgtcc aactcaaatt     480
ccgcaaaggt cagcagattt ccaggcttat ccgtataggc cagatccttg ctgaagcttt     540
gcatgttggc cgtatcaccc gaatttacaa ccacttgcat atcctctgca aacccactgc     600
ccgtcttgcc gaagccaata cgaagagtcg ctttggcgag atcagcaggc cgcgcttgaa     660
ccgtaaatga ggcgggtgca tttacgctcg tcggcacaag ttcctgagga gcgtatgcaa     720
attctctctc ccatgtttg gtgaatggag gattggaatc aagtgtaatc tcgaatacgc     780
tcatctcctg cacacgcata tacacattgt tcagatctgc tacattcttt tgttcatagg     840
tcaggtcgcc cttctccagg aagaaatgct tccgagttac gcctgcaata ttagcgcctc     900
ccgtgaacac attcagatca aggttcaccc gctgcgagtt cagattgtgc acggctacat     960
acaccttgtc attgtagcgg accgcattcg tgaagacgcg ctcttgatcc gcttcagaag    1020
gcaggaatgc accgcgataa tccttccaca tgtccagata cgcttccatt ggcgtcattt    1080
cttccaataa tccattctgt gtttcattat atttgtagaa cgtacccgtg gagttggggc    1140
gccagttaat gatgggatac agataaggaa ccagcatgcc gattgtatcg gaataattaa    1200
tgaaacgcag catgtagccg ttgaaggcca ctagcttctg gaagtaatcc gcatcgcttc    1260
cagccgtatt gtaggtgcct tcttctgtaa tatagatcgg cttcacgtta tccgtattcg    1320
ccatgtgagc gttaagcagg tcaagcaccg cttccattcg cccgctcaag aagccatccg    1380
agttgttctc tctgtcatga atgaacaggt tggcatttc atagaagtga tgcgaatacc    1440
```

```
aatccaagga atctttcgtg tcatccataa atttcagctg ggcgcgcgct tcgtcgaaat    1500 cattttctc caaatacatg aatgcgcttg atggtccgcc cactaatacg tccggattct    1560
ccgccttcac ttccgcggct accttgttgt ggaactcgga caaatagctc cacgcttgct    1620
ctggctccga ctggaagaac caccactcct gcgggatggt cgattcgttc ttaacctcca    1680
cgtacttggg acccagtccg tcaaatctag tatcgatgct tttgatcagc ttggccgagg    1740
cgtccgccgc tgcatcgaag ttggcgcggg acggtgtgcc gaaatgctcc gattgtccgg    1800
aattagggga ttcccacatc cacctcggcc agccgtctag cgtcaggaca taatccttgc    1860
cgatggatgg atacagactt tcgaatttgt cgatggcagg ctgactcttc gcataaacct    1920
cattcgtcgc tgtaaagtca gcatatccag ggcgcgcagg atcttcctta agacccgccc    1980
agctcgtcag tagattataa tgaaacgcac ctcggccggg agtaaagccg taatcatgag    2040
tcgttctgtg gtacgcctcg tccaacaccg taaattcgcc gccggcttgc tctaagccga    2100
tcggaccact gttcacatgg taacgcttga acacttcctc gggcagctta tcgacaccgt    2160
ccatacttaa gtttgtaagc gcatccacat tgacggacac attcagaatg tccttgtctc    2220
caccaagaac ggtccatgcg gaggtgtcga actccagcgg cacgccttcc tcttcccagt    2280
ggtagacgct gcgaagcgtt ccgttgccga cgattttcat tttgtagcct tcataaataa    2340
tgtcgccgtt cgtacccttta atcagccaag gatgggtaat accctccgtc ggggttgtctt   2400 cctggaagcc catcttcgta tagttggtat ataatccggt gatgccgtcc ttccagccgc    2460
cattctggaa tactgtccaa tgtgtctcga ccccattcgg gtcaatgaca tatagctcca    2520
tcgtttgcgc gacggatccc tcgaagcgca catcaccgaa cagacgccac actcgcgcat    2580
ccatggcagg aatatcaaac gttacctcgc cattaatctg caaatattgc ccatccggga    2640
attgcaggaa gttaatgcgc tgaatccggc tttctccgtt aatactgttg aaataagcta    2700
ccgcattatc gccgaattgt cccttgtaat gctcggcaac ggcaggaatg gtatcgaaat    2760
ctgccttgtc ggttctaata ttctcaggaa gctcgtcgtt gacctctgcc atatgtatat    2820
ctccttctta aagttaaaca aaattatttc tagaggggaa ttgttatccg ctcacaattc    2880
ccctatagtg agtcgtatta atttcgcggg atcgagatcg atctcgatcc tctacgccgg    2940
acgcatcgtg gccggcatca ccggcgccac aggtgcggtt gctggcgcct atatcgccga    3000
catcaccgat ggggaagatc gggctcgcca cttcgggctc atgagcgctt gtttcggcgt    3060
gggtatggtg gcaggccccg tggccggggg actgttgggc gccatctcct tgcatgcacc    3120
attccttgcg gcggcggtgc tcaacggcct caacctacta ctgggctgct tcctaatgca    3180
ggagtcgcat aagggagagc gtcgagatcc cggacaccat cgaatggcgc aaaacctttc    3240
gcggtatggc atgatagcgc ccggaagaga gtcaattcag ggtggtgaat gtgaaaccag    3300
taacgttata cgatgtcgca gagtatgccg gtgtctctta tcagaccgtt tcccgcgtgg    3360
tgaaccaggc cagccacgtt tctgcgaaaa cgcgggaaaa agtggaagcg gcgatggcgg    3420
agctgaatta cattcccaac cgcgtggcac aacaactggc gggcaaacag tcgttgctga    3480
ttggcgttgc cacctccagt ctggccctgc acgcgccgtc gcaaattgtc gcggcgatta    3540
aatctcgcgc cgatcaactg ggtgccagcg tggtggtgtc gatggtagaa cgaagcggcg    3600
tcgaagcctg taaagcggcg gtgcacaatc ttctcgcgca acgcgtcagt gggctgatca    3660
ttaactatcc gctggatgac caggatgcca ttgctgtgga agctgcctgc actaatgttc    3720
cggcgttatt tcttgatgtc tctgaccaga cacccatcaa cagtattatt ttctcccatg    3780
```

```
aagacggtac gcgactgggc gtggagcatc tggtcgcatt gggtcaccag caaatcgcgc   3840
tgttagcggg cccattaagt tctgtctcgg cgcgtctgcg tctggctggc tggcataaat   3900
atctcactcg caatcaaatt cagccgatag cggaacggga aggcgactgg agtgccatgt   3960
ccggttttca acaaaccatg caaatgctga atgagggcat cgttcccact gcgatgctgg   4020
ttgccaacga tcagatggcg ctgggcgcaa tgcgcgccat taccgagtcc gggctgcgcg   4080
ttggtgcgga catctcggta gtgggatacg acgataccga agacagctca tgttatatcc   4140
cgccgttaac caccatcaaa caggattttc gcctgctggg gcaaaccagc gtggaccgct   4200
tgctgcaact ctctcagggc caggcggtga agggcaatca gctgttgccc gtctcactgg   4260
tgaaaagaaa aaccaccctg gcgcccaata cgcaaaccgc ctctcccgcg cgttggccg    4320 attcattaat gcagctggca cgacaggttt cccgactgga aagcgggcag tgagcgcaac   4380
gcaattaatg taagttagct cactcattag gcaccgggat ctcgaccgat gcccttgaga   4440
gccttcaacc cagtcagctc cttccggtgg gcgcggggca tgactatcgt cgccgcactt   4500
atgactgtct tctttatcat gcaactcgta ggacaggtgc cggcagcgct ctgggtcatt   4560
ttcggcgagg accgctttcg ctggagcgcg acgatgatcg gcctgtcgct tgcggtattc   4620
ggaatcttgc acgccctcgc tcaagccttc gtcactggtc cgccaccaa acgtttcggc    4680 gagaagcagg ccattatcgc cggcatggcg gccccacggg tgcgcatgat cgtgctcctg   4740
tcgttgagga cccggctagg ctggcggggt tgccttactg gttagcagaa tgaatcaccg   4800
atacgcgagc gaacgtgaag cgactgctgc tgcaaaacgt ctgcgacctg agcaacaaca   4860
tgaatggtct tcggtttccg tgtttcgtaa agtctggaaa cgcggaagtc agcgccctgc   4920
accattatgt tccggatctg catcgcagga tgctgctggc tacccgtgtg aacacctaca   4980
tctgtattaa cgaagcgctg gcattgaccc tgagtgattt ttctctggtc ccgccgcatc   5040
cataccgcca gttgtttacc ctcacaacgt tccagtaacc gggcatgttc atcatcagta   5100
acccgtatcg tgagcatcct ctctcgtttc atcggtatca ttaccccat gaacagaaat     5160 ccccttaca cggaggcatc agtgaccaaa caggaaaaaa ccgcccttaa catggcccgc     5220
tttatcagaa gccagacatt aacgcttctg gagaaactca acgagctgga cgcggatgaa   5280
caggcagaca tctgtgaatc gcttcacgac cacgctgatg agctttaccg cagctgcctc   5340
gcgcgtttcg gtgatgacgg tgaaaacctc tgacacatgc agctcccgga cgcgtcaca    5400 gcttgtctgt aagcggatgc cgggagcaga caagcccgtc agggcgcgtc agcgggtgtt   5460
ggcgggtgtc ggggcgcagc catgacccag tcacgtagcg atagcggagt gtatactggc   5520
ttaactatgc ggcatcagag cagattgtac tgagagtgca ccatatatgc ggtgtgaaat   5580
accgcacaga tgcgtaagga gaaaataccg catcaggcgc tcttccgctt cctcgctcac   5640
tgactcgctg cgctcggtcg ttcggctgcg gcgagcggta tcagctcact caaaggcggt   5700
aatacggtta tccacagaat caggggataa cgcaggaaag aacatgtgag caaaaggcca   5760
gcaaaaggcc aggaaccgta aaaaggccgc gttgctggcg ttttccata ggctccgccc      5820 ccctgacgag catcacaaaa atcgacgctc aagtcagagg tggcgaaacc cgacaggact   5880
ataaagatac caggcgtttc ccctggaag ctccctcgtg cgctctcctg ttccgaccct      5940
gccgcttacc ggatacctgt ccgcctttct cccttcggga agcgtggcgc tttctcatag   6000
ctcacgctgt aggtatctca gttcggtgta ggtcgttcgc tccaagctgg gctgtgtgca   6060 cgaaccccc gttcagcccg accgctgcgc cttatccggt aactatcgtc ttgagtccaa     6120
cccggtaaga cacgacttat cgccactggc agcagccact ggtaacagga ttagcagagc   6180
```

```
gaggtatgta ggcggtgcta cagagttctt gaagtggtgg cctaactacg gctacactag      6240
aaggacagta tttggtatct gcgctctgct gaagccagtt accttcggaa aaagagttgg      6300
tagctcttga tccggcaaac aaaccaccgc tggtagcggt ggttttttg  tttgcaagca      6360 gcagattacg cgcagaaaaa aaggatctca agaagatcct ttgatctttt ctacggggtc      6420
tgacgctcag tggaacgaaa actcacgtta agggattttg gtcatgaaca ataaaactgt      6480
ctgcttacat aaacagtaat acaaggggtg ttatgagcca tattcaacgg gaaacgtctt      6540
gctctaggcc gcgattaaat tccaacatgg atgctgattt atatgggtat aaatgggctc      6600
gcgataatgt cgggcaatca ggtgcgacaa tctatcgatt gtatgggaag cccgatgcgc      6660
cagagttgtt tctgaaacat ggcaaaggta gcgttgccaa tgatgttaca gatgagatgg      6720
tcagactaaa ctggctgacg gaatttatgc ctcttccgac catcaagcat tttatccgta      6780
ctcctgatga tgcatggtta ctcaccactg cgatccccgg aaaacagca  ttccaggtat      6840 tagaagaata tcctgattca ggtgaaaata ttgttgatgc gctggcagtg ttcctgcgcc      6900
ggttgcattc gattcctgtt tgtaattgtc cttttaacag cgatcgcgta tttcgtctcg      6960
ctcaggcgca atcacgaatg aataacggtt tggttgatgc gagtgatttt gatgacgagc      7020
gtaatggctg gcctgttgaa caagtctgga agaaatgca  taaactttg  ccattctcac      7080 cggattcagt cgtcactcat ggtgatttct cacttgataa ccttattttt gacgaggga      7140 aattaatagg ttgtattgat gttggacgag tcggaatcgc agaccgatac caggatcttg      7200
ccatcctatg gaactgcctc ggtgagtttt ctccttcatt acagaaacgg cttttcaaa      7260 aatatggtat tgataatcct gatatgaata aattgcagtt tcatttgatg ctcgatgagt      7320
ttttctaaga attaattcat gagcggatac atatttgaat gtatttagaa aaataaacaa      7380
ataggggttc gcgcacatt  tccccgaaaa gtgccacctg aaattgtaaa cgttaatatt      7440
ttgttaaaat tcgcgttaaa ttttttgttaa atcagctcat tttttaacca ataggccgaa      7500
atcggcaaaa tcccttataa atcaaaagaa tagaccgaga taggggttgag tgttgttcca      7560 gtttggaaca agagtccact attaaagaac gtggactcca acgtcaaagg gcgaaaaacc      7620
gtctatcagg gcgatggccc actacgtgaa ccatcaccct aatcaagttt tttggggtcg      7680
aggtgccgta aagcactaaa tcggaacccct aaagggagcc cccgatttag agcttgacgg      7740
ggaaagccgg cgaacgtggc gagaaaggaa gggaagaaag cgaaaggagc gggcgctagg      7800
gcgctggcaa gtgtagcggt cacgctgcgc gtaaccacca cacccgccgc gcttaatgcg      7860
ccgctacagg gcgcgtccca ttcgcca                                         7887
```

<210> SEQ ID NO 21
<211> LENGTH: 7587
<212> TYPE: DNA
<213> ORGANISM: Artificial Sequence
<220> FEATURE:
<223> OTHER INFORMATION: vector

<400> SEQUENCE: 21

```
atccggatat agttcctcct ttcagcaaaa aaccccctcaa gacccgttta gaggccccaa        60
ggggttatgc tagttattgc tcagcggtgg cagcagccaa ctcagcttcc tttcgggctt       120
tgttagcagc cggatctcag tggtggtggt ggtggtgctc gagttagtgg tggtggtggt       180
ggtgaaaggt cagcagattt ccaggcttat ccgtataggc cagatccttg ctgaagcttt       240
gcatgttggc cgtatcaccc gaatttacaa ccacttgcat atcctctgca aacccactgc       300
```

```
ccgtcttgcc gaagccaata cgaagagtcg ctttggcgag atcagcaggc cgcgcttgaa    360
ccgtaaatga ggcgggtgca tttacgctcg tcggcacaag ttcctgagga gcgtatgcaa    420
attctctctc ccatgttttg gtgaatggag gattggaatc aagtgtaatc tcgaatacgc    480
tcatctcctg cacacgcata tacacattgt tcagatctgc tacattcttt tgttcatagg    540
tcaggtcgcc cttctccagg aagaaatgct tccgagttac gcctgcaata ttagcgcctc    600
ccgtgaacac attcagatca aggttcaccc gctgcgagtt cagattgtgc acggctacat    660
acaccttgtc attgtagcgg accgcattcg tgaagacgcg ctcttgatcc gcttcagaag    720
gcaggaatgc accgcgataa tccttccaca tgtccagata cgcttccatt ggcgtcattt    780
cttccaataa tccattctgt gtttcattat atttgtagaa cgtacccgtg gagttggggc    840
gccagttaat gatgggatac agataaggaa ccagcatgcc gattgtatcg gaataattaa    900
tgaaacgcag catgtagccg ttgaaggcca ctagcttctg gaagtaatcc gcatcgcttc    960
cagccgtatt gtaggtgcct tcttctgtaa tatagatcgg cttcacgtta tccgtattcg   1020
ccatgtgagc gttaagcagg tcaagcaccg cttccattcg cccgctcaag aagccatccg   1080
agttgttctc tctgtcatga atgaacaggt tggcattttc atagaagtga tgcgaatacc   1140
aatccaagga atctttcgtg tcatccataa atttcagctg ggcgcgcgct tcgtcgaaat   1200 cattttctc caaatacatg aatgcgcttg atggtccgcc cactaatacg tccggattct   1260
ccgccttcac ttccgcggct accttgttgt ggaactcgga caaatagctc cacgcttgct   1320
ctggctccga ctggaagaac caccactcct gcgggatggt cgattcgttc ttaacctcca   1380
cgtacttggg acccagtccg tcaaatctag tatcgatgct tttgatcagc ttggccgagg   1440
cgtccgccgc tgcatcgaag ttggcgcggg acggtgtgcc gaaatgctcc gattgtccgg   1500
aattagggga ttcccacatc cacctcggcc agccgtctag cgtcaggaca taatccttgc   1560
cgatggatgg atacagactt tcgaatttgt cgatggcagg ctgactcttc gcataaacct   1620
cattcgtcgc tgtaaagtca gcatatccag ggcgcgcagg atcttcctta agacccgccc   1680
agctcgtcag tagattataa tgaaacgcac ctcggccggg agtaaagccg taatcatgag   1740
tcgttctgtg gtacgcctcg tccaacaccg taaattcgcc gccggcttgc tctaagccga   1800
tcggaccact gttcacatgg taacgcttga acacttcctc gggcagctta tcgacaccgt   1860
ccatacttaa gtttgtaagc gcatccacat tgacggacac attcagaatg tccttgtctc   1920
caccaagaac ggtccatgcg gaggtgtcga actccagcgg cacgccttcc tcttcccagt   1980
ggtagacgct gcgaagcgtt ccgttgccga cgattttcat tttgtagcct tcataaataa   2040
tgtcgccgtt cgtacccta atcagccaag gatgggtaat accctccgtc gggttgtctt   2100
cctggaagcc catcttcgta tagttggtat ataatccggt gatgccgtcc ttccagccgc   2160
cattctggaa tactgtccaa tgtgtctcga ccccattcgg gtcaatgaca tatagctcca   2220
tcgtttgcgc gacggatccc tcgaagcgca catcaccgaa cagacgccac actcgcgcat   2280
ccatggcagg aatatcaaac gttacctcgc cattaatctg caaatattgc ccatccggga   2340
attgcaggaa gttaatgcgc tgaatccggc tttctccgtt aatactgttg aaataagcta   2400
ccgcattatc gccgaattgt cccttgtaat gctcggcaac ggcaggaatg gtatcgaaat   2460
ctgccttgtc ggttctaata ttctcaggaa gctcgtcgtt gacctctgcc atatgtatat   2520
ctccttctta aagttaaaca aaattatttc tagaggggaa ttgttatccg ctcacaattc   2580
ccctatagtg agtcgtatta atttcgcggg atcgagatcg atctcgatcc tctacgccgg   2640
acgcatcgtg gccggcatca ccggcgccac aggtgcggtt gctggcgcct atatcgccga   2700
```

```
catcaccgat ggggaagatc gggctcgcca cttcgggctc atgagcgctt gtttcggcgt   2760
gggtatggtg gcaggccccg tggccggggg actgttgggc gccatctcct tgcatgcacc   2820
attccttgcg gcggcggtgc tcaacggcct caacctacta ctgggctgct tcctaatgca   2880
ggagtcgcat aagggagagc gtcgagatcc cggacaccat cgaatggcgc aaaacctttc   2940
gcggtatggc atgatagcgc ccggaagaga gtcaattcag ggtggtgaat gtgaaaccag   3000
taacgttata cgatgtcgca gagtatgccg gtgtctctta tcagaccgtt tcccgcgtgg   3060
tgaaccaggc cagccacgtt tctgcgaaaa cgcgggaaaa agtggaagcg gcgatggcgg   3120
agctgaatta cattcccaac cgcgtggcac aacaactggc gggcaaacag tcgttgctga   3180
ttggcgttgc cacctccagt ctggccctgc acgcgccgtc gcaaattgtc gcggcgatta   3240
aatctcgcgc cgatcaactg ggtgccagcg tggtggtgtc gatggtagaa cgaagcggcg   3300
tcgaagcctg taaagcggcg gtgcacaatc ttctcgcgca acgcgtcagt gggctgatca   3360
ttaactatcc gctggatgac caggatgcca ttgctgtgga agctgcctgc actaatgttc   3420
cggcgttatt tcttgatgtc tctgaccaga cacccatcaa cagtattatt ttctcccatg   3480
aagacggtac gcgactgggc gtggagcatc tggtcgcatt gggtcaccag caaatcgcgc   3540
tgttagcggg cccattaagt tctgtctcgg cgcgtctgcg tctggctggc tggcataaat   3600
atctcactcg caatcaaatt cagccgatag cggaacggga aggcgactgg agtgccatgt   3660
ccggttttca acaaaccatg caaatgctga atgagggcat cgttcccact gcgatgctgg   3720
ttgccaacga tcagatggcg ctgggcgcaa tgcgcgccat taccgagtcc gggctgcgcg   3780
ttggtgcgga catctcggta gtgggatacg acgataccga agacagctca tgttatatcc   3840
cgccgttaac caccatcaaa caggattttc gcctgctggg gcaaaccagc gtggaccgct   3900
tgctgcaact ctctcagggc caggcggtga agggcaatca gctgttgccc gtctcactgg   3960
tgaaaagaaa aaccaccctg gcgcccaata cgcaaaccgc ctctccccgc gcgttggccg   4020
attcattaat gcagctggca cgacaggttt cccgactgga aagcgggcag tgagcgcaac   4080
gcaattaatg taagttagct cactcattag gcaccgggat ctcgaccgat gcccttgaga   4140
gccttcaacc cagtcagctc cttccggtgg gcgcggggca tgactatcgt cgccgcactt   4200
atgactgtct tctttatcat gcaactcgta ggacaggtgc cggcagcgct ctgggtcatt   4260
ttcggcgagg accgctttcg ctggagcgcg acgatgatcg gcctgtcgct tgcggtattc   4320
ggaatcttgc acgccctcgc tcaagccttc gtcactggtc cgccaccaa acgtttcggc   4380
gagaagcagg ccattatcgc cggcatggcg gccccacggg tgcgcatgat cgtgctcctg   4440
tcgttgagga cccggctagg ctggcggggt tgccttactg gttagcagaa tgaatcaccg   4500
atacgcgagc gaacgtgaag cgactgctgc tgcaaaacgt ctgcgacctg agcaacaaca   4560
tgaatggtct tcggtttccg tgtttcgtaa agtctggaaa cgcggaagtc agcgccctgc   4620
accattatgt tccggatctg catcgcagga tgctgctggc tacccgtgtg aacacctaca   4680
tctgtattaa cgaagcgctg gcattgaccc tgagtgattt ttctctggtc cgccgcatc   4740
cataccgcca gttgtttacc ctcacaacgt tccagtaacc gggcatgttc atcatcagta   4800
acccgtatcg tgagcatcct ctctcgtttc atcggtatca ttacccccat gaacagaaat   4860
cccccttaca cggaggcatc agtgaccaaa caggaaaaaa ccgcccttaa catggcccgc   4920
tttatcagaa gccagacatt aacgcttctg gagaaactca acgagctgga cgcggatgaa   4980
caggcagaca tctgtgaatc gcttcacgac cacgctgatg agctttaccg cagctgcctc   5040
```

```
gcgcgtttcg gtgatgacgg tgaaaacctc tgacacatgc agctcccgga gacggtcaca    5100
gcttgtctgt aagcggatgc cgggagcaga caagcccgtc agggcgcgtc agcgggtgtt    5160
ggcgggtgtc ggggcgcagc catgacccag tcacgtagcg atagcggagt gtatactggc    5220
ttaactatgc ggcatcagag cagattgtac tgagagtgca ccatatatgc ggtgtgaaat    5280
accgcacaga tgcgtaagga gaaaataccg catcaggcgc tcttccgctt cctcgctcac    5340
tgactcgctg cgctcggtcg ttcggctgcg gcgagcggta tcagctcact caaaggcggt    5400
aatacggtta tccacagaat caggggataa cgcaggaaag aacatgtgag caaaaggcca    5460
gcaaaaggcc aggaaccgta aaaaggccgc gttgctggcg ttttttccata ggctccgccc    5520 ccctgacgag catcacaaaa atcgacgctc aagtcagagg tggcgaaacc cgacaggact    5580
ataaagatac caggcgtttc ccctggaag ctccctcgtg cgctctcctg ttccgaccct    5640
gccgcttacc ggatacctgt ccgcctttct cccttcggga agcgtggcgc tttctcatag    5700
ctcacgctgt aggtatctca gttcggtgta ggtcgttcgc tccaagctgg gctgtgtgca    5760 cgaaccccc gttcagcccg accgctgcgc cttatccggt aactatcgtc ttgagtccaa    5820
cccggtaaga cacgacttat cgccactggc agcagccact ggtaacagga ttagcagagc    5880
gaggtatgta ggcggtgcta cagagttctt gaagtggtgg cctaactacg ctacactag    5940 aaggacagta tttggtatct gcgctctgct gaagccagtt accttcggaa aaagagttgg    6000
tagctcttga tccggcaaac aaaccaccgc tggtagcggt ggtttttttg tttgcaagca    6060
gcagattacg cgcagaaaaa aaggatctca agaagatcct ttgatctttt ctacggggtc    6120
tgacgctcag tggaacgaaa actcacgtta agggattttg gtcatgaaca ataaaactgt    6180
ctgcttacat aaacagtaat acaaggggtg ttatgagcca tattcaacgg gaaacgtctt    6240
gctctaggcc gcgattaaat tccaacatgg atgctgattt atatgggtat aaatgggctc    6300
gcgataatgt cgggcaatca ggtgcgacaa tctatcgatt gtatgggaag cccgatgcgc    6360
cagagttgtt tctgaaacat ggcaaaggta gcgttgccaa tgatgttaca gatgagatgg    6420
tcagactaaa ctggctgacg gaatttatgc ctcttccgac catcaagcat tttatccgta    6480
ctcctgatga tgcatggtta ctcaccactg cgatccccgg aaaacagca ttccaggtat    6540 tagaagaata tcctgattca ggtgaaaata ttgttgatgc gctggcagtg ttcctgcgcc    6600
ggttgcattc gattcctgtt tgtaattgtc cttttaacag cgatcgcgta tttcgtctcg    6660
ctcaggcgca atcacgaatg aataacggtt tggttgatgc gagtgatttt gatgacgagc    6720
gtaatggctg gcctgttgaa caagtctgga aagaaatgca taaacttttg ccattctcac    6780
cggattcagt cgtcactcat ggtgatttct cacttgataa ccttattttt gacgagggga    6840
aattaatagg ttgtattgat gttggacgag tcggaatcgc agaccgatac caggatcttg    6900
ccatcctatg gaactgcctc ggtgagtttt ctccttcatt acagaaacgg cttttttcaaa    6960 aatatggtat tgataatcct gatatgaata aattgcagtt tcatttgatg ctcgatgagt    7020
ttttctaaga attaattcat gagcggatac atatttgaat gtatttagaa aaataaacaa    7080
ataggggttc gcgcacatt tccccgaaaa gtgccacctg aaattgtaaa cgttaatatt    7140
ttgttaaaat tcgcgttaaa ttttgttaa atcagctcat tttttaacca ataggccgaa    7200
atcggcaaaa tccttataa atcaaaagaa tagaccgaga tagggttgag tgttgttcca    7260
gtttggaaca agagtccact attaaagaac gtggactcca acgtcaaagg gcgaaaaacc    7320
gtctatcagg gcgatggccc actacgtgaa ccatcaccct aatcaagttt ttggggtcg    7380 aggtgccgta aagcactaaa tcggaaccct aaagggagcc cccgatttag agcttgacgg    7440
```

```
ggaaagccgg cgaacgtggc gagaaaggaa gggaagaaag cgaaaggagc gggcgctagg      7500
gcgctggcaa gtgtagcggt cacgctgcgc gtaaccacca cacccgccgc gcttaatgcg      7560
ccgctacagg gcgcgtccca ttcgcca                                          7587
```

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22

```
gatatacata tggcagaggt caacgacgag cttc                                   34
```

<210> SEQ ID NO 23
<211> LENGTH: 44
<212> TYPE: DNA
<213> ORGANISM: Artificial Sequence
<220> FEATURE:
<223> OTHER INFORMATION: primer

<400> SEQUENCE: 23

```
caatatctcg agctagatca gatcagactt ctctagcaat cttc                        44
```

<210> SEQ ID NO 24
<211> LENGTH: 55
<212> TYPE: DNA
<213> ORGANISM: Artificial Sequence
<220> FEATURE:
<223> OTHER INFORMATION: primer

<400> SEQUENCE: 24

```
caatatctcg agttagtggt ggtggtggtg gtgaaaggtc agcagatttc caggc             55
```

<210> SEQ ID NO 25
<211> LENGTH: 52
<212> TYPE: DNA
<213> ORGANISM: Artificial Sequence
<220> FEATURE:
<223> OTHER INFORMATION: primer

<400> SEQUENCE: 25

```
caatatctcg agttagtggt ggtggtggtg gtgatcctgc gcaacaacct cc                52
```

<210> SEQ ID NO 26
<211> LENGTH: 53
<212> TYPE: DNA
<213> ORGANISM: Artificial Sequence
<220> FEATURE:
<223> OTHER INFORMATION: primer

<400> SEQUENCE: 26

```
caatatctcg agttagtggt ggtggtggtg gtgcggggca gtaaaatcaa ggc               53
```

<210> SEQ ID NO 27
<211> LENGTH: 53
<212> TYPE: DNA
<213> ORGANISM: Artificial Sequence
<220> FEATURE:
<223> OTHER INFORMATION: primer

<400> SEQUENCE: 27

```
caatatctcg agttagtggt ggtggtggtg gtggttcgga ttgccaggtc ctg               53
```

```
<210> SEQ ID NO 28
<211> LENGTH: 53
<212> TYPE: DNA
<213> ORGANISM: Artificial Sequence
<220> FEATURE:
<223> OTHER INFORMATION: primer

<400> SEQUENCE: 28
caatatctcg agttagtggt ggtggtggtg gtgagtaggc tggatcggct cgt            53

<210> SEQ ID NO 29
<211> LENGTH: 53
<212> TYPE: DNA
<213> ORGANISM: Artificial Sequence
<220> FEATURE:
<223> OTHER INFORMATION: primer

<400> SEQUENCE: 29
caatatctcg agttagtggt ggtggtggtg gtggccacca ggtggattgg aag            53

<210> SEQ ID NO 30
<211> LENGTH: 60
<212> TYPE: DNA
<213> ORGANISM: Artificial Sequence
<220> FEATURE:
<223> OTHER INFORMATION: primer

<400> SEQUENCE: 30
caatatctcg agttagtggt ggtggtggtg gtggatcaga tcagacttct ctagcaatct     60
```

AGARASE, COMPOSITION CONTAINING THE SAME, AND APPLICATION THEREOF

BACKGROUND

Technical Field

The present invention is related to an agarase, especially to an agarase produced by a prokaryotic cell expression system.

Description of Related Art

Agar is a hydrophilic polysaccharide extracted from cell walls of red algae such as *Gelidium* spp., *Gracilaria* spp., *Porphyra* spp., and etc, and the main components thereof are agarose and agaropectin. Agarose is a neutral polysaccharide with α-1,3 and β-1,4 glycosidic linkage, which is capable of forming gel and has a molecular weight of at least 100 kDa. Agaropectin is not capable of forming gel and has a molecular weight of at most 20 kDa. Agaropectin has a similar composition with agarose while some hydroxyl groups of 3,6-anhydro-α-L-galactose thereof are replaced with methoxy, sulfoxy or pyruvate groups.

Hydrolase capable of hydrolyzing agar is named agarase, which can be classified as α-agarase (EC 3.2.1.158) and β-agarase (EC 3.2.1.81) in accordance with the hydrolysis site thereof. α-Agarase hydrolyzes at the α-1,3 glycosidic linkage of agarose and agaropectin and results in agaro-oligosaccharides having 3,6-anhydro-α-L-galactose group at the reducing end thereof. β-Agarase hydrolyzes at the β-1,4 glycosidic linkage of agarose and agaropectin and results in neoagaro-oligosaccharides having D-galactose group at the reducing end thereof.

There are many applications for agarase. Case in point, agarase can be used in molecular biology research for recovery of DNA from agarose gel; can be used in cartilage tissue engineering as agar substrate for supporting cartilage cells and thereby facilitating cartilage cells purification, increasing collagen content, and improving the culture of cartilage tissue; can be used for preparing agaro-oligosaccharide and neoagaro-oligosaccharide; can be used for preparing algae protoplast for DNA transformation and cell fusion; can be used for hydrolysis of algae polysaccharides and speculating the structure of the algae polysaccharides based on the hydrolysis product; can be used for preparing algae single cell being used as feed of marine animal breeding.

Furthermore, the current researches have proved the oligosaccharides obtained by hydrolyzing agar or algae polysaccharide crude extract exhibit several physiological and biological activities, such as antioxidation, immune regulation, antibacterial, tyrosinase suppression, moisturizing, being used as prebiotic, decreasing serum total cholesterol, and etc. The oligosaccharides can also be the new generation of high value functional oligosaccharides, which are widely applied in cosmetic, health food, and pharmaceutical industries. There are several microorganisms being proved to be able to produce agarases; nevertheless, the production of agarases by those known microorganisms encounters lots of difficulties and defects unfavorable for mass production in the industries, for instance, insufficient production, unstable production, safety concern to the bacterial used, high production cost and etc.

In light of the foregoing, the researchers in the field have considered using acid hydrolysis method to hydrolyze agar or algae polysaccharide crude extract to obtain the required oligosaccharide. However, although conventional acid hydrolysis method is able to obtain agaro-oligosaccharide mixtures, it is unable to obtain products having uniform degree of polymerization. In comparison with acid hydrolysis method, enzymatic hydrolysis has several strengths and thereby is more ideal than acid hydrolysis method. The strengths include enzymatic selectivity in cutting specific types of glycosidic linkages to obtain oligosaccharides of desired polymerization, ease in controlling degradation condition, temperature required for enzymatic reaction is lower than that of acid hydrolysis method therefore the energy consumption is decreased, ease in operation comparing with acid hydrolysis method wherein processes like acid-base neutralization and desalination are not required, chemical agents are not necessary therefore the operation is safer and less possible in contaminating environment, and agaro-oligosaccharide and neoagaro-oligosaccharide can be obtained.

To sum up, in order to facilitate the industrial applications of the oligosaccharides obtained from agarase hydrolysis of agar or algae polysaccharide crude extract, there is a need of novel agarase to provide more options for the field. Moreover, there is also a need of a production method of agarase, which can be operated in lower cost so that the production cost of the aforesaid oligosaccharides can be decreased for facilitating commercialization.

SUMMARY

In light of the foregoing, one of the objectives of the present invention is to provide a novel agarase, which can provide more options for the industry.

Another objective of the present invention is to provide a method for neoagarooligosaccharide production by using agarase, which adapts prokaryotic cell expression system for mass production of recombinant agarase and applies the recombinant agarase in hydrolysis of agar, agarose, or crude extract of algal polysaccharide. The method is able to reduce the production cost of neoagarooligosaccharide.

In order to achieve to aforesaid objectives, the present invention provides a β-agarase, comprising at least an amino acid sequence as shown in SEQ ID NO: 06.

Preferably, said β-agarase has an amino acid sequence as shown in SEQ ID NO: 01. Preferably, said β-agarase has an amino acid sequence as shown SEQ ID NO: 02. Preferably, said β-agarase has an amino acid sequence as shown SEQ ID NO: 03. Preferably, said β-agarase has an amino acid sequence as shown SEQ ID NO: 04. Preferably, said 3-agarase has an amino acid sequence as shown SEQ ID NO: 05. Preferably, said β-agarase has an amino acid sequence as shown SEQ ID NO: 06.

The present invention also provides a composition for digesting agarose, comprising: 0.1 to 10 U/mL of the above mentioned agarase; and 50 to 200 mM of a buffer; wherein said U/mL and said mM are based on a total volume of said composition.

Preferably, said composition further comprises 1 to 2 mM of a salt based on a total volume of said composition.

Preferably, said salt is KCl, $ZnSO_4$, $FeSO_4$, $BaCl_2$, NaCl, $SrCl_2$, $CoCl_2$, $MgSO_4$, $MnCl_2$, $CaCl_2$, $AlCl_3$, or a combination thereof.

The present invention also provides a composition for digesting polysaccharide with α-1,3 and β-1,4 glycosidic linkage, comprising: 0.1 to 10 U/mL of the agarase of any of claims 1-7; and 1 to 2 mM of a salt; wherein said U/mL and said mM are based on a total volume of said composition.

Preferably, said composition further comprises 50 to 200 mM of a buffer based on a total volume of said composition.

Preferably, said salt is KCl, ZnSO$_4$, FeSO$_4$, BaCl$_2$, NaCl, SrCl$_2$, CoCl$_2$, MgSO$_4$, MnCl$_2$, CaCl$_2$, AlCl$_3$, or a combination thereof.

More preferably, said salt is FeSO$_4$, CoCl$_2$, MnCl$_2$, CaCl$_2$, AlCl$_3$, or a combination thereof.

Preferably, said polysaccharide with α-1,3 and β-1,4 glycosidic linkage is agarose, low melting point agarose, agar, seaweed polysaccharide crude extract, or a combination thereof.

Preferably, said composition comprises 2 to 10 U/mL of said agarase.

The present invention then provides a composition for producing neoagarooligosaccharide, comprising: 0.1 to 10 U/mL of the agarase of any of claims 1-7; and 1 to 2 mM of a salt; wherein said U/mL and said mM are based on a total volume of said composition.

Preferably, said composition further comprises 50 to 200 mM of a buffer based on a total volume of said composition.

Preferably, said salt is KCl, ZnSO$_4$, FeSO$_4$, BaCl$_2$, NaCl, SrCl$_2$, CoCl$_2$, MgSO$_4$, MnCl$_2$, CaCl$_2$, AlCl$_3$, or a combination thereof.

More preferably, said salt is FeSO$_4$, CoCl$_2$, MnCl$_2$, CaCl$_2$, AlCl$_3$, or a combination thereof.

Preferably, said composition comprises 2 to 10 U/mL of said agarase.

The present invention more provides a method for producing neoagarooligosaccharide, comprising the following steps: (A) providing a sample comprising an agarose; and (B) contacting said sample with the aforesaid composition.

Preferably, said composition further comprises 1 to 2 mM of a salt based of a total volume of said composition.

Preferably, a product of said method comprises at least 40 weight percentage of neoagarotetraose based on a total weight of said product.

Preferably, a product of said method substantially does not comprise neoagarobiose.

Preferably, said step (B) is conducted at 40° C. to 60° C.

Preferably, said step (B) is conducted at pH 5 to pH 7.

Preferably, said sample is agarose, low melting point agarose, agar, seaweed polysaccharide crude extract, or a combination thereof.

The present invention further provides an expression vector of β-agarase, comprising: a nucleotide sequence comprising a sequence selected from a group consisting of SEQ ID NO: 8, SEQ ID NO: 9, SEQ ID NO: 10, SEQ ID NO: 11, SEQ ID NO: 12, and SEQ ID NO: 13.

Preferably said expression vector has a sequence selected from a group consisting of SEQ ID NO: 15, SEQ ID NO: 16, SEQ ID NO: 17, SEQ ID NO: 18, SEQ ID NO: 19, and SEQ ID NO: 20.

To sum up, the present invention provides a novel agarase and shows a method for digesting agarose by using said agarase. It is notable that the researches of the present invention proved that the C' terminal deletion mutation of said agarase not only was able to remain the activity thereof but also was able to significantly increase the production thereof in an *E. coli* expression system. Accordingly, the preferable embodiment of the present agarases are particularly suitable for heterologous production by prokaryotic cell expression system and thus particularly favorable for commercialization.

DETAILED DESCRIPTION

Figure 1:
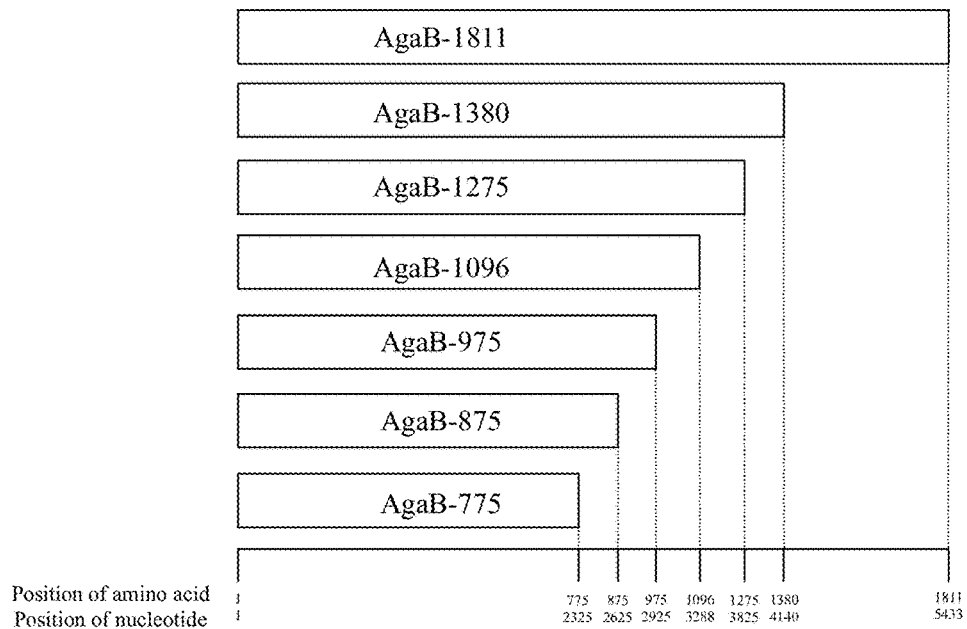
FIG. 1 is a schematic figure showing the relative site of the agarase genes of the present vectors pET-AgaB-2-775, pET-AgaB-2-875, pET-AgaB-2-975, pET-AgaB-2-1096, pET-AgaB-2-1275, pET-AgaB-2-1380 and pET-AgaB-2-1811 in comparison with a naturally occurring agarase.

As set forth above, although heterologous production of agarase by microorganism is known in the field, the conventional production is still facing lots of difficulties. Besides, although the field has known prokaryotic expression system as a tool for expressing desired protein, it is also recognized that not all kinds of protein can be expressed by using prokaryotic expression system, especially from the perspective of mass production. Factors affecting the expression of desired proteins including the codon usage of gene, the stability of the mRNA, the stability of the desired protein itself, the expression system chosen, the production conditions of the expression system, and etc. If the gene encoding the desired protein is not suitable for heterologous expression, it is nearly impossible to succeed in mass production of the desired protein by prokaryotic cell expression system. Through genetic engineering to the desired gene or fermenting engineering for improving culture technology, the production of the desired gene could be favorably increased and thus creating more strengths for the commercialization of the desired protein.

*Paenibacillus agarexedens* is a kind of bacterial isolated from meadow soil by scientist Miehlmann in 1972. Before the disclosure of the present invention, there has never had any reports regarding the gene encoding agarase of the bacterium. The present invention, however, isolated a specific nucleotide segment from the bacterium and obtained a novel agarase therefrom, which could contribute the field a new option of agarase.

An aspect of the present invention provides a β-agarase derived from *Paenibacillus agarexedens*, which comprises a sequence as shown in SEQ ID NO: 01. Said SEQ ID NO: 01 shows the amino acid sequence of the present invention containing 1811 amino acids. It is notable that said SEQ ID NO: 01 is corresponding to a nucleotide segment of the genome of *Paenibacillus agarexedens* but not a gene sequence. Without being bound by theory, the inventors of the present invention assumed SEQ ID NO: 01 is not an intact open reading frame of *Paenibacillus agarexeden*. In addition, SEQ ID NO: 01 had unknown physiological function at the time of the present invention. According to the relationship between amino acid and codon, those having ordinary skill in the art can infer the corresponding nucleotide sequence encoding said SEQ ID NO: 01. In a preferable embodiment, said β-agarase is encoded from a sequence as shown in SEQ ID NO: 08.

In the aforesaid aspect of the present invention, without destroying the normal activity of said agarase, the present invention adopted genetic engineering tools to delete amino acids of SEQ ID NO: 01 from the C' terminal thereof in order to improve the heterologous production of said agarase in a prokaryotic cell expression system.

In an alternative embodiment, the recombinant β-agarase produced by the genetic engineering research of the present invention comprises at least an amino acid sequence as shown in SEQ ID NO: 06. In another alternative embodiment, the recombinant β-agarase produced by the genetic engineering research of the present invention comprises at least No. 1 to the No. 875 amino acid of said SEQ ID NO: 01 in order. Said "comprises . . . in order" means said β-agarase comprises not only those amino acids but comprises them in an order as they are in accordance with SEQ ID NO: 01; provided that said β-agarase does not comprise the total length of SEQ ID NO: 01. Said "total length" is referred to as all amino acids and order thereof contained in SEQ ID NO: 01. Said "the first to the No. 875 amino acid" is referred to the first amino acid to the $875^{th}$ amino acid counted from N terminal.

In the aforesaid aspect of the present invention, a specific embodiment 01 provides a β-agarase, which comprises a sequence as shown in SEQ ID NO: 01 in order. Said sequence as shown in SEQ ID NO: 01 can be translated from SEQ ID NO: 08.

In the aforesaid aspect of the present invention, a specific embodiment 02 provides a β-agarase, which comprises No. 1 to No. 1380 amino acids of a sequence as shown in SEQ ID NO: 01 in order; that is, SEQ ID NO: 02. Said sequence as shown in SEQ ID NO: 02 can be translated from SEQ ID NO: 09.

In the aforesaid aspect of the present invention, a specific embodiment 03 provides a β-agarase, which comprises No. 1 to No. 1275 amino acids of a sequence as shown in SEQ ID NO: 01 in order; that is, SEQ ID NO: 03. Said sequence as shown in SEQ ID NO: 03 can be translated from SEQ ID NO: 10.

In the aforesaid aspect of the present invention, a specific embodiment 04 provides a β-agarase, which comprises No. 1 to No. 1096 amino acids of a sequence as shown in SEQ ID NO: 01 in order; that is, SEQ ID NO: 04. Said sequence as shown in SEQ ID NO: 04 can be translated from SEQ ID NO: 11.

In the aforesaid aspect of the present invention, a specific embodiment 05 provides a β-agarase, which comprises No. 1 to No. 975 amino acids of a sequence as shown in SEQ ID NO: 01 in order; that is, SEQ ID NO: 05. Said sequence as shown in SEQ ID NO: 05 can be translated from SEQ ID NO: 12.

In the aforesaid aspect of the present invention, a specific embodiment 06 provides a β-agarase, which comprises No. 1 to No. 875 amino acids of a sequence as shown in SEQ ID NO: 01 in order; that is, SEQ ID NO: 06. Said sequence as shown in SEQ ID NO: 05 can be translated from SEQ ID NO: 13.

Another aspect of the present invention provides a composition for digesting agarose. Said composition can be used in the industry for obtaining the hydrolysis product of agarose, such as neoagarotetraose. In an alternative embodiment, said composition comprises an agarase, which comprises at least No. 1 to the No. 875 amino acid of said SEQ ID NO: 01 in order. In a preferable embodiment, said composition comprises said agarase at a concentration of 0.1 to 10 U/mL; wherein said U/mL is based on a total volume of said composition.

In another embodiment, said composition comprises an agarase, which has an amino acid sequence selected from a group consisting of SEQ ID NO: 01, SEQ ID NO: 02, SEQ ID NO: 03, SEQ ID NO: 04, SEQ ID NO: 05 and SEQ ID NO: 06.

In a preferable embodiment, said composition further comprises 1 to 2 mM of a salt, 50 to 200 mM of a buffer or a combination thereof; wherein said mM is based on a total volume of said composition. According to the researches of the present invention, said salt is favorable for stabilizing and improving the activity of said agarase. Alternatively, said salt includes but is not limited to KCl, $ZnSO_4$, $FeSO_4$, $BaCl_2$, NaCl, $SrCl_2$, $CoCl_2$, $MgSO_4$, $MnCl_2$, $CaCl_2$, $AlCl_3$, or a combination thereof. Those having ordinary skill in the art can easily understand said salt could exist in a dissociation state thereof in which said salt derives into metal ion and non-metal ion, or exist in both a dissociation state and a non-dissociation state. Said buffer is also favorable for stabilizing the activity of said agarase. Alternatively, said buffer includes but is not limited to: citric acid buffer solution or phosphate buffer solution. Preferably, said citric acid buffer solution has a pH value of 5 to 6. Preferable, said phosphate buffer solution has a pH value of 6 to 7.

Another aspect of the present invention provides a method for producing neoagarooligosaccharide. The present method comprises the following steps: (A) providing a sample comprising agarose; and (B) contacting said sample with a composition. Said sample could be agarose, low melting point agarose, agar, seaweed polysaccharide crude extract, or a combination thereof. Said "contact or contacting" can be achieved by mixing said sample and said composition in an environment.

In an alternative embodiment, said product obtained in said method comprises at least 40 weight percentage of neoagarotetraose; wherein said weight percentage is based on a total weight of said product. In a preferable embodiment, said product substantially does not comprise neoagarobiose.

In a preferable embodiment, said contacting of said step (B) can be achieved by mixing said sample and said composition in an environment. Preferably, said contacting is performed at 40° C. to 60° C. Preferably, said contacting is performed at pH 5 to 7. In a preferable embodiment, said contacting is performed for 1 to 24 hours.

In another aspect of the present invention, the present invention provides an expression vector of β-agarase. Said expression vector comprises a nucleotide sequence comprising a sequence selected from a group consisting of SEQ ID NO: 8, SEQ ID NO: 9, SEQ ID NO: 10, SEQ ID NO: 11, SEQ ID NO: 12, and SEQ ID NO: 13. Said expression vector is used for heterologous expression of the β-agarase of the present invention in a prokaryotic cell expression system. Therefore, preferably, said expression vector further comprises a regulation element; wherein said regulation element can be recognized by the prokaryotic cell expression system used. In an alternatively embodiment, said regulation element at least comprises a promoter and a ribosome binding site; preferably, said regulation element can further comprises an operator, enhancer sequences, or a combination thereof.

In a preferably embodiment, said expression vector has a sequence selected from a group consisting of SEQ ID NO: 15, SEQ ID NO: 16, SEQ ID NO: 17, SEQ ID NO: 18, SEQ ID NO: 19, and SEQ ID NO: 20.

The term of "heterologous expression" or alike is referred to as the expression of said β-agarase in a microorganism that is not the naturally occurring source thereof. Case in point, the naturally occurring source of said β-agarase is P. agarexedens; thus, expression of said β-agarase in the E. coli expression system is "heterologous expression" as defined in the present invention. As set forth above, the production conditions of an expression system would affect the production amount of the desired protein and thus affect the production cost. In the key values of the production conditions can be obtained, the desired protein can be effectively and massively expressed in the expression system used. In a preferable embodiment of the present invention, the present invention obtained, after a great amount of trials, the preferable temperature for heterologous expression of the present β-agarase in the E. coli expression system is between 15 to 37° C. β-agarase expressed in that temperature range has better solubility so that the condition is favorable for mass production for commercial needs.

Experiment 1: Cloning of the Gene Encoding the Present Agarase and Establishing the Expression Vector of the Present Invention.

In this experiment, a particular sequence was chosen from the whole genome of P. agarexedens (which has an amino acid sequence as shown in SEQ ID NO: 01 with 1811 amino acids and has a nucleotide sequence as shown in SEQ ID NO: 08 with 5433 nucleotides excluding the start codon thereof) and was predicted to be able to encode a protein with digesting agarose ability (i.e. an agarase) by protein alignment analysis. Before the disclosure of the present invention, there had never been any research disclosed the aforesaid sequence or the translation product of the sequence might have the physiological ability as agarase. Moreover, said sequence has no significant similarity with the gene sequences of the known agarases in the field at the time of filing of the present invention. The present invention more established, by using genetic engineering technology, an expression vector for expressing said sequence in order to massively and stably express the desired agarase in a prokaryotic cell expression system.

Bacteria and Culture Medium

P. agarexedens BCRC 17346 was purchased from Food Industry Research and Development Institute as the research subject of agarase gene. Escherichia coli ECOS 9-5 (Yeastern, Taiwan) was chosen as host cell for DNA cloning. Nutrient broth (BD Difco, USA) containing 0.1% urea was used for culture of P. agarexedens. Also, 1.5% (w/v) agar was added if needed for preparing solid medium. Luria-Bertani (LB) medium (BD Difco, USA) was used for culture of E. coli, which can optionally incorporate antibiotic and 1.5% of agar.

Extraction of Genomic DNA

A colony of BCRC 17346 was picked and inoculated in nutrient broth containing 0.1% of urea. The broth was cultured at 30° C. and 180 rpm vibration for 24 hours. Then DNA purification kit was used for extracting genomic DNA of the bacterium. First of all, 4 ml of the broth was introduced to a tube and put into centrifugation for 5 minutes (5,870×g). The supernatant was discarded and the pellet was collected. Afterward, the pellet was re-suspended by 200 μL of solution A [10 mM Tris-HCl, pH 8.0; 10 mM EDTA; 50 mM; NaCl; 20% (w/v) sucrose; 10 mg/mL lysozyme] and placed at 37° C. for 1 hour. The purpose of this step was to lyse the cell wall of the bacteria. Then, 20 μL of proteinase K (10 mg/mL) and 200 μL of extraction reagent were added and the mixture was placed at 56° C. for reaction for 3 hours. During this time period, the mixture was slightly shaken upside-down every 5 minutes. Afterward, 200 μL of binding solution was added and the mixture was placed at 70° C. for 10 minutes. Then, 200 μL of anhydrous alcohol was added to the tube and mixed well. After that, all the liquid therein was transferred to a spin column. The spin column was positioned in a collection tube and the tube were put into centrifugation (17,970×g) for 2 minutes. The elution was discarded. Then, 300 μL of binding solution was added to the spin column and the tube was put into the centrifuge (17,970×g) for another 2 minutes. Again, the elution was discarded. 700 μL of wash solution was then added to the spin column. After centrifugation for 2 minutes, the elution was discarded. The step of wash solution was repeated one time. Lastly, centrifugation (17,970×g) was conducted for 5 minutes to remove any residue of alcohol. Afterward, the spin column was positioned in a sterile tube and a proper amount of sterile water was introduced to elude the genomic DNA.

Cloning of the Present Agarase DNA Fragment

The genomic DNA of P. agarexdens was used as template for performing polymerase chain reaction (PCR) to amplifying the present agarase DNA fragment. The following primer set was used in the PCR.

```
Primer name: PBAGA2DSNDEIF
                                            SEQ ID NO: 22
GATATACATATGGCAGAGGTCAACGACGAGCTTC Primer name: PBAGA2R
                                            SEQ ID NO: 23
CAATATCTCGAGCTAGATCAGATCAGACTTCTCTAGCAATCTTC
```

The PCR mixture (50 μL) contains 1×HiFi buffer, 200 μM of dNTP (dATP, dTTP, dGTP and dCTP), 1 μM of amplification primer, 100 ng of P. agarexdens genomic DNA and 1 U of VELOCITY™ DNA polymerase (BIOLINE, USA). The PCR condition was set as 98° C. for 5 minutes (one step); 98° C. for 30 seconds, 55° C. for 30 seconds, 72° C. for 3 minutes (35 cycles); 72° C. for 7 minutes (one step).

After the PCR reaction, DNA electrophoresis was conducted to verify the existence of DNA fragment of expected size. Then, PCR-M™ Clean Up system kit (GeneMark, Taiwan) was used and the product manual thereof was followed for recovering the PCR product. Afterward, the cloning of the agarase DNA fragment was performed by using CloneJET PCR Cloning Kit (Thermo Scientific, USA). The cloning procedure was performed by referring to the manual of the kit. The ligation mixture was transformed into E. coli ECOS™ 9-5. The details of the transformation can refer to the product instruction or be modified from standard experiment protocol in the field.

The transformed bacteria were incoluctated on LB solid medium containing ampicillin (100 μg/mL). After the colony was formed, performing colony PCR to select transformation strains. First of all, PCR mixture (100 μL) containing 1× Taq reaction buffer, 200 μM of dNTP (dATP, dTTP, dGTP and dCTP), 1 μM amplification primer and 2.5 U DreamTaq DNA polymerase (Thermo, USA). The PCR mixture was dispensed into PCR tubes (10 μL/tube). Colony was picked to PCR tubes by toothpick for PCR reaction. The PCR condition was set as 95° C. for 5 minutes (one step); 95° C. for 30 seconds, 55° C. for 30 seconds, 72° C. for 6 minutes (25 cycles); 72° C. for 7 minutes (one step). DNA electrophoresis was conducted to verify the existence of DNA fragment of expected size. The plasmid of the transformation strain selected, which was confirmed to carry the insert DNA, was extracted for DNA sequencing (Tri-I Biotech, Inc.). The plasmid confirmed by DNA sequence to carry the desired agarase DNA fragment was named as pJET-PBAGA-2-DS-DS; the agarase DNA fragment was a particular fragment of nucleotide sequence of *Paenibacillus agarexedens* genome but a gene thereof.

Establishment of the Present Expression Vector

These experiments were conducted to establish the expression vectors of the present agarase. Moreover, the present invention intended to establish various fragments of agarase gene based on the agarase DNA fragment of the above-obtained pJET-PBAGA-2-DS-DS by genetic engineering technology. The purpose of these experiments was to test if the activity of the agarase and the yield of the heterologous production thereof in E. coli expression system would be affected when a particular length of C' amino acids (C' deletion mutation) thereof were deleted. Seven expression vectors were established in these experiments, which are: pET-AgaB-2-775, pET-AgaB-2-875, pET-AgaB-2-975, pET-AgaB-2-1096, pET-AgaB-2-1275, pET-AgaB-2-1380, and pET-AgaB-2-1811. The details are described in the following paragraphs.

(1) Primer Set:

Primers designed specific to the DNA sequence encoding the $1^{st}$ to the $775^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-775XHOIHISR2
                                      SEQ ID NO: 24
CAATATCTCGAGTTAGTGGTGGTGGTGGTGGTGAAAGGTCAGCAGATTT
CCAGGC
```

Primers designed specific to the DNA sequence encoding the $1^{st}$ to the $875^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-875XHOIHISR2
                                      SEQ ID NO: 25
CAATATCTCGAGTTAGTGGTGGTGGTGGTGGTGATCCTGCGCAACAACC
TCC
```

Primers designed specific to the DNA sequence encoding the $1^{st}$ to the $975^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-975XHOIHISR2
                                      SEQ ID NO: 26
CAATATCTCGAGTTAGTGGTGGTGGTGGTGGTGCGGGGCAGTAAAATCA
AGGC
```

Primers designed specific to the DNA sequence encoding the $1^{st}$ to the $1096^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-1096XHOIHISR2
                                      SEQ ID NO: 27
CAATATCTCGAGTTAGTGGTGGTGGTGGTGGTGGTTCGGATTGCCAGGT
CCTG
```

Primers designed specific to the DNA sequence encoding the $1^{st}$ to the $1275^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-1275XHOIHISR2
                                      SEQ ID NO: 28
CAATATCTCGAGTTAGTGGTGGTGGTGGTGGTGAGTAGGCTGGATCGGC
TCGT
```

Primers designed specific to the DNA sequence encoding the $1^{st}$ to the $1380^{th}$ amino acids of the agarase (counting from N' terminal thereof):

```
Primer name: PBAGA2DSNDEIF
                                      SEQ ID NO: 22
GATATACATATGGCAGAGGTCAACGACGAGCTTC Primer name: PBAGA2-1380XHOIHISR2
                                      SEQ ID NO: 29
CAATATCTCGAGTTAGTGGTGGTGGTGGTGGTGGCCACCAGGTGGATTG
GAAG
```

Primers designed specific to the DNA sequence encoding the $1^{st}$ to the $1811^{th}$ amino acids of the agarase (counting from N' terminal thereof):

Primer name: PBAGA2DSNDEIF

SEQ ID NO: 22

GATATACATATGGCAGAGGTCAACGACGAGCTTC

Primer name: PBAGA2XHOIHISR2

SEQ ID NO: 30

CAATATCTCGAGTTAGTGGTGGTGGTGGTGGTGGATCAGATCAGACTTC
TCTAGCAATCT (2) PCR Mixture (50 µL):

Two different PCR mixtures were prepared for the establishment of the aforesaid 7 expression vectors.

PCR mixture 1 contained the following components: 1×GDP-HiFi PCR buffer B, 200 µM of dNTP (dATP, dTTP, dGTP and dCTP), 1 µM of amplification primer, 100 ng pJET-PBAGA-2-DS 及 1 U GDP-HiFi DNA polymerase.

PCR mixture 2 contained the following components: 1-Hi-Fi PCR buffer B, 200 µM of dNTP (dATP, dTTP, dGTP and dCTP), 1 µM of amplification primer, 100 ng pJET-PBAGA-2-DS and 1 U VELOCITY™ DNA polymerase.

(3) PCR Condition:

Two different PCR condition programs were set for the establishment of the aforesaid 7 expression vectors.

Condition program 1: 96° C. for 2 minutes (one step); 94° C. for 30 seconds, 60° C. for 30 seconds, 68° C. for 90 seconds (35 cycles); 68° C. for 5 minutes (one step).

Condition program 2: 98° C. for 5 minutes (one step); 98° C. for 30 seconds, 55° C. for 30 seconds, 72° C. for 3 minutes (35 cycles); 72° C. for 7 minutes (one step).

(4) Establishment of Expression Vectors:

The various DNA fragments of agarase genes of said pET-AgaB-2-775, pET-AgaB-2-875, pET-AgaB-2-975, pET-AgaB-2-1096, pET-AgaB-2-1275, pET-AgaB-2-1380, and pET-AgaB-2-1811 were prepared by PCR reaction using the aforesaid primers and PCR mixtures under the aforesaid PCR conditions. The experiment design was shown in the following table 1.

TABLE 1

Experiment design of the establishment of expression vectors.

| Name of vectors | Primer set | PCR mixture | PCR condition |
|---|---|---|---|
| pET-AgaB-2-775 | SEQ ID NO: 22<br>SEQ ID NO: 24 | PCR mixture 1 | PCR condition 1 |
| pET-AgaB-2-875 | SEQ ID NO: 22<br>SEQ ID NO: 25 | PCR mixture 1 | PCR condition 1 |
| pET-AgaB-2-975 | SEQ ID NO: 22<br>SEQ ID NO: 26 | PCR mixture 2 | PCR condition 2 |
| pET-AgaB-2-1096 | SEQ ID NO: 22<br>SEQ ID NO: 27 | PCR mixture 2 | PCR condition 2 |
| pET-AgaB-2-1275 | SEQ ID NO: 22<br>SEQ ID NO: 28 | PCR mixture 2 | PCR condition 2 |
| pET-AgaB-2-1380 | SEQ ID NO: 22<br>SEQ ID NO: 29 | PCR mixture 2 | PCR condition 2 |
| pET-AgaB-2-1811 | SEQ ID NO: 22<br>SEQ ID NO: 30 | PCR mixture 2 | PCR condition 2 |

After the PCR reaction, DNA electrophoresis was conducted to verify the existence of DNA fragment of expected size. Then, PCR-M™ Clean Up system kit (GeneMark, Taiwan) was used and the product manual thereof was followed for recovering the PCR product. Afterward, the PCR product were cut by NdeI and XhoI, and the resulted DNA fragments were ligated into pET-29a (+) (hereinafter referred as pET-29a; Merck Millipore, USA), which was cut in advanced by the same restrict enzymes by T4 DNA ligase. The ligation product was then transformed in to E. coli ECOS 9-5. Colony PCR was conducted afterward for selecting transformed strains. DNA electrophoresis was conducted to verify the existence of DNA fragment of expected size. Plasmids of the transformed strains being verified to carry the desired insert DNA was extracted for DNA sequencing. Plasmids being confirmed by DNA sequencing to carry the desired agarase gene were named respectively as pET-AgaB-2-775 (SEQ ID NO: 21), pET-AgaB-2-875 (SEQ ID NO: 20), pET-AgaB-2-975 (SEQ ID NO: 19), pET-AgaB-2-1096 (SEQ ID NO: 18), pET-AgaB-2-1275 (SEQ ID NO: 17), pET-AgaB-2-1380 (SEQ ID NO: 16), and pET-AgaB-2-1811 (SEQ ID NO: 15). The particular fragment contained in each expression vector above has relative position respectively on the genome as illustrated in FIG. 1.

Experiment 2: The Inducible Expression of the Recombinant Agarase of the Present Invention and the Detection Thereof.

Observation to the Expression of the Recombinant Agarase by Using Medium Plate

The expression vectors of the present invention were respectively transformed into E. coli BL 21 (DE3). Single colony was picked by sterile toothpick and inoculated on a solid culture plate containing kanamycin (final concentration: 30 µg/mL) and isopropyl β-D-1-thiogalactopyranoside (IPTG; final concentration: 1 mM). The culture plate was cultured for 48 hours at 30° C. Then, 10 mL of iodine solution (18 g/L iodine, 36 g/L potassium iodine) was flooded on the plate. After shaking for 10 minutes, the iodine solution was discarded and 10 mL NaCl (1 M) was added to wash off the staining. After that, colonies surrounded with transparent ring were those being able to express agarase.

Figure 2:
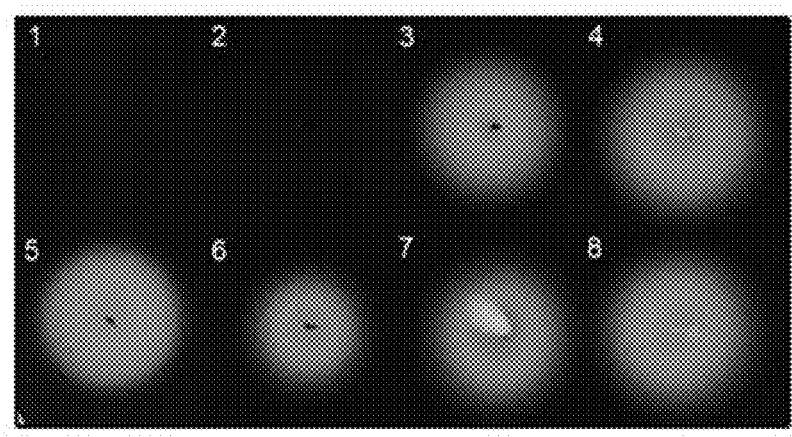
FIG. 2 displays the examination of the expression of the recombinant agarase by using culture plates in the Experiment 2. (1) BL21 (DE3) (pET-29a) as negative control. (2) BL21 (DE3) (pET-AgaB-2-775). (3) BL21 (DE3) (pET-AgaB-2-875). (4) BL21 (DE3) (pET-AgaB-2-975). (5) BL21 (DE3) (pET-AgaB-2-1096). (6) BL21 (DE3) (pET-AgaB-2-1275). (7) BL21 (DE3) (pET-AgaB-2-1380). (8) BL21 (DE3) (pET-AgaB-2-1811).

Please see the results shown in FIG. 2. Except the group of expression vector pET-AgaB-2-775, the agarases expressed by all other experiment groups of the present expression vectors exhibited activities and there was no apparent difference among them. The reason that the group of expression vector pET-AgaB-2-775 had no transparent ring might be because the transformed strain failed to express agarase or the agarase expressed had no activity.

Observation to the Expression of the Recombinant Agarase by Protein Electrophoresis Single colony was picked by sterile toothpick and inoculated in 5 mL of LB culture medium containing kanamycin (final concentration: 30 µg/mL). The culture medium was cultured at 37° C. and shaken at 180 rpm overnight. 100 µL of the cultured broth was then added to 10 mL of fresh LB culture medium containing kanamycin (final concentration: 30 µg/mL). The culture medium was cultured at 37° C. and shaken at 180 rpm until the OD$_{600}$ thereof reaching about 0.4 to 0.6. Afterward, 0.1 mM of IPTG was added at particular temperature to induce the expression of the recombinant protein. After 4 hours and 24 hours induction, 2 mL of broth was collected respectively for centrifugation (20,630×g, 5 minutes, 4° C.) to collect the pellet. The proteins contained in the pellet were separated based on their solubility. Protein electrophoresis was then conducted to observe the solubility of the expressed agarase.

Figure 3:
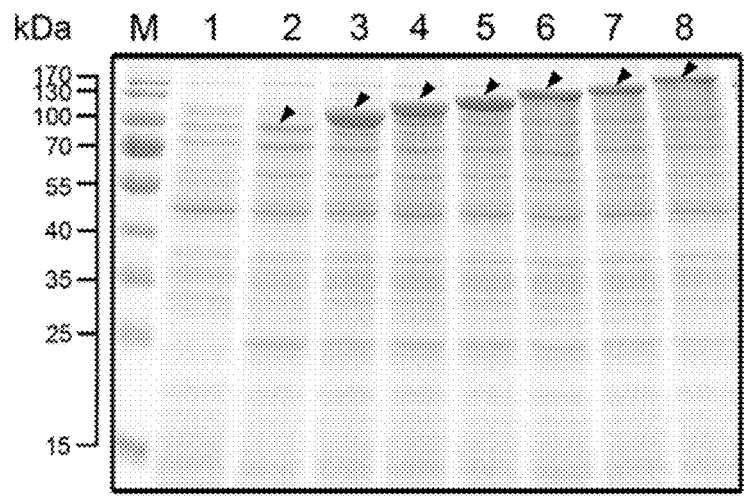
FIG. 3 shows the examination of the expression of the recombinant agarase by protein electrophoresis in the Experiment 2. Lane M: PageRuler™ Prestained Protein Ladder. Lane 1: BL21 (DE3) (pET-29a). Lane 2: BL21 (DE3) (pET-AgaB-2-775). Lane 3: BL21 (DE3) (pET-AgaB-2-875). Lane 4: BL21 (DE3) (pET-AgaB-2-975). Lane 5: BL21 (DE3) (pET-AgaB-2-1096). Lane 6: BL21 (DE3) (pET-AgaB-2-1275). Lane 7: BL21 (DE3) (pET-AgaB-2-1380). Lane 8: BL21 (DE3) (pET-AgaB-2-1811).

FIG. 3 displayed the results of this experiment. According to the data, the agarases expressed by the present expression vectors showed solubility. Together with the data shown in FIG. 2, those data hinted that the reason why the group of pET-AgaB-2-775 had no transparent ring observed on the culture plate activity test might be because the agarase expressed by the expression vector has no activity.

Activity Test of the Present Agarase

Single colony was picked by sterile toothpick and inoculated in 5 mL of LB culture medium containing kanamycin (final concentration: 30 μg/mL). The culture medium was cultured at 37° C. and shaken at 180 rpm overnight. 100 μL of the cultured broth was then added to 10 mL of fresh LB culture medium containing kanamycin (final concentration: 30 μg/mL). The culture medium was cultured at 37° C. and shaken at 180 rpm until the $OD_{600}$ thereof reaching about 0.4 to 0.6. Afterward, 0.1 mM of IPTG was added at particular temperature to induce the expression of the recombinant protein. The induction was made for 4 hours. Then, 1 mL of broth was collected and the concentration thereof was adjusted to $OD_{600}$ 2.0. After that, the broth was put into the centrifuge (20,630×g, 5 minutes, 4° C.) to collect the pellet. The pellet was re-suspended in lysis buffer (20 mM sodium phosphate, 500 mM NaCl and pH 7.4) to crush the bacteria therein. After another centrifugation (20,630×g, 5 minutes, 4° C.), the supernatant (containing the soluble intracellular proteins) was collect for testing the enzymatic activity thereof.

The test of the enzymatic activity was proceeded as follows. 850 μL of 0.24% (w/v) low melting point agarose solution (substrate of agarase) was mixed well with 100 μL of 0.5 M phosphate buffer solution (pH 6) and heated until being completed dissolved. Then the mixture was placed at 40° C. for 10 minutes. 50 μL of the aforesaid supernatant was added to the substrate of the enzymatic reaction and reacted at 40° C. for 10 minutes. After the reaction, 1 mL of DNS solution (1% 3,5-dinitrosalicylic acid, 30% potassium sodium tartrate tetrahydrate, 1.6% NaOH) was added in immediately and heated at 100° C. for 5 minutes. After the reaction cooled down, 1 mL of deionized water was added and 100 μL of the mixture was transferred to a 96-well plate. The absorbance of the mixture at 540 nm was detected by an ELISA reader. DNS colorimetric reactions were conducted for D-galactose solutions of various concentrations to create a standard curve of reducing sugar. According to the standard curve, the amount of the reducing sugar made out of the enzymatic reaction by the present agarase can be calculated based on the above-mentioned absorbance at 540 nm. One activity unit (U) was defined as the necessary amount of the enzyme at issue to produce 1 μmole of galactose per minute.

Figure 4:
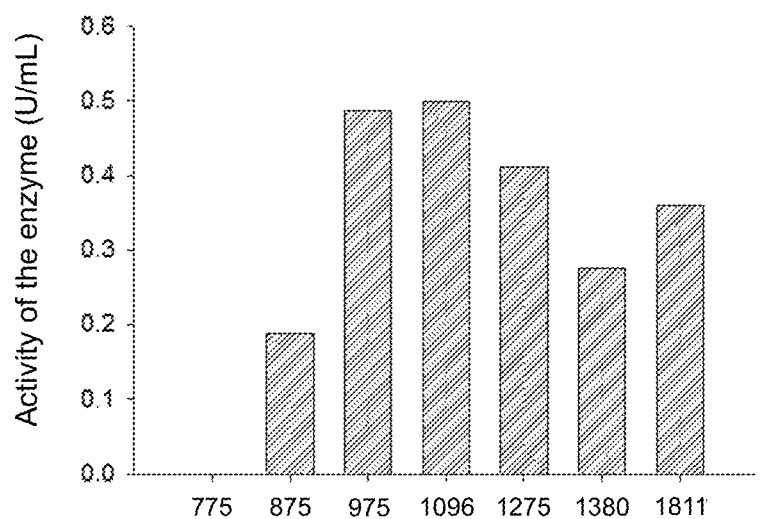
FIG. 4 illustrates the results of activity testing of the agarase in the Experiment 2. 775: the agarase expressed by the present vector pET-AgaB-2-775. 875: the agarase expressed by the present vector pET-AgaB-2-875. 975: the agarase expressed by the present vector pET-AgaB-2-975. 1096: the agarase expressed by the present vector pET-AgaB-2-1096. 1275: the agarase expressed by the present vector pET-AgaB-2-1275. 1380: the agarase expressed by the present vector pET-AgaB-2-1380. 1811: the agarase expressed by the present vector pET-AgaB-2-1811.

The enzymatic activity of each milliliter of culture medium (U/mL) was shown in FIG. 4. The results proved that the agarase expressed by the present expression vector pET-AgaB-2-775 did fail to exhibit activity. That is to say, the first N' terminal 857 amino acid of the present agarase was essential for the activity thereof.

Experiment 3: Purification of the Present Recombinant Agarase and Analysis of the Properties Thereof Inducible Expression and Purification of the Recombinant Agarase Single colony was picked by sterile toothpick and inoculated in 12 mL of LB culture medium containing kanamycin (final concentration: 30 μg/mL). The culture medium was cultured at 37° C. and shaken at 180 rpm overnight. 10 mL of the cultured broth was then added to 1 L of fresh LB culture medium containing kanamycin (final concentration: 30 μg/mL). The culture medium was cultured at 37° C. and shaken at 180 rpm until the $OD_{600}$ thereof reaching about 0.4 to 0.6. Afterward, 0.1 mM of IPTG was added at particular temperature (18° C., 25° C., 30° C., 37° C.) to induce the expression of the recombinant protein. After 24 hours induction, the broth was put into the centrifuge (10,000×g, 10 minutes, 4° C.) to collect the pellet. The pellet was re-suspended in 10 mL of lysis buffer (20 mM sodium phosphate, 500 mM NaCl and pH 7.4), and the bacteria therein were crushed by a sonicator. Then, another centrifugation was conducted and the supernatant was collected. The supernatant was filtered by a 0.22 μm filter.

Afterward, an immobilized-metal ion affinity chromatography was conducted for protein purification taking the advantage of the nature that the C' terminal His tag of the recombinant protein would form coordinate covalent bond with nickel ion or cobalt ion. The procedure of purification of the recombinant agarase was conducted by using protein liquid chromatography system ÄKTA prime plus (GE Healthcare, Sweden) equipped with 5 mL HiTrap™ Ni excel column (GE Healthcare, Sweden). First of all, the HiTrap™ Ni excel column was balanced by 25 mL of lysis buffer and the above-obtained supernatant was introduced into the column. After all samples were introduced, 100 mL of wash buffer [20 mM sodium phosphate, 500 mM NaCl, 30 mM imidazole, pH 7.4] was introduced to wash off non-specific binding protein. Lastly, 150 mL of elution buffer [20 mM sodium phosphate, 500 mM NaCl, 250 mM imidazole, pH 7.4] was introduced to elute the agarase binding on the resin. The last step was taking the advantage of the binding competition of high concentration of imidazole and the recombinant agarase on the resin, which causes agarse to be elute therefrom. The purified agarase solution was positioned in an Amicon ultra-15 ultracel-30K centrifuge tube (Merck Millipore, USA) for centrifugation (2,600×g) at 4° C. to a proper volume and then stocked at 4° C.

The recombinant agarases obtained by the expression vectors of the present invention in various temperature were shown in the following table 2. In E. coli BL21(DE3) (pET-AgaB-2-875), the most production of soluble agarase was made by 24 hours induction at 18° C. In E. coli BL21(DE3) (pET-AgaB-2-975), the most production of soluble agarase was made by 24 hours induction at 18° C. In E. coli BL21(DE3) (pET-AgaB-2-1096), the most production of soluble agarase was made by 24 hours induction at 18° C. In E. coli BL21(DE3) (pET-AgaB-2-1275), the most production of soluble agarase was made by 24 hours induction at 18° C. In E. coli BL21(DE3) (pET-AgaB-2-1380), the most production of soluble agarase was made by 24 hours induction at 18° C. In E. coli BL21(DE3) (pET-AgaB-2-1811), the most production of soluble agarase was made by 24 hours induction at 18° C. The aforesaid results indicated lower temperature or longer time period of induction were favorable for increasing the production of the soluble agarase deletion mutations of the present invention. Except that, the results also shown that the C' termination deletion mutation was good for increasing the production of the recombinant proteins.

TABLE 2

Production of agarase by using the expression vectors of the present invention.

| Host | Induction Temp. (° C.) | Production of soluble agarase after 4 hours induction (mg/L) | Production of soluble agarase after 24 hours induction (mg/L) |
|---|---|---|---|
| BL21(DE3)(pET-AgaB-2-875) | 18 | 35 | 279 |
| | 25 | 178 | 192 |
| | 30 | 235 | 220 |
| | 37 | 132 | 113 |
| BL21(DE3)(pET-AgaB-2-975) | 18 | 21 | 294 |
| | 25 | 136 | 158 |
| | 30 | 167 | 170 |
| | 37 | 131 | 123 |

TABLE 2-continued

Production of agarase by using the expression vectors of the present invention.

| Host | Induction Temp. (° C.) | Production of soluble agarase after 4 hours induction (mg/L) | Production of soluble agarase after 24 hours induction (mg/L) |
|---|---|---|---|
| BL21(DE3)(pET-AgaB-2-1096) | 18 | 22 | 189 |
|  | 25 | 116 | 144 |
|  | 30 | 129 | 139 |
|  | 37 | 112 | 102 |
| BL21(DE3)(pET-AgaB-2-1275) | 18 | 18 | 179 |
|  | 25 | 68 | 84 |
|  | 30 | 97 | 143 |
|  | 37 | 87 | 77 |
| BL21(DE3)(pET-AgaB-2-1380) | 18 | 19 | 170 |
|  | 25 | 84 | 110 |
|  | 30 | 97 | 131 |
|  | 37 | 77 | 83 |
| BL21(DE3)(pET-AgaB-2-1811) | 18 | 5 | 42 |
|  | 25 | 49 | 81 |
|  | 30 | 62 | 56 |
|  | 37 | 70 | 66 |

Figure 5:
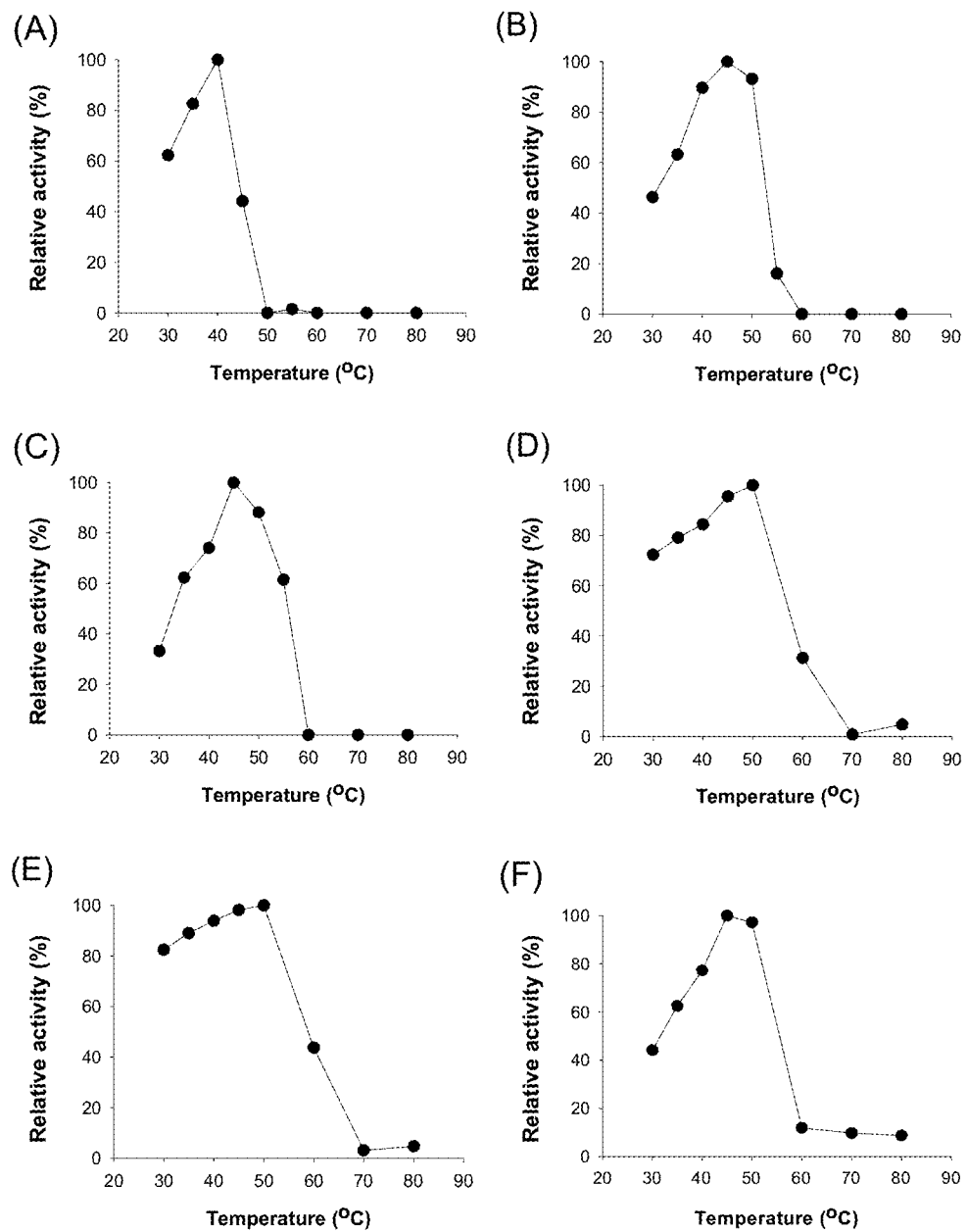
FIG. 5 displays the results of testing the preferable catalytic temperature in the Experiment 3. (A) AgaB-2-875. (B) AgaB-2-975 (C) AgaB-2-1096. (D) AgaB-2-1275. (E) AgaB-2-1380. (F) AgaB-2-1811.
Figure 6:
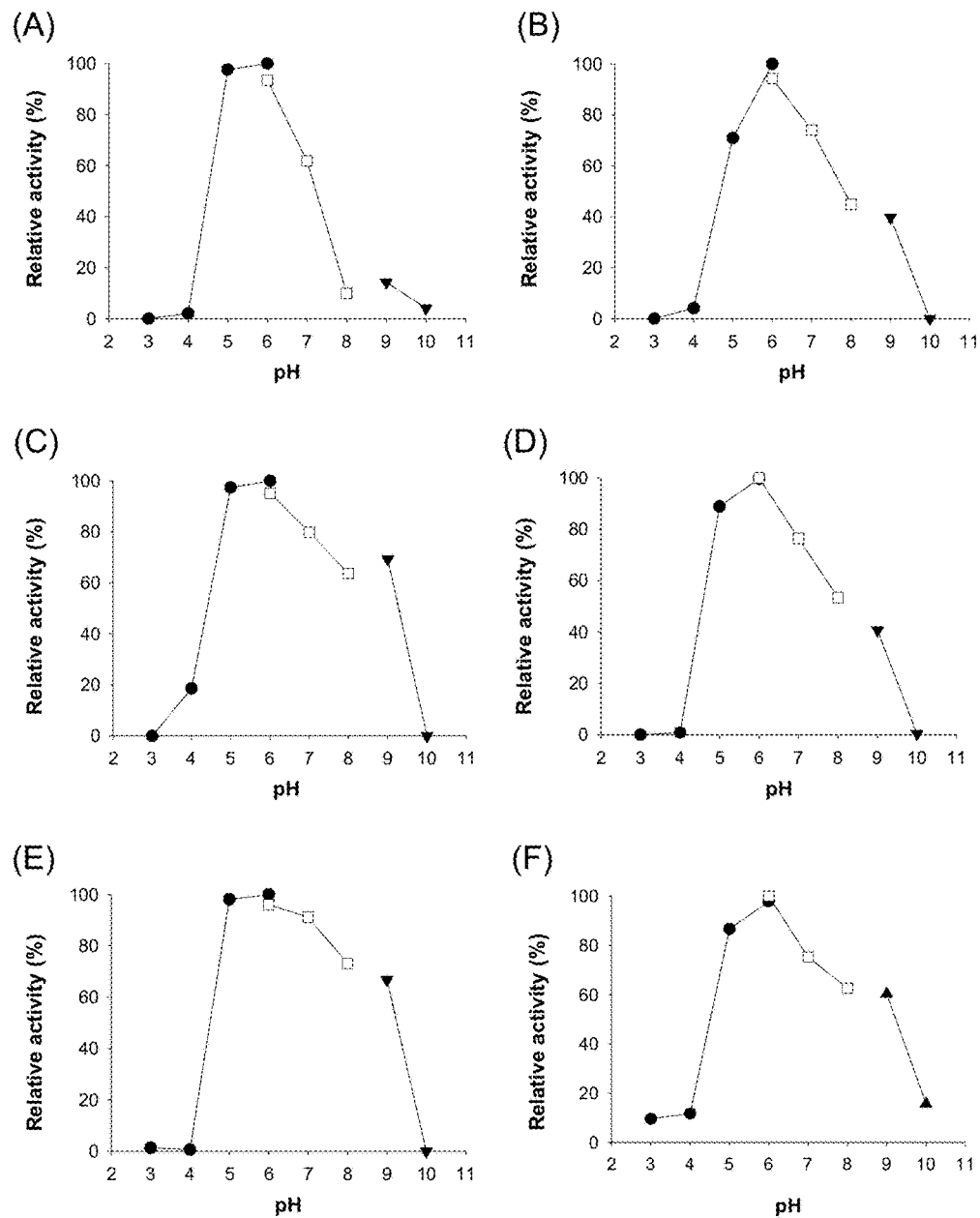
FIG. 6 is the results of testing the preferable catalytic pH value in the Experiment 3. (A) AgaB-2-875. (B) AgaB-2-975 (C) AgaB-2-1096. (D) AgaB-2-1275. (E) AgaB-2-1380. (F) AgaB-2-1811. ● represents citrate buffer solution (pH 3~6). □ represents phosphate buffer solution (pH 6~8). ▲ represents glycine-NaOH buffer solution (pH 9~10).

Examination to the Properties of the Present Recombinant Agarase (1) Preferable Catalytic Temperature:

850 μL of 0.24% (w/v) low melting point agarose solution was mixed with 100 μL of 0.5 M phosphate buffer solution to form a mixture. The mixture was heated to let the substances therein dissolved. Then, the mixture was placed at different temperature (from 30 to 80° C.) for 10 minutes. After that, 50 μL of agarase solution (0.1 U) was added in each tube containing the mixture and the mixture was placed at different temperature (from 20 to 80° C.) for reaction for 10 minutes. The subsequent DNS colorimetric reaction and calculation to the enzymatic activity unit were made as set forth above. The highest enzymatic activity unit detected in the aforesaid reactions was defined as 100%; that is the enzymatic activity obtained at the most preferable temperature among them. Then, relative enzymatic activities to the highest enzymatic activity obtained at other temperatures were calculated. According to the results of the experiments (FIG. 5), the preferable catalytic temperature of each agarase of the present invention was between 40 to 50° C.; wherein the preferable catalytic temperatures of AgaB-2-875, AgaB-2-975, AgaB-2-1096, AgaB-2-1275, AgaB-2-1380 and AgaB-2-1811 were 40° C., 45° C., 45° C., 50° C., 50° C. and 45° C., respectively.

(2) Preferable Catalytic pH Value:

850 μL of 0.24% (w/v) low melting point agarose solution was mixed respectively with 100 μL of 0.5 M citric acid buffer solution (pH 3-6), phosphate buffer solution (pH 6-8), and glycine-NaOH buffer solution (pH 9-10) to form mixtures. The mixtures were heated to let the substances therein dissolved and reaction substrates of different pH value were prepared. 950 μL of each the reaction substrate was placed at the above-obtained preferable catalytic temperature of the enzyme for 10 minutes. Then, 50 μL of agarase solution (0.1 U) was added in and reacted at the preferable catalytic temperature for another 10 minutes. The subsequent DNS colorimetric reaction and calculation to the enzymatic activity unit were made as set forth above. The highest enzymatic activity unit detected in the aforesaid reactions was defined as 100%; that is the enzymatic activity obtained at the most preferable catalytic pH value. Then, relative enzymatic activities to the highest enzymatic activity obtained at other pH values were calculated. The experiment results showed that the preferable pH value for each agarase of the present invention was 6.

(3) Enzymatic Kinetic Analysis:

850 μL of low melting point agarase solutions of various concentrations (0.24~3.53%, w/v) was respectively mixed with 100 μL of 0.5 M phosphate buffer solution to form mixtures. The mixtures were heated to let the substances therein dissolved and placed at the above-obtained preferable catalytic temperature of the enzyme for 10 minutes. After that, 50 μL of agarase solution (0.1 U) was added in and reacted at the preferable catalytic temperature for 10 minutes. The subsequent DNS colorimetric reaction and calculation to the enzymatic activity unit were made as set forth above. Diagram of substrate concentration versus enzymatic reaction rate was made and the saturation curve of the substrate can be obtained. Based on that, the value of the saturation concentration (Michaelis constant, Km) and the maximum reaction rate (Vmax) can be calculated by using Lineweaver-Burk Plot (Double Reciprocal Plot). Then, turnover number (Kcat) and catalytic efficiency (Kcat/Km) can be calculated by using the Vmax value.

The results of the experiments were shown in the following table 3. The previous experiments set forth in the precedent paragraphs had shown that the C' terminal deletion mutation was helpful to increase the production. This experiment further verified the C' terminal deletion mutation might decrease the catalytic efficiency (Kcat/Km). Nevertheless, the present recombinant agarase did have catalytic efficiency sufficient for commercialization especially to AgaB-2-1275 and AgaB-2-1811, which exhibited better catalytic efficiency among others.

TABLE 3

Result of enzymatic kinetic analysis

| Enzyme | Vmax (μmole/min/mg) | Km (mg/mL) | Kcat ($S^{-1}$) | Kcat/Km ($SM^{-1}$) |
|---|---|---|---|---|
| AgaB-2-875 | 20.74 | 10.54 | 34.31 | $3.91 \times 10^4$ |
| AgaB-2-975 | 23.87 | 6.12 | 43.67 | $8.56 \times 10^4$ |
| AgaB-2-1096 | 15.50 | 8.54 | 31.63 | $4.44 \times 10^4$ |
| AgaB-2-1275 | 30.67 | 8.13 | 72.49 | $1.07 \times 10^5$ |
| AgaB-2-1380 | 18.55 | 11.10 | 47.03 | $5.08 \times 10^4$ |
| AgaB-2-1811 | 15.81 | 4.75 | 52.32 | $1.32 \times 10^5$ |

(4) Effect of Metal Ion on the Activity of the Present Agarase:

100 μL of 20 mM metal ion solution, 750 μL of 0.27% (w/v) agarose solution, and 100 μL of 0.5 M phosphate buffer solution (pH 6) were mixed evenly and heated until the substrates therein were completely dissolved. Then the mixture was placed at the preferable catalytic temperature for 10 minutes. Afterward, 50 μL of agarase solution (0.1 U) was added in and the mixture was placed at the preferable catalytic temperature for reaction for another 10 minutes. The subsequent DNS colorimetric reaction and calculation to the enzymatic activity unit were made as set forth above. Comparison between the relative enzymatic activities showed the effects of different metal salts on the hydrolysis ability of the recombinant agarases of the present invention. The following table 4 shows the results of the experiments. Metal salts (metal ions) did increase the activity of the present agarases (AgaB-2-1275 and AgaB-2-1811); wherein $MnCl_2$ was able to increased at least 2 fold of the activity of the present agarase.

TABLE 4

Effects of metal ions on the activity of agarase.

| Metal salt (metal ion) | Relative activity of AgaB-2-1275 (%) | Relative activity of AgaB-2-1811 (%) |
|---|---|---|
| none | 100% | 100% |
| $Cu^{2+}$ ($CuSO_4$) | 103% | 100% |
| $K^+$ (KCl) | 106% | 114% |
| $Zn^{2+}$ ($ZnSO_4$) | 108% | 108% |
| $Fe^{2+}$ ($FeSO_4$) | 119% | 119% |
| $Ba^{2+}$ ($BaCl_2$) | 109% | 114% |
| $Na^+$ (NaCl) | 105% | 97% |
| $Sr^{2+}$ ($SrCl_2$) | 108% | 98% |
| $Co^{2+}$ ($CoCl_2$) | 151% | 198% |
| $Mg^{2+}$ ($MgSO_4$) | 114% | 116% |
| $Mn^{2+}$ ($MnCl_2$) | 201% | 280% |
| $Ca^{2+}$ ($CaCl_2$) | 107% | 119% |
| $Al^{3+}$ ($AlCl_3$) | 106% | 120% |

Figure 7:
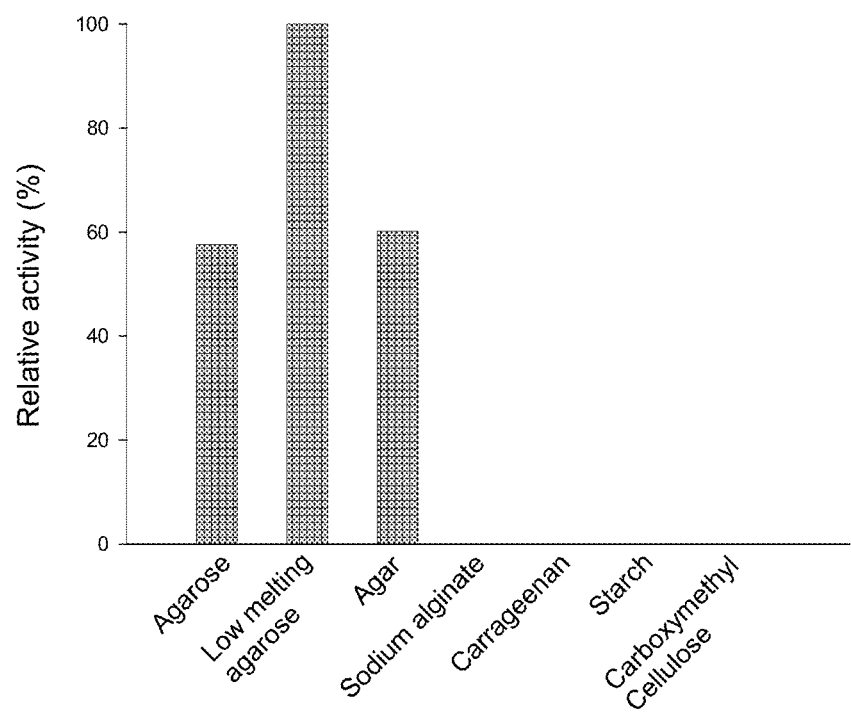
FIG. 7 shows the results of the substrate analysis in the Experiment 3.
Figure 8:
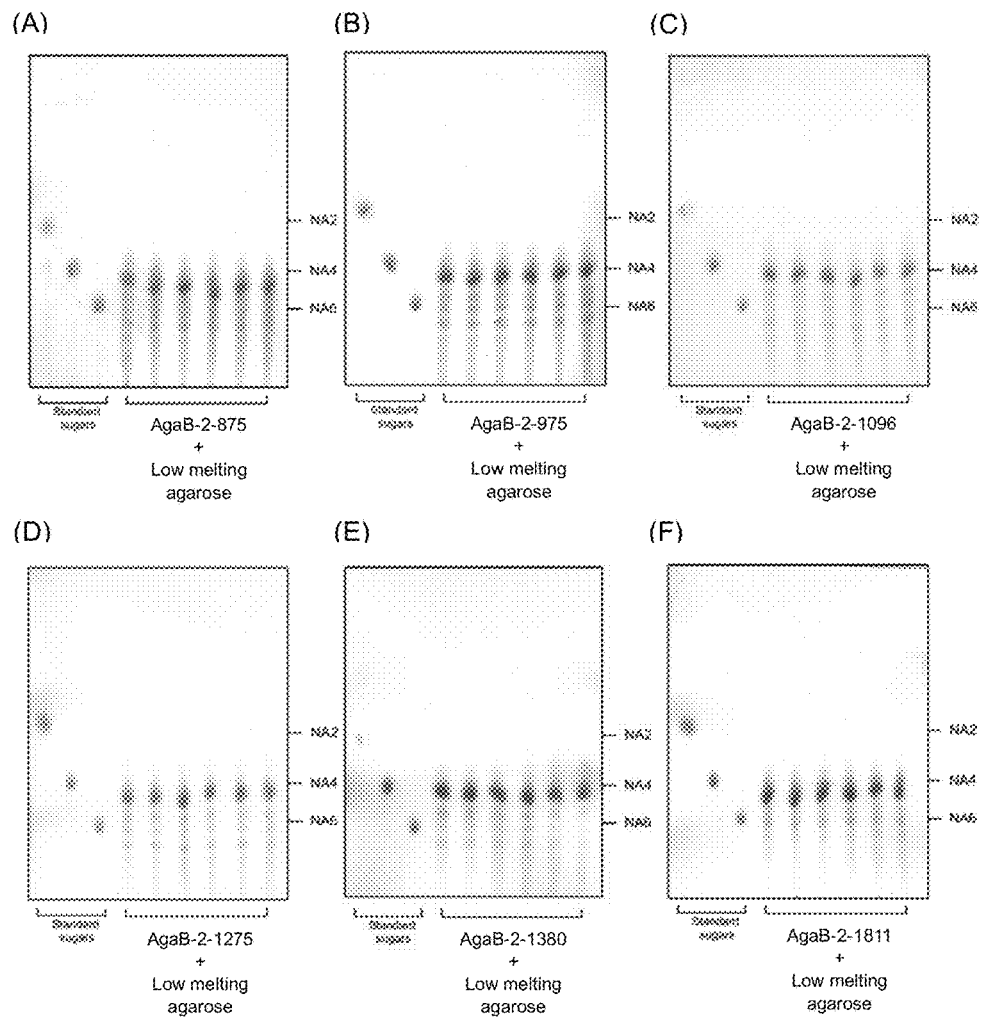
FIG. 8 is the results of the product analysis in the Experiment 3.

(5) Analysis of the Suitable Substrate of the Present Agarase:

These experiments were conducted to examine substrates, which were able to be hydrolyzed by the present agarase. 850 µL of 0.24% (w/v) agarose solution, low melting point agarose solution, agar solution, sodium alginate solution, carrageenan solution, soluble starch solution, and sodium carboxymethylcellulose solution were respectively mixed with 100 µL of 0.5 M PBS (pH 6) and heated until all the substrates therein were completely dissolved. The mixtures were placed at the preferable catalytic temperature for 10 minutes. Then, 50 µL of agarase solution (0.1 U) was added in to the mixture of substrates and the mixture was placed at the preferable catalytic temperature for reaction for another 10 minutes. The subsequent DNS colorimetric reaction and calculation to the enzymatic activity unit were made as set forth above. The experiments results shows (FIG. 7) the present recombinant agarase had the best hydrolysis activity to low melting point agaros and also exhibited hydrolysis activity to agarose and agar. However, the present agarase failed to hydrolyze sodium alginate, carrageenan, soluble starch, and sodium carboxymethylcellulose.

(6) Examination of the Hydrolysis Product of the Present Agarase:

These experiments were conducted by using thin layer chromatography (TLC) to examine the hydrolysis product of the agrases. 850 µL of 1.18% (w/v) low melting point agarose solution was respectively mixed with 100 µL of 0.5 M PBS (pH 6) and heated until all the substrates therein were completely dissolved. The mixture was placed at 40° C. for 10 minutes. Then, 50 µL of agarase solution (2 U/mL) was added in to the mixture of substrates and the mixture was placed at 40° C. for reaction for another 24 hours. Afterward, the mixture after reaction was centrifuged (15,000 rpm, 4° C., 10 minutes), filtered through 0.22 µm filter membrane, and stocked at −20° C. 8 µL of the hydrolysis products of the present agarase, 2 µL of neoagarobiose solution (10 µg/µL), 2 µL of neoagarotetraose solution (10 µg/µL) and 2 µL of neoagarohexose solution (10 µg/µL) were dotted on silica gel 60 thin-layer chromatography (TLC) plates (Merck Millipore, USA). After the samples dotted on the sheet were dried, the films were inserted obliquely into developing buffer (50% of 1-butanol, 25% of acetic acid, 25% of deionized water) contained in a developing tank. After developing, the TLC plates were taken out for drying and then 0.1 M of aniline phthalate solution (Sigma-Aldrich, USA) was sprayed over the plates. After drying, the plates were heated to show the color and the Rf value (retention factor value) of testing samples and standard sample was calculated. The hydrolysis product of agarase was identified through the Rf value. The results showed the main hydrolysis products of the present agarase was neoagarotetraose, which contained at least 40 wt % of the product. The hydrolysis product also contained neoagarohexose and oligosaccharide containing at least six saccharide units. It was notable that the product contained substantially no neoagarobiose.

What is claimed is:

1. A β-agarase, comprising SEQ ID NO: 06; provided that the β-agarase is SEQ ID NO: 01 with more than or equal to 431 amino acids truncation at C-terminal.

2. The β-agarase of claim 1, consisting of SEQ ID NO: 02.

3. The β-agarase of claim 1, consisting of SEQ ID NO: 03.

4. The β-agarase of claim 1, consisting of SEQ ID NO: 04.

5. The β-agarase of claim 1, consisting of SEQ ID NO: 05.

6. The β-agarase of claim 1, consisting of SEQ ID NO: 06.

7. A composition for digesting polysaccharide with α-1,3 and β-1,4 glycosidic linkage, comprising:
   0.1 to 10 U/mL of the β-agarase of claim 1; and
   1 to 2 mM of a salt;
   wherein said U/mL and said mM are based on a total volume of said composition.

8. The composition of claim 7, further comprising 50 to 200 mM of a buffer based on a total volume of said composition.

9. The composition of claim 7; wherein said salt is KCl, $ZnSO_4$, $FeSO_4$, $BaCl_2$, NaCl, $SrCl_2$, $CoCl_2$, $MgSO_4$, $MnCl_2$, $CaCl_2$, $AlCl_3$, or a combination thereof.

10. The composition of claim 9; wherein said salt is $FeSO_4$, $CoCl_2$, $MnCl_2$, $CaCl_2$, $AlCl_3$, or a combination thereof.

11. The composition of claim 7, said polysaccharide with α-1,3 and β-1,4 glycosidic linkage is agarose, low melting point agarose, agar, seaweed polysaccharide crude extract, or a combination thereof.

12. The composition of claim 7, comprising 2 to 10 U/mL of said β-agarase.

* * * * *